(12) United States Patent
Arnold et al.

(10) Patent No.: US 7,098,010 B1
(45) Date of Patent: Aug. 29, 2006

(54) DIRECTED EVOLUTION OF OXIDASE ENZYMES

(75) Inventors: Frances H. Arnold, Pasadena, CA (US); Ioanna P. Petrounia, Pasadena, CA (US); Lianhong Sun, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/722,602

(22) Filed: Nov. 27, 2000

Related U.S. Application Data

(63) Continuation-in-part of application No. 09/571,553, filed on May 16, 2000.

(51) Int. Cl.
*C12N 9/02* (2006.01)
*C12N 1/20* (2006.01)
*C12N 15/00* (2006.01)
*C12Q 1/68* (2006.01)
*C12Q 1/00* (2006.01)
*C12P 21/04* (2006.01)
*C07H 21/04* (2006.01)

(52) U.S. Cl. .............. 435/189; 435/4; 435/6; 435/69.1; 435/71.1; 435/440; 435/252.3; 435/320.1; 536/23.2; 536/23.7

(58) Field of Classification Search .............. 435/190, 435/252.3, 320.1, 440, 189, 4, 6, 69.1, 71.1; 536/23.2, 23.74, 23.7
See application file for complete search history.

(56) References Cited

U.S. PATENT DOCUMENTS

| | | | |
|---|---|---|---|
| 5,605,793 A | 2/1997 | Stemmer | 435/6 |
| 5,741,691 A | 4/1998 | Arnold et al. | 435/197 |
| 5,811,238 A | 9/1998 | Stemmer et al. | 435/6 |
| 5,830,721 A | 11/1998 | Stemmer et al. | 435/172.1 |
| 5,837,458 A | 11/1998 | Minshull et al. | 435/6 |
| 5,965,408 A | 10/1999 | Short | 435/91.1 |
| 6,090,604 A | 7/2000 | Golightly et al. | 435/190 |
| 6,498,026 B1 * | 12/2002 | Delagrave et al. | 435/190 |

FOREIGN PATENT DOCUMENTS

| | | |
|---|---|---|
| EP | 752008 | 2/1997 |
| EP | 932670 | 8/2000 |
| WO | WO 95/22625 | 8/1995 |
| WO | WO 97/20078 | 6/1997 |

(Continued)

OTHER PUBLICATIONS

Rogers, M.S. et al., *Characterization of the Active Site of Galactose Oxidase and Its Active Site Mutational Variants Y495/F/H/K and W290H by Circular Dichroism Spectroscopy*. Inorganica Chemica Acta.

(Continued)

*Primary Examiner*—P. Achutamurthy
*Assistant Examiner*—Yong D. Pak
(74) *Attorney, Agent, or Firm*—Buchanan Ingersoll LLP

(57) ABSTRACT

This invention relates to the expression of improved polynucleotide and polypeptide sequences encoding for eukaryotic enzymes, particularly oxidase enzymes. The enzymes are advantagoeusly produced in conventional or facile expression systems. Various methods for directed evolution of polynucleotide sequences can be used to obtain the improved sequences. The improved characteristics of the polypeptides or proteins generated in this manner include improved expression, enhanced activity toward one or more substrates, and increased thermal stability. In a particular embodiment, the invention relates to improved expression of the galactose oxidase gene and galactose oxidase enzymes. GAO mutants that are highly active and/or thermostable are disclosed.

2 Claims, 49 Drawing Sheets

FOREIGN PATENT DOCUMENTS

| | | |
|---|---|---|
| WO | WO 97/35966 | 10/1997 |
| WO | WO 98/31837 | 7/1998 |
| WO | WO 98/41653 | 9/1998 |
| WO | WO 98/42832 | 10/1998 |
| WO | WO 00/00632 | 1/2000 |
| WO | WO 00/04190 | 1/2000 |
| WO | WO 00/09679 | 2/2000 |
| WO | WO 00/18906 | 4/2000 |
| WO | WO 01/62938 A2 | 8/2001 |

OTHER PUBLICATIONS

Adanyi, N., et al. European Food Research and Technology, 1999; 209:220-226.
Aisaka, K., et al., Agric. Biol. Chem., 1981; 45(10):2311-2316.
Amaral, D., et al., Methods Enzymol., 1966; 9:87-92.
Anfinsen, C. B., Science, 1973; 181:223.
Arkin, A., et al., Proc. Natl. Acad. Sci. USA, 1992; 89:7811.
Arnold, F. H., Accounts Chem. Res., 1998; 31:125-131.
Arnold, F.H., et al., Adv. Biochem. Eng. Biotechnol., 1997;58:1-14.
Arnold. F.H. , FASEB J., 1993; 7:744-749.
Arts, S.J.H.F., et al., Synthesis-Stuttgart, 1997; 6:597-613.
Avigad, G., Arch. Biochem. Biophys., 1985; 239(2):531-537.
Avigad, G., Anal. Biochem., 1978;86:470-476.
Avigad, G., et al., J. Biol. Chem., 1962; 237;2736-2743.
Baron, A. J., et al., J. Biol. Chem., 1994; 269:25095-25105.
Beckman, R. A., et al., Biochemistry, 1994; 24:5810.
Bernarderz-Clark, E. D.; Georgiou, G. Inclusion Bodies and Recovery of Proteins from the Aggregated States. In Protein Refolding; Bernarderz-Clark, E. D., Georgiou, G., Eds.; ACS: Washington, D. C. p. 1-20 (1990).
Better, M., et al., Science, 1988; 240:1041.
Borman, C. D., et al., J. Biol. Inorg. Chem., 1997; 2:480-487.
Bradford, M., Anal. Biochem., 1978; 72:248-254.
Calderhead, D. M., et al., J. Biol. Chem., 1988; 263:12171-12174.
Caldwell, R. C.; Joyce, G. F. PCR Methods Applic. 2, 28(1992).
Calvin, N.M., et al , J. Bacteriol., 1988; 170(6):2796-2801.
Carbon, J., Clarke, L.; Ilgen, C.; Ratzkin, B. The Construction and Use of Hybrid Plasmid Gene Banks in *Escherichia coli*. In Recombinant Molecules: Impact on Science and Society; Beers, R. F. J., Bassett, E. G., Eds; Raven Press: New York, pp. 355-378 (1977).
Castelli, M. C. et al., Gene, 1994; 142 113.
Chang et al., Nature Biotechnol, 1999; 17:793-797.
Chen, K. & Arnold, F.H., Proc. Natl. Acad. Sci. USA, 1993; 90:5618-5622.
Cherry, J. R., et al., Nature Biotechnol., 1999; 17:379-384.
Christians et al., Nature Biotechnol., 1999; 17:259-264.
Cleland, J. L, et al., Bio/Technology, 1990; 8:1274.
Crameri, A , et al., Nature, 1998, 391:228-231.
Crameri, A. , et al., Nature Biotechnol., 1997; 15:436-438.
Crameri, A , et al., Nature Biotechnol., 1996; 14:315-318.
Crameri, A , et al., Nature Med., 1996; 2:100-103.
Crameri, A , et al., Angew. Chem. Int. Ed. Engl., 1980; 19:546-547.
De Sutter, et al., GENE, 1994; 141:163.
Delagrave et al., Bio/Technology, 1993; 11:1548.
Delagrave et al. Protein Engineering, 1993; 6:327.
Dower, W.J., et al , Nucleic Acids Res., 1988; 16(13):6127-6145.
Dunford, H.B., Peroxidases in Chemistry and Biology, 1991; vol. 2. pp. 1-24.
Egorov, A. M., et al., Ann. N. Y. Acad. Sci., 1991; 646:35.
Fiedler, K. & Simons, K., Cell, 1995; 81:309-312.
Fitzgerald et al., Biochemistry, 1994; 33:3807.
Gahmberg, C. G., and Tolvanen, M., Methods Enzymol., 1994; 230:32-44.
Gajhede, M., et al., Nature Struct. Biol., 1997; 4:1032.
Gazaryan, I.G., LABPV Newsletters, 1994; 4:8-15.
Gietz, D., et al., Yeast, 1995; 11 355.
Gillam, E.M., et al , Arch. Biochem. Biophys., 1995; 319:540-550.
Giver, L., et al., Proc. Natl. Acad. Sci. USA, 1998; 95:12809-12813.
Giver, L., and Arnold, F.H. Curr. Opinion Chem. Biol., 1998; 2: 335-338.
Goldman, E. R. and Youvan D. C., Bio/Technology, 1992; 10:1557.
Goodin, D. B., et al., Biochemistry, 1991; 30:4953.
Goshorn, S. C., et al., Cancer Res., 1993; 53:2123.
Gramm, H. et al., Proc. Natl. Acad. Sci. USA, 1992; 89:3576.
Guengerich et al., Meth. Enzymol., 1996; 272:35-44.
Gussow, D. & Clackson, T., Nucleic Acids Res., 1989; 17:4000-4000.
Hamilton et al., J. Am. Chem. Soc., 1978; 100(6):1899-1912.
Hamilton, G.A., de Jersey, J., and Adolf, P.K. (1973) Galactose oxidase : The complexities of a simple enzyme., in King, T.E., et al. Eds., Oxidases and related redox enzyme, University Park Press, Baltimore, MD, 103-124.
Haschke, R.H. & Friedhoff, J.M., Biochim. Biophys. Res. Commun., 1978; 80(4):1039-1042.
Helenius, A., Mol. Biol. Cell., 1994; 5:253-265.
Hermes, J. D. et al., Proc. Natl. Acad. Sci. USA, 1990; 87:696.
Ito et al., Methods Enzymol., 1995; 258:235-262.
Ito et al., J. Mol. Biol., 1994; 238:794-814.
Ito et al., Nature, 1991; 350:87-90.
Joo et al., Chem. Biol., 1999; 6:699-706
Joo et al., Nature, 1999; 399:670-673.
Khosla et al., Bio/Technology, 1990; 8:849-853.
Kiba et al., J. Chromatogr., 1989; 463:183-187.
Klibanov et al., Biochem. Biophys. Res. Commun., 1982; 108:804-808.
Knappik, A.; Pluckthun, A, Protein Eng., 1995; 8(1):81-89.
Koroleva et al., Prikl. Biokhim, Mikrobiol., 1983;19(5): 632-637.
Kosman, D.J. (1984) Galactose oxidase., in Lontie, R., Eds., Copper proteins and copper enzymes. vol. 2., CRC Press, Boca Raton, Fla., 1-26.
Koster et al., Synthesis, 1982; 650-652.
Kuchner, O., and Arnold, F.H., Trends Biotechnol., 1997; 15:523-530.
Lei et al., J. Bacteriol., 1987; 169:4379.
Liu et al., J. Am. Chem. Soc., 1999; 121:466-467.
Lis, M., and Kuramitsu, H.K. Antimicrob. Agents Chemother., 1997; 41(5):999-1003.
Leung, D. W. et al., Technique, 1989; 1(1):11-15.
Mannino et al., Italian Journal of Food Science, 1999; 11:57-65.
Maradufu et al., Carbohydr. Res., 1974; 32:93-99.
Maradufu et al., Canad. J. Chem., 1971; 49:3429-3436.
Marrs, B, L, IBC's Fifth Annual World Congress on Enzyme Technologies, Mar. 1, 2000.
Martin, I. G., Macias, E. M., Sanchez, J. S., and Rivera, B. G. (1998) Food Chemistry 61, 281-286.
Martin, B.D., Linhardt, R. J., and Dordick, J.S. (1998) Highly swelling hydrogels from ordered galactose-based polyacrylates., Biomaterials, 19(1-3), 69-76.
Martineau, P. et al., J. Mol. Biol., 1998; 20:117-127.
Mazur, A. W., and Hiler, G. D., J. Org. Chem., 1997; 62:4471-4475.
Mazur, A. in Enzymes in Carbohydrate Synthesis (1991) Bednarski, M. D. and Simon, E. S. Eds. pp. 99-110.
McPherson, M.J., Stevens, C., Baron, A.J., Ogel, Z.B., Seneviratne, K., Wilmot, C., Ito, N., Brocklebank, I., Phillips, S.E.V., and Knowles, P.F. (1993) Galactose oxidase: Molecular analysis and mutagenesis studies., Biochem. Soc. Transact., 21:752-756.
McPherson, M.J., et al. J. Biol. Chem., 1992; 267(12):8146-8152.
Mendonca, M.H., and Zancan, G.T., Arch. Biochem, Biophys., 1988; 266(2):427-434.
Mendonca, M. H., and Zancan, G. T. Arch. Biochem. Biophys., 1987; 252(2):507-514.
Miele, R.G., et al. J.Biol.Chem., 1999; 274 7769-7776
Minshull and Stemmer, Curr. Opin. Chem. Biol., 1999; 2:284-290.
Mitraki, A.; King, J. FEBS Lett., 1992; 307(1):20-25.
Miyazaki, K., et al., J.Mol.Biol., 2000; 297:1015-26.
Moore, J.C., et al., J. Mol. Biol., 1997; 272 336-347.
Moore, J. C., et al., Nature Biotechnol., 1996; 14:458.
Nagayama, Y., et al., J. Biol. Chem., 1998; 273:33423-33428.
Nakagawa, S., et al., Biosci. Biotech. Biochem., 1996; 60(3):415-420.
Ness et al., Nature Biotechnol., 1999; 17:893-896.
Oliphant, A. R. et al., Gene, 1986; 44:177-183.
Ortlepp, S. A., et al., J. Biotechnol., 1989; 11:353-364.

Ostermeier, M., et al., Eukaryotic J. Biol. Chem., 1996; 271:10616.
Parekh, R., et al., Protein Expres. Purif., 1995; 6:537-545.
Patten et al., Curr. Opin. Biotechnol., 1997; 8:724-733.
Rathore, D., et al., FEBS Lett., 1996; 392:259-262.
Reynolds, M. P., et al., J. Biol. Inorg. Chem., 1997; 2:327-335.
Rodriguez-Lopez, J.N., et al., J.Biol.Chem , 1995; 271:4023-4030.
Romanos, M.A., et al., Yeast, 1992; 8:423-488.
Root, R. L., et al., J. Am. Chem. Soc., 1985; 107:2997-2999.
Said, I. T., et al., Histol. Histopathol., 1999; 14:351-357.
Savenkova, M. I., et al., Biochemistry, 1998; 37:10828-10836.
Saysell, C.G., et al., JBIC, 1997; 2:702-709.
Schatz, P.J., et al., Annu. Rev. Genet., 1990; 24:215-248.
Schein, C. H., Bio/Technology, 1990; 8:308-317.
Schlegel, R.A., Carbohydr. Res., 1968; 7:193-199.
Shafikhani, S., et al., Biotechniques, 1997, 23(2):304-310.
Shao, Z.X., et al., Nucleic Acids Res., 1998; 26:681-683.
Shindler, J. S.; Childs, R. E.; Bardsley, W. G. Eur, J. Biochem, 65, 325 (1976)
Sirotkin, K. J. Theor. Biol. 123, 261 (1986).
Smith, A.T., & Veitch, N.C. (1998) Curr.Opin.Chem.Biol., 2:269-278.
Smith, A. T., et al., J. Biol. Chem., 1990; 265:13335-13343.
Stemmer, W.P.C., Nature, 1994; 370:389-391.
Stemmer, W. P. C., Proc. Natl. Acad. Sci. USA, 1994; 91:10747-10751.
Stemmer, W. P .C., et al., Biotechniques, 1993; 14(2):256-265.
Studier, F. W., et al., Meth. Enzymol., 1990; 185:60.
Szabo, E. E., et al., Biosensors & Bioelectronics, 1996; 11:1051-1058.
Tams, J. W., et al., FEBS Lett., 1998; 421.234-236.
Thatcher, D. R.; Hitchcock, A. Protein Folding in Biotechnology. In *Mechanisms of Protein Folding*; Pain, R. H., Ed.; IRL Press: Oxford p. 229-261 (1994).
Tkac, J., et al., Biotechnology Techniques, 1999; 13:931-936.
Tressel, P.S., et al., Methods Enzymol., 1989; 89:163-171.
Tressel, P., et al., Anal. Biochem., 1980; 105:150-153.
Tressel, P.S, "Chemical, Kinetic, and Spectral Properties of the Catalytic Mechanism of Galactose Oxidase," Thesis, State University of New York at Buffalo, Jun. 1980.
Vega, F. A., et al., Anal. Chim. Acta, 1998; 373:57-62.

Vrbova, E., Peckova, J., and Marek, M. (1992) Collection of Czechoslovak Chemical Communications 57, 2287-2294.
Wachter, R. M., and Branchaud, B. L., J. Am. Chem. Soc., 1996; 118:2782-2789.
Welinder, K. G., Eur J. Biochem, 1979; 96:483-502.
Wetzel, R., et al., Bio/Technology, 1991; 9:731.
Whittaker, M.M., et al., Biochemistry, 1998; 37:8426-8436.
Whitaker, M. W., et al., J. Biol. Chem., 1988; 263:6074-6080.
Yang, G. Y., and Shamsuddin, A. M., Histol. Histopathol., 1996; 11:801-806.
Yano, T., et al., Proc. Natl. Acad. Sci. USA , 1998; 95:5511-5515.
You, L., and Arnold, F.H., Protein Eng., 1996; 9:77-83.
Zhang, J.H., et al., Proc. Natl. Acad. Sci. USA, 1997; 94:4504-4509.
Zhang, J. X.; Goldenberg, D. P., Biochemistry, 1993;32:14075.
Zhao, H M. & Arnold, F. H., Protein Eng., 1999; 12:47-53.
Zhao, H M., et al., Nature Biotechnol., 1998; 16:258-261.
Zhao, H M.; Arnold, F. H., Nucleic Acids Res., 1997; 25:1307.
Zhao H., and Arnold, F.H. , Nucleic acids Res., 1997; 25(6):1307-1308.
Zhao, H , and Arnold, F.H., PNAS. USA, 1997; 94:7997-800.
XP-002298547 Database accession No. M86819, Mar. 4, 2000.
XP-002298548 Database Registry, Chemical Abstracts Service, Database accession No. 355884-87-6.
Sun, Llanhong, et al., "Expression and stabilization of galactose oxidase in *Escherichia coli* by directed evolution", Protein Engineering, Sep. 2001, vol. 14, No. 9, pp. 699-704.
Sun Lianhong, et al., "Modification of Galactose Oxidase to Introduce Glucose 6-Oxidase Activity", Chembiochem: A European Journal of Chemical Biology, Aug. 2, 2002, vol. 3, No. 8, pp. 781-783.
Deacon, Sarah E., et al., "Enhanced Fructose Oxidase Activity in a Galactose Oxidase Variant", Chembiochem: A European Journal of Chemical Biology, vol. 5, No. 7, Jul. 5, 2004, pp. 972-979.
Wilkinson, D., et al., "Structural and kinetic studies of a series of mutants of galactose oxidase identified by directed evolution", Protein Engineering, Design & Selection, vol. 17, No. 2, 2004, pp. 141-148.

* cited by examiner

FIG. 6

| PCR primers | | Sequence | |
|---|---|---|---|
| MY | | | |
| | 001 | 5'-AAT TCG AAG CTT ATG GCC TCA GCA CCT ATC GGA AGC-3' | SEQ. ID NO 1 |
| | 002 | 5'-CTT CCT TCT AGA TTA CTG AGT AAC GCG AAT CGT-3' | SEQ. ID NO 2 |
| | 003 | 5'-GGA AGA GAA TTC AAT ACG CAA ACC GCC TCT-3' | SEQ. ID NO 3 |
| | 004 | 5'-GGT CAT AAG CTT TTC CTG TGT GAA ATT GTT AT-3' | SEQ. ID NO 4 |
| | 005 | 5'-ACC ATG ATT TCG ACG TCG GTA CCC TCA GCA-3' | SEQ. ID NO. 5 |
| | 009 | 5'-CTT CCT AAG CTT TCA CTG AGT AAC GCG AAT-3' | SEQ. ID NO 6 |
| | 036 | 5'-GGA AGA GGT ACC AAT ACG CAA ACC GCC TCT-3' | SEQ. ID NO. 7 |

FIG. 11

| Plasmid | (vector) | | GAO activities [units/ml-culture] | | | |
|---|---|---|---|---|---|---|
| | | Host strain | DH5αMCR | BL21(DE3) | | KY-14478 |
| | | Induction | | IPTG | IPTG | IPTG |
| pR3 | (pUC118) | | 0 | 0.01 | 0.01 | 0.03 | 0.31 |
| pGAO-003 | (pET22b(+)) | | 0 | 0 | 0 | 0 | 0 |
| pGAO-004 | (pET22b(+)) | | 0 | 0 | 0 | 0 | 0 |
| pGAO-005 | (pET22b(+)) | | 0 | 0 | 0 | 0 | 0 |
| pGAO-006 | (pUC118) | | 1.22 | 1.72 | 0.08 | 1.35 | 0.87 |
| pGAO-007 | (pET22b(+)) | | 0.02 | 0 | 0.05 | 0 | 0 |
| pGAO-008 | (pET22b(+)) | | 0 | 0 | 0.03 | 0.01 | 0 |
| pGAO-009 | (pET22b(+)) | | 0 | 0 | 0.02 | 0.03 | 0 |
| pGAO-010 | (pUC18) | | 0 | 0 | 0.67 | 1.43 | 0.40 |
| pGAO-011 | (pUC18) | | 0.04 | 0.04 | 0.01 | 0.85 | 0.41 |
| pGAO-014 | (pUC18) | | 0 | 0.01 | -** | -** | 0 |
| pGAO-015 | (pUC18) | | 0 | 0 | -** | -** | 0 |
| pGAO-016 | (pUC18) | | 0.19 | 0.15 | 0.03 | 0.04 | 0 |
| pGAO-017 | (pUC18) | | 0 | 0 | 0.06 | 0.47 | 0.31 |
| pGAO-018 | (pUC18) | | -* | -* | -** | -** | -** |
| pGAO-019 | (pUC18) | | -* | -* | -** | -** | -** |
| pGAO-020 | (pUC18) | | 0 | 0.01 | 0.97 | 2.21 | 0.22 |
| pGAO-021 | (pUC18) | | 0.02 | 0 | 0.03 | 0.31 | 0.24 |
| pGAO-022 | (pUC18) | | 0.03 | 0.08 | 0.12 | 0.93 | 0.14 |
| pGAO-023 | (pUC18) | | -* | -* | -** | -** | -* |
| pGAO-024 | (pUC18) | | -* | -* | -** | -** | -* |

| Plasmid | | GAO activity [units/ml] (+ IPTG) | |
|---|---|---|---|
| | | BL21(DE3) | KY-14478 |
| pGAO-011 (pUC18) | | 0.28 | 0.74 |
| pGAO-025 (pUC18) | | 0.91 | 0.88 |
| pGAO-010 (pUC18) | | 3.32 | 1.20 |
| pGAO-027 (pUC18) | | 3.64 | 1.57 |
| pGAO-028 (pUC18) | | 2.97 | 1.77 |

FIG. 15

| Substrate (100 mM) | Rearative activities of galactose oxidase [%] | |
|---|---|---|
| | *D. dendroides* (Sigma) | *E. coli* BL21(DE3)/pGAO-010 |
| D-Galactose | 100 | 100 |
| D-Glucose | 0 | 0 |
| D-Sucrose | 0 | 0 |
| α-D-Lactose | 20 | 17 |
| β-D-Lactose | 42 | 32 |
| D-Raffinose | 114 | 110 |
| D-Melibiose | 75 | 75 |
| Benzyl alcohol (25 % Methanol) | 15 | 11 |
| 2-Hydroxybenzyl alcohol | (+) | (+) |
| 2-Pyridylcarbinol | 14 | 15 |
| 3-Pyridylcarbinol | 50 | 46 |
| 4-Pyridylcarbinol | 32 | 29 |
| Cyclohexylmethnol (45 % Methanol) 1) | 1.9 | 2.1 |
| Tetrahydropyran-2-methanol 2) | 0 | 0 |
| Cyclopentamethanol (30 % Methanol) 3) | 0.42 | 0.25 |
| Tetrahydrofurfuryl alcohol 4) | n.d. | n.d. |
| Glycerol | 4.1 | 3.4 |
| Ethylene glycol | 0.45 | 0.16 |
| 1-Propanol | 0 | 0 |
| 1,2-Propanediol | (+) | (+) |
| Acetol | 13 | 13 |
| Allyl alcohol | 4.6 | 3.6 |

1) 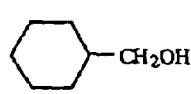  2) 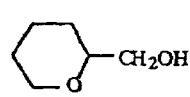  3) 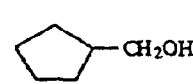  4) 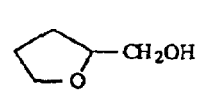

FIG. 17A

```
Date          : 2000.04.10
Mutant ID     : 9.16.8D2
Mutation      : N537D(A1609G)
Sequence Size : 1917
```

```
         10              20              30              40              50              60
GCC TCA GCA CCT ATC GGA AGC GCC ATT TCT CGC AAC AAC TGG GCC GTC ACT TGC GAC AGT
 A   S   A   P   I   G   S   A   I   S   R   N   N   W   A   V   T   C   D   S 70              80              90             100             110             120
GCA CAG TCG GGA AAT GAA TGC AAC AAG GCC ATT GAT GGC AAC AAG GAT ACC TTT TGG CAC
 A   Q   S   G   N   E   C   N   K   A   I   D   G   N   K   D   T   F   W   H 130             140             150             160             170             180
ACA TTC TAT GGC GCC AAC GGG GAT CCA AAG CCC CCT CAC ACA TAC ACG ATT GAC ATG AAG
 T   F   Y   G   A   N   G   D   P   K   P   P   H   T   Y   T   I   D   M   K 190             200             210             220             230             240
ACA ACT CAG AAC GTC AAC GGC TTG TCT ATG CTG CCT CGA CAG GAT GGT AAC CAA AAC GGC
 T   T   Q   N   V   N   G   L   S   M   L   P   R   Q   D   G   N   Q   N   G 250             260             270             280             290             300
TGG ATC GGT CGC CAT GAG GTT TAT CTA AGC TCA GAT GGC ACA AAC TGG GGC AGC CCT GTT
 W   I   G   R   H   E   V   Y   L   S   S   D   G   T   N   W   G   S   P   V 310             320             330             340             350             360
GCG TCA GGT AGT TGG TTC GCC GAC TCT ACT ACA AAA TAC TCC AAC TTT GAA ACT CGC CCT
 A   S   G   S   W   F   A   D   S   T   T   K   Y   S   N   F   E   T   R   P 370             380             390             400             410             420
GCT CGC TAT GTT CGT CTT GTC GCT ATC ACT GAA GCG AAT GGC CAG CCT TGG ACT AGC ATT
 A   R   Y   V   R   L   V   A   I   T   E   A   N   G   Q   P   W   T   S   I 430             440             450             460             470             480
GCA GAG ATC AAC GTC TTC CAA GCT AGT TCT TAC ACA GCC CCC CAG CCT GGT CTT GGA CGC
 A   E   I   N   V   F   Q   A   S   S   Y   T   A   P   Q   P   G   L   G   R 490             500             510             520             530             540
TGG GGT CCG ACT ATT GAC TTA CCG ATT GTT CCT GCG GCT GCA GCA ATT GAA CCG ACA TCG
 W   G   P   T   I   D   L   P   I   V   P   A   A   A   A   I   E   P   T   S 550             560             570             580             590             600
GGA CGA GTC CTT ATG TGG TCT TCA TAT CGC AAT GAT GCA TTT GGA GGA TCC CCT GGT GGT
 G   R   V   L   M   W   S   S   Y   R   N   D   A   F   G   G   S   P   G   G 610             620             630             640             650             660
ATC ACT TTG ACG TCT TCC TGG GAT CCA TCC ACT GGT ATT GTT TCC GAC CGC ACT GTG ACA
 I   T   L   T   S   S   W   D   P   S   T   G   I   V   S   D   R   T   V   T 670             680             690             700             710             720
GTC ACC AAG CAT GAT ATG TTC TGC CCT GGT ATC TCC ATG GAT GGT AAC GGT CAG ATC GTA
 V   T   K   H   D   M   F   C   P   G   I   S   M   D   G   N   G   Q   I   V 730             740             750             760             770             780
GTC ACA GGT GGC AAC GAT GCC AAG AAG ACC AGT TTG TAT GAT TCA TCT AGC GAT AGC TGG
 V   T   G   G   N   D   A   K   K   T   S   L   Y   D   S   S   S   D   S   W 790             800             810             820             830             840
ATC CCG GGA CCT GAC ATG CAA GTG GCT CGT GGG TAT CAG TCA TCA GCT ACC ATG TCA GAC
 I   P   G   P   D   M   Q   V   A   R   G   Y   Q   S   S   A   T   M   S   D
```

FIG. 17B

```
          850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GTC TAC CAT AGC ATT TCC CTT
 D   T   F   Y   K   Q   N   P   N   S   I   V   R   V   Y   H   S   I   S   L 1510        1520        1530        1540        1550        1560
TTG TTA CCT GAT GGC AGG GTA TTT AAC GGT GGT GGT CTT TGT GGC GAT TGT ACC ACG
 L   L   P   D   G   R   V   F   N   G   G   G   L   C   G   D   C   T   T 1570        1580        1590        1600        1610        1620
AAT CAT TTC GAC GCG CAA ATC TTT ACG CCA AAC TAT CTT TAC AAT AGC GAC GGC AAT CTC
 N   H   F   D   A   Q   I   F   T   P   N   Y   L   Y   N   S   D   G   N   L 1630        1640        1650        1660        1670        1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T
```

```
        1750            1760            1770            1780           1790  .         1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N 1810            1820            1830            1840            1850            1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870            1880            1890            1900            1910            1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 17C

Date        : 2000.04.10
Mutant ID   : 9.16.6C11
Mutation    : V494A(T1481C), C515S(T1543A)
Sequence Size : 1917

FIG. 18A

```
              10           20           30           40           50           60
     GCC TCA GCA CCT ATC GGA AGC GCC ATT TCT CGC AAC AAC TGG GCC GTC ACT TGC GAC AGT
      A   S   A   P   I   G   S   A   I   S   R   N   N   W   A   V   T   C   D   S 70           80           90          100          110          120
     GCA CAG TCG GGA AAT GAA TGC AAC AAG GCC ATT GAT GGC AAC AAG GAT ACC TTT TGG CAC
      A   Q   S   G   N   E   C   N   K   A   I   D   G   N   K   D   T   F   W   H 130          140          150          160          170          180
     ACA TTC TAT GGC GCC AAC GGG GAT CCA AAG CCC CCT CAC ACA TAC ACG ATT GAC ATG AAG
      T   F   Y   G   A   N   G   D   P   K   P   P   H   T   Y   T   I   D   M   K 190          200          210          220          230          240
     ACA ACT CAG AAC GTC AAC GGC TTG TCT ATG CTG CCT CGA CAG GAT GGT AAC CAA AAC GGC
      T   T   Q   N   V   N   G   L   S   M   L   P   R   Q   D   G   N   Q   N   G 250          260          270          280          290          300
     TGG ATC GGT CGC CAT GAG GTT TAT CTA AGC TCA GAT GGC ACA AAC TGG GGC AGC CCT GTT
      W   I   G   R   H   E   V   Y   L   S   S   D   G   T   N   W   G   S   P   V 310          320          330          340          350          360
     GCG TCA GGT AGT TGG TTC GCC GAC TCT ACT ACA AAA TAC TCC AAC TTT GAA ACT CGC CCT
      A   S   G   S   W   F   A   D   S   T   T   K   Y   S   N   F   E   T   R   P 370          380          390          400          410          420
     GCT CGC TAT GTT CGT CTT GTC GCT ATC ACT GAA GCG AAT GGC CAG CCT TGG ACT AGC ATT
      A   R   Y   V   R   L   V   A   I   T   E   A   N   G   Q   P   W   T   S   I 430          440          450          460          470          480
     GCA GAG ATC AAC GTC TTC CAA GCT AGT TCT TAC ACA GCC CCC CAG CCT GGT CTT GGA CGC
      A   E   I   N   V   F   Q   A   S   S   Y   T   A   P   Q   P   G   L   G   R 490          500          510          520          530          540
     TGG GGT CCG ACT ATT GAC TTA CCG ATT GTT CCT GCG GCT GCA GCA ATT GAA CCG ACA TCG
      W   G   P   T   I   D   L   P   I   V   P   A   A   A   A   I   E   P   T   S 550          560          570          580          590          600
     GGA CGA GTC CTT ATG TGG TCT TCA TAT CGC AAT GAT GCA TTT GGA GGA TCC CCT GGT GGT
      G   R   V   L   M   W   S   S   Y   R   N   D   A   F   G   G   S   P   G   G 610          620          630          640          650          660
     ATC ACT TTG ACG TCT TCC TGG GAT CCA TCC ACT GGT ATT GTT TCC GAC CGC ACT GTG ACA
      I   T   L   T   S   S   W   D   P   S   T   G   I   V   S   D   R   T   V   T 670          680          690          700          710          720
     GTC ACC AAG CAT GAT ATG TTC TGC CCT GGT ATC TCC ATG GAT GGT AAC GGT CAG ATC GTA
      V   T   K   H   D   M   F   C   P   G   I   S   M   D   G   N   G   Q   I   V 730          740          750          760          770          780
     GTC ACA GGT GGC AAC GAT GCC AAG AAG ACC AGT TTG TAT GAT TCA TCT AGC GAT AGC TGG
      V   T   G   G   N   D   A   K   K   T   S   L   Y   D   S   S   S   D   S   W 790          800          810          820          830          840
     ATC CCG GGA CCT GAC ATG CAA GTG GCT CGT GGG TAT CAG TCA TCA GCT ACC ATG TCA GAC
      I   P   G   P   D   M   Q   V   A   R   G   Y   Q   S   S   A   T   M   S   D
```

FIG. 18B

```
         850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510        1520        1530        1540        1550        1560
TTG TTA CCT GAT GGC AGG GTA TTT AAC GGT GGT GGT GGT CTT AGT GGC GAT TGT ACC ACG
 L   L   P   D   G   R   V   F   N   G   G   G   G   L   S   G   D   C   T   T 1570        1580        1590        1600        1610        1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630        1640        1650        1660        1670        1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
        1810          1820          1830          1840          1850          1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L
        1870          1880          1890          1900          1910          1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 18C

Date        : 2000.04.10
Mutant ID   : 9.16.16D12
Mutation    : P136(T408C), V494A(T1481C)
Sequence Size : 1917

FIG. 19A

```
            10          20          30          40          50          60
   GCC TCA GCA CCT ATC GGA AGC GCC ATT TCT CGC AAC AAC TGG GCC GTC ACT TGC GAC AGT
    A   S   A   P   I   G   S   A   I   S   R   N   N   W   A   V   T   C   D   S 70          80          90         100         110         120
   GCA CAG TCG GGA AAT GAA TGC AAC AAG GCC ATT GAT GGC AAC AAG GAT ACC TTT TGG CAC
    A   Q   S   G   N   E   C   N   K   A   I   D   G   N   K   D   T   F   W   H 130         140         150         160         170         180
   ACA TTC TAT GGC GCC AAC GGG GAT CCA AAG CCC CCT CAC ACA TAC ACG ATT GAC ATG AAG
    T   F   Y   G   A   N   G   D   P   K   P   P   H   T   Y   T   I   D   M   K 190         200         210         220         230         240
   ACA ACT CAG AAC GTC AAC GGC TTG TCT ATG CTG CCT CGA CAG GAT GGT AAC CAA AAC GGC
    T   T   Q   N   V   N   G   L   S   M   L   P   R   Q   D   G   N   Q   N   G 250         260         270         280         290         300
   TGG ATC GGT CGC CAT GAG GTT TAT CTA AGC TCA GAT GGC ACA AAC TGG GGC AGC CCT GTT
    W   I   G   R   H   E   V   Y   L   S   S   D   G   T   N   W   G   S   P   V 310         320         330         340         350         360
   GCG TCA GGT AGT TGG TTC GCC GAC TCT ACT ACA AAA TAC TCC AAC TTT GAA ACT CGC CCT
    A   S   G   S   W   F   A   D   S   T   T   K   Y   S   N   F   E   T   R   P 370         380         390         400         410         420
   GCT CGC TAT GTT CGT CTT GTC GCT ATC ACT GAA GCG AAT GGC CAG CCC TGG ACT AGC ATT
    A   R   Y   V   R   L   V   A   I   T   E   A   N   G   Q   P   W   T   S   I 430         440         450         460         470         480
   GCA GAG ATC AAC GTC TTC CAA GCT AGT TCT TAC ACA GCC CCC CAG CCT GGT CTT GGA CGC
    A   E   I   N   V   F   Q   A   S   S   Y   T   A   P   Q   P   G   L   G   R 490         500         510         520         530         540
   TGG GGT CCG ACT ATT GAC TTA CCG ATT GTT CCT GCG GCT GCA GCA ATT GAA CCG ACA TCG
    W   G   P   T   I   D   L   P   I   V   P   A   A   A   A   I   E   P   T   S 550         560         570         580         590         600
   GGA CGA GTC CTT ATG TGG TCT TCA TAT CGC AAT GAT GCA TTT GGA GGA TCC CCT GGT GGT
    G   R   V   L   M   W   S   S   Y   R   N   D   A   F   G   G   S   P   G   G 610         620         630         640         650         660
   ATC ACT TTG ACG TCT TCC TGG GAT CCA TCC ACT GGT ATT GTT TCC GAC CGC ACT GTG ACA
    I   T   L   T   S   S   W   D   P   S   T   G   I   V   S   D   R   T   V   T 670         680         690         700         710         720
   GTC ACC AAG CAT GAT ATG TTC TGC CCT GGT ATC TCC ATG GAT GGT AAC GGT CAG ATC GTA
    V   T   K   H   D   M   F   C   P   G   I   S   M   D   G   N   G   Q   I   V 730         740         750         760         770         780
   GTC ACA GGT GGC AAC GAT GCC AAG AAG ACC AGT TTG TAT GAT TCA TCT AGC GAT AGC TGG
    V   T   G   G   N   D   A   K   K   T   S   L   Y   D   S   S   S   D   S   W 790         800         810         820         830         840
   ATC CCG GGA CCT GAC ATG CAA GTG GCT CGT GGG TAT CAG TCA TCA GCT ACC ATG TCA GAC
    I   P   G   P   D   M   Q   V   A   R   G   Y   Q   S   S   A   T   M   S   D
```

FIG. 19B

```
            850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510        1520        1530        1540        1550        1560
TTG TTA CCT GAT GGC AGG GTA TTT AAC GGT GGT GGT GGT CTT TGT GGC GAT TGT ACC ACG
 L   L   P   D   G   R   V   F   N   G   G   G   G   L   C   G   D   C   T   T 1570        1580        1590        1600        1610        1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630        1640        1650        1660        1670        1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
          1810          1820          1830          1840          1850          1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870          1880          1890          1900          1910          1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 19C

Date : 2000.04.13  
Mutant ID : 11.03.6D3  
Mutation : S10P(T28C), P136(T408C), V494A(T1481C)  
Sequence Size : 1917

FIG. 20A

```
                10                  20                  30                  40                  50                  60
       GCC TCA GCA CCT ATC GGA AGC GCC ATT CCT CGC AAC AAC TGG GCC GTC ACT TGC GAC AGT
        A   S   A   P   I   G   S   A   I   P   R   N   N   W   A   V   T   C   D   S 70                  80                  90                 100                 110                 120
       GCA CAG TCG GGA AAT GAA TGC AAC AAG GCC ATT GAT GGC AAC AAG GAT ACC TTT TGG CAC
        A   Q   S   G   N   E   C   N   K   A   I   D   G   N   K   D   T   F   W   H 130                 140                 150                 160                 170                 180
       ACA TTC TAT GGC GCC AAC GGG GAT CCA AAG CCC CCT CAC ACA TAC ACG ATT GAC ATG AAG
        T   F   Y   G   A   N   G   D   P   K   P   P   H   T   Y   T   I   D   M   K 190                 200                 210                 220                 230                 240
       ACA ACT CAG AAC GTC AAC GGC TTG TCT ATG CTG CCT CGA CAG GAT GGT AAC CAA AAC GGC
        T   T   Q   N   V   N   G   L   S   M   L   P   R   Q   D   G   N   Q   N   G 250                 260                 270                 280                 290                 300
       TGG ATC GGT CGC CAT GAG GTT TAT CTA AGC TCA GAT GGC ACA AAC TGG GGC AGC CCT GTT
        W   I   G   R   H   E   V   Y   L   S   S   D   G   T   N   W   G   S   P   V 310                 320                 330                 340                 350                 360
       GCG TCA GGT AGT TGG TTC GCC GAC TCT ACT ACA AAA TAC TCC AAC TTT GAA ACT CGC CCT
        A   S   G   S   W   F   A   D   S   T   T   K   Y   S   N   F   E   T   R   P 370                 380                 390                 400                 410                 420
       GCT CGC TAT GTT CGT CTT GTC GCT ATC ACT GAA GCG AAT GGC CAG CCC TGG ACT AGC ATT
        A   R   Y   V   R   L   V   A   I   T   E   A   N   G   Q   P   W   T   S   I 430                 440                 450                 460                 470                 480
       GCA GAG ATC AAC GTC TTC CAA GCT AGT TCT TAC ACA GCC CCC CAG CCT GGT CTT GGA CGC
        A   E   I   N   V   F   Q   A   S   S   Y   T   A   P   Q   P   G   L   G   R 490                 500                 510                 520                 530                 540
       TGG GGT CCG ACT ATT GAC TTA CCG ATT GTT CCT GCG GCT GCA GCA ATT GAA CCG ACA TCG
        W   G   P   T   I   D   L   P   I   V   P   A   A   A   I   E   P   T   S 550                 560                 570                 580                 590                 600
       GGA CGA GTC CTT ATG TGG TCT TCA TAT CGC AAT GAT GCA TTT GGA GGA TCC CCT GGT GGT
        G   R   V   L   M   W   S   S   Y   R   N   D   A   F   G   G   S   P   G   G 610                 620                 630                 640                 650                 660
       ATC ACT TTG ACG TCT TCC TGG GAT CCA TCC ACT GGT ATT GTT TCC GAC CGC ACT GTG ACA
        I   T   L   T   S   S   W   D   P   S   T   G   I   V   S   D   R   T   V   T 670                 680                 690                 700                 710                 720
       GTC ACC AAG CAT GAT ATG TTC TGC CCT GGT ATC TCC ATG GAT GGT AAC GGT CAG ATC GTA
        V   T   K   H   D   M   F   C   P   G   I   S   M   D   G   N   G   Q   I   V 730                 740                 750                 760                 770                 780
       GTC ACA GGT GGC AAC GAT GCC AAG AAG ACC AGT TTG TAT GAT TCA TCT AGC GAT AGC TGG
        V   T   G   G   N   D   A   K   K   T   S   L   Y   D   S   S   S   D   S   W 790                 800                 810                 820                 830                 840
       ATC CCG GGA CCT GAC ATG CAA GTG GCT CGT GGG TAT CAG TCA TCA GCT ACC ATG TCA GAC
        I   P   G   P   D   M   Q   V   A   R   G   Y   Q   S   S   A   T   M   S   D
```

FIG. 20B

```
         850           860           870           880           890           900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910           920           930           940           950           960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970           980           990          1000          1010          1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030          1040          1050          1060          1070          1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090          1100          1110          1120          1130          1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150          1160          1170          1180          1190          1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210          1220          1230          1240          1250          1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270          1280          1290          1300          1310          1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330          1340          1350          1360          1370          1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390          1400          1410          1420          1430          1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450          1460          1470          1480          1490          1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510          1520          1530          1540          1550          1560
TTG TTA CCT GAT GGC AGG GTA TTT AAC GGT GGT GGT CTT TGT GGC GAT TGT ACC ACG
 L   L   P   D   G   R   V   F   N   G   G   G   L   C   G   D   C   T   T 1570          1580          1590          1600          1610          1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630          1640          1650          1660          1670          1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690          1700          1710          1720          1730          1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750          1760          1770          1780          1790          1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
        1810          1820          1830          1840          1850          1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870          1880          1890          1900          1910          1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 20C

```
Date          : 2000.04.10
Mutant ID     : 11.03.10C3
Mutation      : A3(A9C),P136(T408C),G195E(G584A),V494A(T1481C)
Sequence Size : 1917
```

FIG. 21A

```
            10          20          30          40          50          60
GCC TCA GCC CCT ATC GGA AGC GCC ATT TCT CGC AAC AAC TGG GCC GTC ACT TGC GAC AGT
 A   S   A   P   I   G   S   A   I   S   R   N   N   W   A   V   T   C   D   S 70          80          90         100         110         120
GCA CAG TCG GGA AAT GAA TGC AAC AAG GCC ATT GAT GGC AAC AAG GAT ACC TTT TGG CAC
 A   Q   S   G   N   E   C   N   K   A   I   D   G   N   K   D   T   F   W   H 130         140         150         160         170         180
ACA TTC TAT GGC GCC AAC GGG GAT CCA AAG CCC CCT CAC ACA TAC ACG ATT GAC ATG AAG
 T   F   Y   G   A   N   G   D   P   K   P   P   H   T   Y   T   I   D   M   K 190         200         210         220         230         240
ACA ACT CAG AAC GTC AAC GGC TTG TCT ATG CTG CCT CGA CAG GAT GGT AAC CAA AAC GGC
 T   T   Q   N   V   N   G   L   S   M   L   P   R   Q   D   G   N   Q   N   G 250         260         270         280         290         300
TGG ATC GGT CGC CAT GAG GTT TAT CTA AGC TCA GAT GGC ACA AAC TGG GGC AGC CCT GTT
 W   I   G   R   H   E   V   Y   L   S   S   D   G   T   N   W   G   S   P   V 310         320         330         340         350         360
GCG TCA GGT AGT TGG TTC GCC GAC TCT ACT ACA AAA TAC TCC AAC TTT GAA ACT CGC CCT
 A   S   G   S   W   F   A   D   S   T   T   K   Y   S   N   F   E   T   R   P 370         380         390         400         410         420
GCT CGC TAT GTT CGT CTT GTC GCT ATC ACT GAA GCG AAT GGC CAG CCC TGG ACT AGC ATT
 A   R   Y   V   R   L   V   A   I   T   E   A   N   G   Q   P   W   T   S   I 430         440         450         460         470         480
GCA GAG ATC AAC GTC TTC CAA GCT AGT TCT TAC ACA GCC CCC CAG CCT GGT CTT GGA CGC
 A   E   I   N   V   F   Q   A   S   S   Y   T   A   P   Q   P   G   L   G   R 490         500         510         520         530         540
TGG GGT CCG ACT ATT GAC TTA CCG ATT GTT CCT GCG GCT GCA GCA ATT GAA CCG ACA TCG
 W   G   P   T   I   D   L   P   I   V   P   A   A   A   A   I   E   P   T   S 550         560         570         580         590         600
GGA CGA GTC CTT ATG TGG TCT TCA TAT CGC AAT GAT GCA TTT GAA GGA TCC CCT GGT GGT
 G   R   V   L   M   W   S   S   Y   R   N   D   A   F   E   G   S   P   G   G 610         620         630         640         650         660
ATC ACT TTG ACG TCT TCC TGG GAT CCA TCC ACT GGT ATT GTT TCC GAC CGC ACT GTG ACA
 I   T   L   T   S   S   W   D   P   S   T   G   I   V   S   D   R   T   V   T 670         680         690         700         710         720
GTC ACC AAG CAT GAT ATG TTC TGC CCT GGT ATC TCC ATG GAT GGT AAC GGT CAG ATC GTA
 V   T   K   H   D   M   F   C   P   G   I   S   M   D   G   N   G   Q   I   V 730         740         750         760         770         780
GTC ACA GGT GGC AAC GAT GCC AAG AAG ACC AGT TTG TAT GAT TCA TCT AGC GAT AGC TGG
 V   T   G   G   N   D   A   K   K   T   S   L   Y   D   S   S   S   D   S   W 790         800         810         820         830         840
ATC CCG GGA CCT GAC ATG CAA GTG GCT CGT GGG TAT CAG TCA TCA GCT ACC ATG TCA GAC
 I   P   G   P   D   M   Q   V   A   R   G   Y   Q   S   S   A   T   M   S   D
```

FIG. 21B

```
            850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510        1520        1530        1540        1550        1560
TTG TTA CCT GAT GGC AGG GTA TTT AAC GGT GGT GGT GGT CTT TGT GGC GAT TGT ACC ACG
 L   L   P   D   G   R   V   F   N   G   G   G   G   L   C   G   D   C   T   T 1570        1580        1590        1600        1610        1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630        1640        1650        1660        1670        1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
      1810           1820           1830           1840           1850           1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870           1880           1890           1900           1910           1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

```
Date           : 2000.04.10
Mutant ID      : 11.03.10D6
Mutation       : P136(T408C), T218(T654C), L312(A936G), V494A(T1481C), N535D(A1603G)
Sequence Size  : 1917
```

```
              10              20              30              40              50              60
    GCC TCA GCA CCT ATC GGA AGC GCC ATT TCT CGC AAC AAC TGG GCC GTC ACT TGC GAC AGT
     A   S   A   P   I   G   S   A   I   S   R   N   N   W   A   V   T   C   D   S 70              80              90             100             110             120
    GCA CAG TCG GGA AAT GAA TGC AAC AAG GCC ATT GAT GGC AAC AAG GAT ACC TTT TGG CAC
     A   Q   S   G   N   E   C   N   K   A   I   D   G   N   K   D   T   F   W   H 130             140             150             160             170             180
    ACA TTC TAT GGC GCC AAC GGG GAT CCA AAG CCC CCT CAC ACA TAC ACG ATT GAC ATG AAG
     T   F   Y   G   A   N   G   D   P   K   P   P   H   T   Y   T   I   D   M   K 190             200             210             220             230             240
    ACA ACT CAG AAC GTC AAC GGC TTG TCT ATG CTG CCT CGA CAG GAT GGT AAC CAA AAC GGC
     T   T   Q   N   V   N   G   L   S   M   L   P   R   Q   D   G   N   Q   N   G 250             260             270             280             290             300
    TGG ATC GGT CGC CAT GAG GTT TAT CTA AGC TCA GAT GGC ACA AAC TGG GGC AGC CCT GTT
     W   I   G   R   H   E   V   Y   L   S   S   D   G   T   N   W   G   S   P   V 310             320             330             340             350             360
    GCG TCA GGT AGT TGG TTC GCC GAC TCT ACT ACA AAA TAC TCC AAC TTT GAA ACT CGC CCT
     A   S   G   S   W   F   A   D   S   T   T   K   Y   S   N   F   E   T   R   P 370             380             390             400             410             420
    GCT CGC TAT GTT CGT CTT GTC GCT ATC ACT GAA GCG AAT GGC CAG CCC TGG ACT AGC ATT
     A   R   Y   V   R   L   V   A   I   T   E   A   N   G   Q   P   W   T   S   I 430             440             450             460             470             480
    GCA GAG ATC AAC GTC TTC CAA GCT AGT TCT TAC ACA GCC CCC CAG CCT GGT CTT GGA CGC
     A   E   I   N   V   F   Q   A   S   S   Y   T   A   P   Q   P   G   L   G   R 490             500             510             520             530             540
    TGG GGT CCG ACT ATT GAC TTA CCG ATT GTT CCT GCG GCT GCA GCA ATT GAA CCG ACA TCG
     W   G   P   T   I   D   L   P   I   V   P   A   A   A   A   I   E   P   T   S 550             560             570             580             590             600
    GGA CGA GTC CTT ATG TGG TCT TCA TAT CGC AAT GAT GCA TTT GGA GGA TCC CCT GGT GGT
     G   R   V   L   M   W   S   S   Y   R   N   D   A   F   G   G   S   P   G   G 610             620             630             640             650             660
    ATC ACT TTG ACG TCT TCC TGG GAT CCA TCC ACT GGT ATT GTT TCC GAC CGC ACC GTG ACA
     I   T   L   T   S   S   W   D   P   S   T   G   I   V   S   D   R   T   V   T 670             680             690             700             710             720
    GTC ACC AAG CAT GAT ATG TTC TGC CCT GGT ATC TCC ATG GAT GGT AAC GGT CAG ATC GTA
     V   T   K   H   D   M   F   C   P   G   I   S   M   D   G   N   G   Q   I   V 730             740             750             760             770             780
    GTC ACA GGT GGC AAC GAT GCC AAG AAG ACC AGT TTG TAT GAT TCA TCT AGC GAT AGC TGG
     V   T   G   G   N   D   A   K   K   T   S   L   Y   D   S   S   S   D   S   W 790             800             810             820             830             840
    ATC CCG GGA CCT GAC ATG CAA GTG GCT CGT GGG TAT CAG TCA TCA GCT ACC ATG TCA GAC
     I   P   G   P   D   M   Q   V   A   R   G   Y   Q   S   S   A   T   M   S   D
```

FIG. 22B

```
              850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTG CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510        1520        1530        1540        1550        1560
TTG TTA CCT GAT GGC AGG GTA TTT AAC GGT GGT GGT CTT TGT GGC GAT TGT ACC ACG
 L   L   P   D   G   R   V   F   N   G   G   G   L   C   G   D   C   T   T 1570        1580        1590        1600        1610        1620
AAT CAT TTC GAC GCG CAA ATC TTT ACG CCA AAC TAT CTT TAC GAT AGC AAC GGC AAT CTC
 N   H   F   D   A   Q   I   F   T   P   N   Y   L   Y   D   S   N   G   N   L 1630        1640        1650        1660        1670        1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
        1810            1820            1830            1840            1850            1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870            1880            1890            1900            1910            1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 22C

Date       : 2000.04.10
Mutan ID   : 11.03.13E12
Mutation   : M70V(A208G), P136(T408C), V494A(T1481C)
Sequence Size : 1917

FIG. 23A

```
              10          20          30          40          50          60
     GCC TCA GCA CCT ATC GGA AGC GCC ATT TCT CGC AAC AAC TGG GCC GTC ACT TGC GAC AGT
      A   S   A   P   I   G   S   A   I   S   R   N   N   W   A   V   T   C   D   S 70          80          90         100         110         120
     GCA CAG TCG GGA AAT GAA TGC AAC AAG GCC ATT GAT GGC AAC AAG GAT ACC TTT TGG CAC
      A   Q   S   G   N   E   C   N   K   A   I   D   G   N   K   D   T   F   W   H 130         140         150         160         170         180
     ACA TTC TAT GGC GCC AAC GGG GAT CCA AAG CCC CCT CAC ACA TAC ACG ATT GAC ATG AAG
      T   F   Y   G   A   N   G   D   P   K   P   P   H   T   Y   T   I   D   M   K 190         200         210         220         230         240
     ACA ACT CAG AAC GTC AAC GGC TTG TCT GTG CTG CCT CGA CAG GAT GGT AAC CAA AAC GGC
      T   T   Q   N   V   N   G   L   S   V   L   P   R   Q   D   G   N   Q   N   G 250         260         270         280         290         300
     TGG ATC GGT CGC CAT GAG GTT TAT CTA AGC TCA GAT GGC ACA AAC TGG GGC AGC CCT GTT
      W   I   G   R   H   E   V   Y   L   S   S   D   G   T   N   W   G   S   P   V 310         320         330         340         350         360
     GCG TCA GGT AGT TGG TTC GCC GAC TCT ACT ACA AAA TAC TCC AAC TTT GAA ACT CGC CCT
      A   S   G   S   W   F   A   D   S   T   T   K   Y   S   N   F   E   T   R   P 370         380         390         400         410         420
     GCT CGC TAT GTT CGT CTT GTC GCT ATC ACT GAA GCG AAT GGC CAG CCC TGG ACT AGC ATT
      A   R   Y   V   R   L   V   A   I   T   E   A   N   G   Q   P   W   T   S   I 430         440         450         460         470         480
     GCA GAG ATC AAC GTC TTC CAA GCT AGT TCT TAC ACA GCC CCC CAG CCT GGT CTT GGA CGC
      A   E   I   N   V   F   Q   A   S   S   Y   T   A   P   Q   P   G   L   G   R 490         500         510         520         530         540
     TGG GGT CCG ACT ATT GAC TTA CCG ATT GTT CCT GCG GCT GCA GCA ATT GAA CCG ACA TCG
      W   G   P   T   I   D   L   P   I   V   P   A   A   A   I   E   P   T   S 550         560         570         580         590         600
     GGA CGA GTC CTT ATG TGG TCT TCA TAT CGC AAT GAT GCA TTT GGA GGA TCC CCT GGT GGT
      G   R   V   L   M   W   S   S   Y   R   N   D   A   F   G   G   S   P   G   G 610         620         630         640         650         660
     ATC ACT TTG ACG TCT TCC TGG GAT CCA TCC ACT GGT ATT GTT TCC GAC CGC ACT GTG ACA
      I   T   L   T   S   S   W   D   P   S   T   G   I   V   S   D   R   T   V   T 670         680         690         700         710         720
     GTC ACC AAG CAT GAT ATG TTC TGC CCT GGT ATC TCC ATG GAT GGT AAC GGT CAG ATC GTA
      V   T   K   H   D   M   F   C   P   G   I   S   M   D   G   N   G   Q   I   V 730         740         750         760         770         780
     GTC ACA GGT GGC AAC GAT GCC AAG AAG ACC AGT TTG TAT GAT TCA TCT AGC GAT AGC TGG
      V   T   G   G   N   D   A   K   K   T   S   L   Y   D   S   S   S   D   S   W 790         800         810         820         830         840
     ATC CCG GGA CCT GAC ATG CAA GTG GCT CGT GGG TAT CAG TCA TCA GCT ACC ATG TCA GAC
      I   P   G   P   D   M   Q   V   A   R   G   Y   Q   S   S   A   T   M   S   D
```

FIG. 23B

```
           850           860           870           880           890           900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910           920           930           940           950           960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970           980           990          1000          1010          1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030          1040          1050          1060          1070          1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090          1100          1110          1120          1130          1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150          1160          1170          1180          1190          1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210          1220          1230          1240          1250          1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270          1280          1290          1300          1310          1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330          1340          1350          1360          1370          1380
TTT CAC ACC TCT CTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390          1400          1410          1420          1430          1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450          1460          1470          1480          1490          1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510          1520          1530          1540          1550          1560
TTG TTA CCT GAT GGC AGG GTA TTT AAC GGT GGT GGT GGT CTT TGT GGC GAT TGT ACC ACG
 L   L   P   D   G   R   V   F   N   G   G   G   G   L   C   G   D   C   T   T 1570          1580          1590          1600          1610          1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630          1640          1650          1660          1670          1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690          1700          1710          1720          1730          1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750          1760          1770          1780          1790          1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
          1810          1820          1830          1840          1850          1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870          1880          1890          1900          1910          1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

```
Date      : 2000.04.10
Filename  : 1.06.20E7
Mutation  : S10P(T28C),M70V(A208G),P136(T408C),G195E(G584A),V494A(T1481C)
            N535D(A1603G)
Sequence Size : 1917
```

```
              10          20          30          40          50          60
     GCC TCA GCA CCT ATC GGA AGC GCC ATT CCT CGC AAC AAC TGG GCC GTC ACT TGC GAC AGT
      A   S   A   P   I   G   S   A   I   P   R   N   N   W   A   V   T   C   D   S 70          80          90         100         110         120
     GCA CAG TCG GGA AAT GAA TGC AAC AAG GCC ATT GAT GGC AAC AAG GAT ACC TTT TGG CAC
      A   Q   S   G   N   E   C   N   K   A   I   D   G   N   K   D   T   F   W   H 130         140         150         160         170         180
     ACA TTC TAT GGC GCC AAC GGG GAT CCA AAG CCC CCT CAC ACA TAC ACG ATT GAC ATG AAG
      T   F   Y   G   A   N   G   D   P   K   P   P   H   T   Y   T   I   D   M   K 190         200         210         220         230         240
     ACA ACT CAG AAC GTC AAC GGC TTG TCT GTG CTG CCT CGA CAG GAT GGT AAC CAA AAC GGC
      T   T   Q   N   V   N   G   L   S   V   L   P   R   Q   D   G   N   Q   N   G 250         260         270         280         290         300
     TGG ATC GGT CGC CAT GAG GTT TAT CTA AGC TCA GAT GGC ACA AAC TGG GGC AGC CCT GTT
      W   I   G   R   H   E   V   Y   L   S   S   D   G   T   N   W   G   S   P   V 310         320         330         340         350         360
     GCG TCA GGT AGT TGG TTC GCC GAC TCT ACT ACA AAA TAC TCC AAC TTT GAA ACT CGC CCT
      A   S   G   S   W   F   A   D   S   T   T   K   Y   S   N   F   E   T   R   P 370         380         390         400         410         420
     GCT CGC TAT GTT CGT CTT GTC GCT ATC ACT GAA GCG AAT GGC CAG CCC TGG ACT AGC ATT
      A   R   Y   V   R   L   V   A   I   T   E   A   N   G   Q   P   W   T   S   I 430         440         450         460         470         480
     GCA GAG ATC AAC GTC TTC CAA GCT AGT TCT TAC ACA GCC CCC CAG CCT GGT CTT GGA CGC
      A   E   I   N   V   F   Q   A   S   S   Y   T   A   P   Q   P   G   L   G   R 490         500         510         520         530         540
     TGG GGT CCG ACT ATT GAC TTA CCG ATT GTT CCT GCG GCT GCA GCA ATT GAA CCG ACA TCG
      W   G   P   T   I   D   L   P   I   V   P   A   A   A   A   I   E   P   T   S 550         560         570         580         590         600
     GGA CGA GTC CTT ATG TGG TCT TCA TAT CGC AAT GAT GCA TTT GAA GGA TCC CCT GGT GGT
      G   R   V   L   M   W   S   S   Y   R   N   D   A   F   E   G   S   P   G   G 610         620         630         640         650         660
     ATC ACT TTG ACG TCT TCC TGG GAT CCA TCC ACT GGT ATT GTT TCC GAC CGC ACT GTG ACA
      I   T   L   T   S   S   W   D   P   S   T   G   I   V   S   D   R   T   V   T 670         680         690         700         710         720
     GTC ACC AAG CAT GAT ATG TTC TGC CCT GGT ATC TCC ATG GAT GGT AAC GGT CAG ATC GTA
      V   T   K   H   D   M   F   C   P   G   I   S   M   D   G   N   G   Q   I   V 730         740         750         760         770         780
     GTC ACA GGT GGC AAC GAT GCC AAG AAG ACC AGT TTG TAT GAT TCA TCT AGC GAT AGC TGG
      V   T   G   G   N   D   A   K   K   T   S   L   Y   D   S   S   S   D   S   W 790         800         810         820         830         840
     ATC CCG GGA CCT GAC ATG CAA GTG GCT CGT GGG TAT CAG TCA TCA GCT ACC ATG TCA GAC
      I   P   G   P   D   M   Q   V   A   R   G   Y   Q   S   S   A   T   M   S   D
```

FIG. 24B

```
        850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC AAC GCC CAC ATC ATC ACC CTC GGT
 G   S   P   D   Y   Q   D   S   D   A   T   T   N   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510        1520        1530        1540        1550        1560
TTG TTA CCT GAT GGC AGG GTA TTT AAC GGT GGT GGT CTT TGT GGC GAT TGT ACC ACG
 L   L   P   D   G   R   V   F   N   G   G   G   L   C   G   D   C   T   T 1570        1580        1590        1600        1610        1620
AAT CAT TTC GAC GCG CAA ATC TTT ACG CCA AAC TAT CTT TAC GAT AGC AAC GGC AAT CTC
 N   H   F   D   A   Q   I   F   T   P   N   Y   L   Y   D   S   N   G   N   L 1630        1640        1650        1660        1670        1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
      1810        1820        1830        1840        1850        1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870        1880        1890        1900        1910        1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 24C

```
Date          : 2000.04.11                                          FIG. 25A
Mutant ID     : 1.D4
Mutation      : N413D(A1237G)
Sequence Size : 1917
```

```
        10          20          30          40          50          60
GCC TCA GCA CCT ATC GGA AGC GCC ATT TCT CGC AAC AAC TGG GCC GTC ACT TGC GAC AGT
 A   S   A   P   I   G   S   A   I   S   R   N   N   W   A   V   T   C   D   S 70          80          90         100         110         120
GCA CAG TCG GGA AAT GAA TGC AAC AAG GCC ATT GAT GGC AAC AAG GAT ACC TTT TGG CAC
 A   Q   S   G   N   E   C   N   K   A   I   D   G   N   K   D   T   F   W   H 130         140         150         160         170         180
ACA TTC TAT GGC GCC AAC GGG GAT CCA AAG CCC CCT CAC ACA TAC ACG ATT GAC ATG AAG
 T   F   Y   G   A   N   G   D   P   K   P   P   H   T   Y   T   I   D   M   K 190         200         210         220         230         240
ACA ACT CAG AAC GTC AAC GGC TTG TCT ATG CTG CCT CGA CAG GAT GGT AAC CAA AAC GGC
 T   T   Q   N   V   N   G   L   S   M   L   P   R   Q   D   G   N   Q   N   G 250         260         270         280         290         300
TGG ATC CGT CGC CAT GAG GTT TAT CTA AGC TCA GAT GGC ACA AAC TGG GGC AGC CCT GTT
 W   I   R   R   H   E   V   Y   L   S   S   D   G   T   N   W   G   S   P   V 310         320         330         340         350         360
GCG TCA GGT AGT TGG TTC GCC GAC TCT ACT ACA AAA TAC TCC AAC TTT GAA ACT CGC CCT
 A   S   G   S   W   F   A   D   S   T   T   K   Y   S   N   F   E   T   R   P 370         380         390         400         410         420
GCT CGC TAT GTT CGT CTT GTC GCT ATC ACT GAA GCG AAT GGC CAG CCT TGG ACT AGC ATT
 A   R   Y   V   R   L   V   A   I   T   E   A   N   G   Q   P   W   T   S   I 430         440         450         460         470         480
GCA GAG ATC AAC GTC TTC CAA GCT AGT TCT TAC ACA GCC CCC CAG CCT GGT CTT GCA CGC
 A   E   I   N   V   F   Q   A   S   S   Y   T   A   P   Q   P   G   L   G   R 490         500         510         520         530         540
TGG GGT CCG ACT ATT GAC TTA CCG ATT GTT CCT GCG GCT GCA GCA ATT GAA CCG ACA TCG
 W   G   P   T   I   D   L   P   I   V   P   A   A   A   A   I   E   P   T   S 550         560         570         580         590         600
GGA CGA GTC CTT ATG TGG TCT TCA TAT CGC AAT GAT GCA TTT GGA GGA TCC CCT GGT GGT
 G   R   V   L   M   W   S   S   Y   R   N   D   A   F   G   G   S   P   G   G 610         620         630         640         650         660
ATC ACT TTG ACG TCT TCC TGG GAT CCA TCC ACT GGT ATT GTT TCC GAC CGC ACT GTG ACA
 I   T   L   T   S   S   W   D   P   S   T   G   I   V   S   D   R   T   V   T 670         680         690         700         710         720
GTC ACC AAG CAT GAT ATG TTC TGC CCT GGT ATC TCC ATG GAT GGT AAC GGT CAG ATC GTA
 V   T   K   H   D   M   F   C   P   G   I   S   M   D   G   N   G   Q   I   V 730         740         750         760         770         780
GTC ACA GGT GGC AAC GAT GCC AAG AAG ACC AGT TTG TAT GAT TCA TCT AGC GAT AGC TGG
 V   T   G   G   N   D   A   K   K   T   S   L   Y   D   S   S   S   D   S   W 790         800         810         820         830         840
ATC CCG GGA CCT GAC ATG CAA GTG GCT CGT GGG TAT CAG TCA TCA GCT ACC ATG TCA GAC
 I   P   G   P   D   M   Q   V   A   R   G   Y   Q   S   S   A   T   M   S   D
```

FIG. 25B

```
          850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC GAC GCC CAC ATC ATC ACC CTC GGT
 G   S   P   D   Y   Q   D   S   D   A   T   T   D   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GTC TAC CAT AGC ATT TCC CTT
 D   T   F   Y   K   Q   N   P   N   S   I   V   R   V   Y   H   S   I   S   L 1510        1520        1530        1540        1550        1560
TTG TTA CCT GAT GGC AGG GTA TTT AAC GGT GGT GGT GGT CTT TGT GGC GAT TGT ACC ACG
 L   L   P   D   G   R   V   F   N   G   G   G   G   L   C   G   D   C   T   T 1570        1580        1590        1600        1610        1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630        1640        1650        1660        1670        1680
GCG ACA CGT CCC AAG ATT ACC AGA ACC TCT ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
      1810          1820          1830          1840          1850          1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870          1880          1890          1900          1910          1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 25C

Date       : 2000.04.11
Mutant ID  : 2.G4
Mutation   : N413D(A1237G),S550(T1650A)
Sequence Size : 1917

FIG. 26A

```
             10              20              30              40              50              60
    GCC TCA GCA CCT ATC GGA AGC GCC ATT TCT CGC AAC AAC TGG GCC GTC ACT TGC GAC AGT
     A   S   A   P   I   G   S   A   I   S   R   N   N   W   A   V   T   C   D   S 70              80              90             100             110             120
    GCA CAG TCG GGA AAT GAA TGC AAC AAG GCC ATT GAT GGC AAC AAG GAT ACC TTT TGG CAC
     A   Q   S   G   N   E   C   N   K   A   I   D   G   N   K   D   T   F   W   H 130             140             150             160             170             180
    ACA TTC TAT GGC GCC AAC GGG GAT CCA AAG CCC CCT CAC ACA TAC ACG ATT GAC ATG AAG
     T   F   Y   G   A   N   G   D   P   K   P   P   H   T   Y   T   I   D   M   K 190             200             210             220             230             240
    ACA ACT CAG AAC GTC AAC GGC TTG TCT ATG CTG CCT CGA CAG GAT GGT AAC CAA AAC GGC
     T   T   Q   N   V   N   G   L   S   M   L   P   R   Q   D   G   N   Q   N   G 250             260             270             280             290             300
    TGG ATC GGT CGC CAT GAG GTT TAT CTA AGC TCA GAT GGC ACA AAC TGG GGC AGC CCT GTT
     W   I   G   R   H   E   V   Y   L   S   S   D   G   T   N   W   G   S   P   V 310             320             330             340             350             360
    GCG TCA GGT AGT TGG TTC GCC GAC TCT ACT ACA AAA TAC TCC AAC TTT GAA ACT CGC CCT
     A   S   G   S   W   F   A   D   S   T   T   K   Y   S   N   F   E   T   R   P 370             380             390             400             410             420
    GCT CGC TAT GTT CGT CTT GTC GCT ATC ACT GAA GCG AAT GGC CAG CCT TGG ACT AGC ATT
     A   R   Y   V   R   L   V   A   I   T   E   A   N   G   Q   P   W   T   S   I 430             440             450             460             470             480
    GCA GAG ATC AAC GTC TTC CAA GCT AGT TCT TAC ACA GCC CCC CAG CCT GGT CTT GGA CGC
     A   E   I   N   V   F   Q   A   S   S   Y   T   A   P   Q   P   G   L   G   R 490             500             510             520             530             540
    TGG GGT CCG ACT ATT GAC TTA CCG ATT GTT CCT GCG GCT GCA GCA ATT GAA CCG ACA TCG
     W   G   P   T   I   D   L   P   I   V   P   A   A   A   A   I   E   P   T   S 550             560             570             580             590             600
    GGA CGA GTC CTT ATG TGG TCT TCA TAT CGC AAT GAT GCA TTT GGA GGA TCC CCT GGT GGT
     G   R   V   L   M   W   S   S   Y   R   N   D   A   F   G   G   S   P   G   G 610             620             630             640             650             660
    ATC ACT TTG ACG TCT TCC TGG GAT CCA TCC ACT GGT ATT GTT TCC GAC CGC ACT GTG ACA
     I   T   L   T   S   S   W   D   P   S   T   G   I   V   S   D   R   T   V   T 670             680             690             700             710             720
    GTC ACC AAG CAT GAT ATG TTC TGC CCT GGT ATC TCC ATG GAT GGT AAC GGT CAG ATC GTA
     V   T   K   H   D   M   F   C   P   G   I   S   M   D   G   N   G   Q   I   V 730             740             750             760             770             780
    GTC ACA GGT GGC AAC GAT GCC AAG AAG ACC AGT TTG TAT GAT TCA TCT AGC GAT AGC TGG
     V   T   G   G   N   D   A   K   K   T   S   L   Y   D   S   S   S   D   S   W 790             800             810             820             830             840
    ATC CCG GGA CCT GAC ATG CAA GTG GCT CGT GGG TAT CAG TCA TCA GCT ACC ATG TCA GAC
     I   P   G   P   D   M   Q   V   A   R   G   Y   Q   S   S   A   T   M   S   D
```

FIG. 26B

```
             850         860         870         880         890         900
    GGT CGT GTT TTT ACC ATT GGA GGC TCC TGG AGC GGT GGC GTA TTT GAG AAG AAT GGC GAA
     G   R   V   F   T   I   G   G   S   W   S   G   G   V   F   E   K   N   G   E 910         920         930         940         950         960
    GTC TAT AGC CCA TCT TCA AAG ACA TGG ACG TCC CTA CCC AAT GCC AAG GTC AAC CCA ATG
     V   Y   S   P   S   S   K   T   W   T   S   L   P   N   A   K   V   N   P   M 970         980         990         1000        1010        1020
    TTG ACG GCT GAC AAG CAA GGA TTG TAC CGT TCA GAC AAC CAC GCG TGG CTC TTT GGA TGG
     L   T   A   D   K   Q   G   L   Y   R   S   D   N   H   A   W   L   F   G   W 1030        1040        1050        1060        1070        1080
    AAG AAG GGT TCG GTG TTC CAA GCG GGA CCT AGC ACA GCC ATG AAC TGG TAC TAT ACC AGT
     K   K   G   S   V   F   Q   A   G   P   S   T   A   M   N   W   Y   Y   T   S 1090        1100        1110        1120        1130        1140
    GGA AGT GGT GAT GTG AAG TCA GCC GGA AAA CGC CAG TCT AAC CGT GGT GTA GCC CCT GAT
     G   S   G   D   V   K   S   A   G   K   R   Q   S   N   R   G   V   A   P   D 1150        1160        1170        1180        1190        1200
    GCC ATG TGC GGA AAC GCT GTC ATG TAC GAC GCC GTT AAA GGA AAG ATC CTG ACC TTT GGC
     A   M   C   G   N   A   V   M   Y   D   A   V   K   G   K   I   L   T   F   G 1210        1220        1230        1240        1250        1260
    GGC TCC CCA GAT TAT CAA GAC TCT GAC GCC ACA ACC GAC GCC CAC ATC ATC ACC CTC GGT
     G   S   P   D   Y   Q   D   S   D   A   T   T   D   A   H   I   I   T   L   G 1270        1280        1290        1300        1310        1320
    GAA CCC GGA ACA TCT CCC AAC ACT GTC TTT GCT AGC AAT GGG TTG TAC TTT GCC CGA ACG
     E   P   G   T   S   P   N   T   V   F   A   S   N   G   L   Y   F   A   R   T 1330        1340        1350        1360        1370        1380
    TTT CAC ACC TCT GTT GTT CTT CCA GAC GGA AGC ACG TTT ATT ACA GGA GGC CAA CGA CGT
     F   H   T   S   V   V   L   P   D   G   S   T   F   I   T   G   G   Q   R   R 1390        1400        1410        1420        1430        1440
    GGA ATT CCG TTC GAG GAT TCA ACC CCG GTA TTT ACA CCT GAG ATC TAC GTC CCT GAA CAA
     G   I   P   F   E   D   S   T   P   V   F   T   P   E   I   Y   V   P   E   Q 1450        1460        1470        1480        1490        1500
    GAC ACT TTC TAC AAG CAG AAC CCC AAC TCC ATT GTT CGC GTC TAC CAT AGC ATT TCC CTT
     D   T   F   Y   K   Q   N   P   N   S   I   V   R   V   Y   H   S   I   S   L 1510        1520        1530        1540        1550        1560
    TTG TTA CCT GAT GGC AGG GTA TTT AAC GGT GGT GGT GGT CTT TGT GGC GAT TGT ACC ACG
     L   L   P   D   G   R   V   F   N   G   G   G   G   L   C   G   D   C   T   T 1570        1580        1590        1600        1610        1620
    AAT CAT TTC GAC GCG CAA ATC TTT ACG CCA AAC TAT CTT TAC AAT AGC AAC GGC AAT CTC
     N   H   F   D   A   Q   I   F   T   P   N   Y   L   Y   N   S   N   G   N   L 1630        1640        1650        1660        1670        1680
    GCG ACA CGT CCC AAG ATT ACC AGA ACC TCA ACA CAG AGC GTC AAG GTC GGT GGC AGA ATT
     A   T   R   P   K   I   T   R   T   S   T   Q   S   V   K   V   G   G   R   I 1690        1700        1710        1720        1730        1740
    ACA ATC TCG ACG GAT TCT TCG ATT AGC AAG GCG TCG TTG ATT CGC TAT GGT ACA GCG ACA
     T   I   S   T   D   S   S   I   S   K   A   S   L   I   R   Y   G   T   A   T 1750        1760        1770        1780        1790        1800
    CAC ACG GTT AAT ACT GAC CAG CGC CGC ATT CCC CTG ACT CTG ACA AAC AAT GGA GGA AAT
     H   T   V   N   T   D   Q   R   R   I   P   L   T   L   T   N   N   G   G   N
```

```
         1810          1820          1830          1840          1850          1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870          1880          1890          1900          1910          1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

```
Date          : 2000 04.11
Mutant ID     : 3.H7
Mutation      : N413D(A1237G),S550(T1650A),V494A(T1481C)
Sequence Size : 1917
```

```
          10            20            30            40            50            60
GCC TCA GCA CCT ATC GGA AGC GCC ATT TCT CGC AAC AAC TGG GCC GTC ACT TGC GAC AGT
 A   S   A   P   I   G   S   A   I   S   R   N   N   W   A   V   T   C   D   S 70            80            90           100           110           120
GCA CAG TCG GGA AAT GAA TGC AAC AAG GCC ATT GAT GGC AAC AAG GAT ACC TTT TGG CAC
 A   Q   S   G   N   E   C   N   K   A   I   D   G   N   K   D   T   F   W   H 130           140           150           160           170           180
ACA TTC TAT GGC GCC AAC GGG GAT CCA AAG CCC CCT CAC ACA TAC ACG ATT GAC ATG AAG
 T   F   Y   G   A   N   G   D   P   K   P   P   H   T   Y   T   I   D   M   K 190           200           210           220           230           240
ACA ACT CAG AAC GTC AAC GGC TTG TCT ATG CTG CCT CGA CAG GAT GGT AAC CAA AAC GGC
 T   T   Q   N   V   N   G   L   S   M   L   P   R   Q   D   G   N   Q   N   G 250           260           270           280           290           300
TGG ATC GGT CGC CAT GAG GTT TAT CTA AGC TCA GAT GGC ACA AAC TGG GGC AGC CCT GTT
 W   I   G   R   H   E   V   Y   L   S   S   D   G   T   N   W   G   S   P   V 310           320           330           340           350           360
GCG TCA GGT AGT TGG TTC GCC GAC TCT ACT ACA AAA TAC TCC AAC TTT GAA ACT CGC CCT
 A   S   G   S   W   F   A   D   S   T   T   K   Y   S   N   F   E   T   R   P 370           380           390           400           410           420
GCT CGC TAT GTT CGT CTT GTC GCT ATC ACT GAA GCG AAT GGC CAG CCT TGG ACT AGC ATT
 A   R   Y   V   R   L   V   A   I   T   E   A   N   G   Q   P   W   T   S   I 430           440           450           460           470           480
GCA GAG ATC AAC GTC TTC CAA GCT AGT TCT TAC ACA GCC CCC CAG CCT GGT CTT GGA CGC
 A   E   I   N   V   F   Q   A   S   S   Y   T   A   P   Q   P   G   L   G   R 490           500           510           520           530           540
TGG GGT CCG ACT ATT GAC TTA CCG ATT GTT CCT GCG GCT GCA GCA ATT GAA CCG ACA TCG
 W   G   P   T   I   D   L   P   I   V   P   A   A   A   A   I   E   P   T   S 550           560           570           580           590           600
GGA CGA GTC CTT ATG TGG TCT TCA TAT CGC AAT GAT GCA TTT GGA GGA TCC CCT GGT GGT
 G   R   V   L   M   W   S   S   Y   R   N   D   A   F   G   G   S   P   G   G 610           620           630           640           650           660
ATC ACT TTG ACG TCT TCC TGG GAT CCA TCC ACT GGT ATT GTT TCC GAC CGC ACT GTG ACA
 I   T   L   T   S   S   W   D   P   S   T   G   I   V   S   D   R   T   V   T 670           680           690           700           710           720
GTC ACC AAG CAT GAT ATG TTC TGC CCT GGT ATC TCC ATG GAT GGT AAC GGT CAG ATC GTA
 V   T   K   H   D   M   F   C   P   G   I   S   M   D   G   N   G   Q   I   V 730           740           750           760           770           780
GTC ACA GGT GGC AAC GAT GCC AAG AAG ACC AGT TTG TAT GAT TCA TCT AGC GAT AGC TGG
 V   T   G   G   N   D   A   K   K   T   S   L   Y   D   S   S   S   D   S   W 790           800           810           820           830           840
ATC CCG GGA CCT GAC ATG CAA GTG GCT CGT GGG TAT CAG TCA TCA GCT ACC ATG TCA GAC
 I   P   G   P   D   M   Q   V   A   R   G   Y   Q   S   S   A   T   M   S   D
```

FIG. 27B

```
         850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC GAC GCC CAC ATC ATC ACC CTC GGT
 G   S   P   D   Y   Q   D   S   D   A   T   T   D   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510        1520        1530        1540        1550        1560
TTG TTA CCT GAT GGC AGG GTA TTT AAC GGT GGT GGT GGT CTT TGT GGC GAT TGT ACC ACG
 L   L   P   D   G   R   V   F   N   G   G   G   G   L   C   G   D   C   T   T 1570        1580        1590        1600        1610        1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630        1640        1650        1660        1670        1680
GCG ACA CGT CCC AAG ATT ACC AGA ACC TCA ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
         1810          1820          1830          1840          1850          1860
AGC TAT TCT TTC CAA GTT CCT AGC GAC TCT GGT GTT GCT TTG CCT GGC TAC TGG ATG TTG
 S   Y   S   F   Q   V   P   S   D   S   G   V   A   L   P   G   Y   W   M   L 1870          1880          1890          1900          1910          1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

```
Date          : 2000.04.11
Mutant ID     : 4.F12
Mutation      : N413D(A1237G),S550(T1650A),V494A(T1481C),S610(T1830A)
Sequence Size : 1917
```

```
         10          20          30          40          50          60
GCC TCA GCA CCT ATC GGA AGC GCC ATT TCT CGC AAC AAC TGG GCC GTC ACT TGC GAC AGT
 A   S   A   P   I   G   S   A   I   S   R   N   N   W   A   V   T   C   D   S 70          80          90         100         110         120
GCA CAG TCG GGA AAT GAA TGC AAC AAG GCC ATT GAT GGC AAC AAG GAT ACC TTT TGG CAC
 A   Q   S   G   N   E   C   N   K   A   I   D   G   N   K   D   T   F   W   H 130         140         150         160         170         180
ACA TTC TAT GGC GCC AAC GGG GAT CCA AAG CCC CCT CAC ACA TAC ACG ATT GAC ATG AAG
 T   F   Y   G   A   N   G   D   P   K   P   P   H   T   Y   T   I   D   M   K 190         200         210         220         230         240
ACA ACT CAG AAC GTC AAC GGC TTG TCT ATG CTG CCT CGA CAG GAT GGT AAC CAA AAC GGC
 T   T   Q   N   V   N   G   L   S   M   L   P   R   Q   D   G   N   Q   N   G 250         260         270         280         290         300
TGG ATC GGT CGC CAT GAG GTT TAT CTA AGC TCA GAT GGC ACA AAC TGG GGC AGC CCT GTT
 W   I   G   R   H   E   V   Y   L   S   S   D   G   T   N   W   G   S   P   V 310         320         330         340         350         360
GCG TCA GGT AGT TGG TTC GCC GAC TCT ACT ACA AAA TAC TCC AAC TTT GAA ACT CGC CCT
 A   S   G   S   W   F   A   D   S   T   T   K   Y   S   N   F   E   T   R   P 370         380         390         400         410         420
GCT CGC TAT GTT CGT CTT GTC GCT ATC ACT GAA GCG AAT GGC CAG CCT TGG ACT AGC ATT
 A   R   Y   V   R   L   V   A   I   T   E   A   N   G   Q   P   W   T   S   I 430         440         450         460         470         480
GCA GAG ATC AAC GTC TTC CAA GCT AGT TCT TAC ACA GCC CCC CAG CCT GGT CTT GGA CGC
 A   E   I   N   V   F   Q   A   S   S   Y   T   A   P   Q   P   G   L   G   R 490         500         510         520         530         540
TGG GGT CCG ACT ATT GAC TTA CCG ATT GTT CCT GCG GCT GCA GCA ATT GAA CCG ACA TCG
 W   G   P   T   I   D   L   P   I   V   P   A   A   A   I   E   P   T   S 550         560         570         580         590         600
GGA CGA GTC CTT ATG TGG TCT TCA TAT CGC AAT GAT GCA TTT GGA GGA TCC CCT GGT GGT
 G   R   V   L   M   W   S   S   Y   R   N   D   A   F   G   G   S   P   G   G 610         620         630         640         650         660
ATC ACT TTG ACG TCT TCC TGG GAT CCA TCC ACT GGT ATT GTT TCC GAC CGC ACT GTG ACA
 I   T   L   T   S   S   W   D   P   S   T   G   I   V   S   D   R   T   V   T 670         680         690         700         710         720
GTC ACC AAG CAT GAT ATG TTC TGC CCT GGT ATC TCC ATG GAT GGT AAC GGT CAG ATC GTA
 V   T   K   H   D   M   F   C   P   G   I   S   M   D   G   N   G   Q   I   V 730         740         750         760         770         780
GTC ACA GGT GGC AAC GAT GCC AAG AAG ACC AGT TTG TAT GAT TCA TCT AGC GAT AGC TGG
 V   T   G   N   D   A   K   K   T   S   L   Y   D   S   S   S   D   S   W 790         800         810         820         830         840
ATC CCG GGA CCT GAC ATG CAA GTG GCT CGT GGG TAT CAG TCA TCA GCT ACC ATG TCA GAC
 I   P   G   P   D   M   Q   V   A   R   G   Y   Q   S   S   A   T   M   S   D
```

FIG. 28B

```
             850         860         870         880         890         900
GGT CGT GTT TTT ACC ATT GGA GGC TCC TGG AGC GGT GGC GTA TTT GAG AAG AAT GGC GAA
 G   R   V   F   T   I   G   G   S   W   S   G   G   V   F   E   K   N   G   E 910         920         930         940         950         960
GTC TAT AGC CCA TCT TCA AAG ACA TGG ACG TCC CTA CCC AAT GCC AAG GTC AAC CCA ATG
 V   Y   S   P   S   S   K   T   W   T   S   L   P   N   A   K   V   N   P   M 970         980         990        1000        1010        1020
TTG ACG GCT GAC AAG CAA GGA TTG TAC CGT TCA GAC AAC CAC GCG TGG CTC TTT GGA TGG
 L   T   A   D   K   Q   G   L   Y   R   S   D   N   H   A   W   L   F   G   W 1030        1040        1050        1060        1070        1080
AAG AAG GGT TCG GTG TTC CAA GCG GGA CCT AGC ACA GCC ATG AAC TGG TAC TAT ACC AGT
 K   K   G   S   V   F   Q   A   G   P   S   T   A   M   N   W   Y   Y   T   S 1090        1100        1110        1120        1130        1140
GGA AGT GGT GAT GTG AAG TCA GCC GGA AAA CGC CAG TCT AAC CGT GGT GTA GCC CCT GAT
 G   S   G   D   V   K   S   A   G   K   R   Q   S   N   R   G   V   A   P   D 1150        1160        1170        1180        1190        1200
GCC ATG TGC GGA AAC GCT GTC ATG TAC GAC GCC GTT AAA GGA AAG ATC CTG ACC TTT GGC
 A   M   C   G   N   A   V   M   Y   D   A   V   K   G   K   I   L   T   F   G 1210        1220        1230        1240        1250        1260
GGC TCC CCA GAT TAT CAA GAC TCT GAC GCC ACA ACC GAC GCC CAC ATC ATC ACC CTC GGT
 G   S   P   D   Y   Q   D   S   D   A   T   T   D   A   H   I   I   T   L   G 1270        1280        1290        1300        1310        1320
GAA CCC GGA ACA TCT CCC AAC ACT GTC TTT GCT AGC AAT GGG TTG TAC TTT GCC CGA ACG
 E   P   G   T   S   P   N   T   V   F   A   S   N   G   L   Y   F   A   R   T 1330        1340        1350        1360        1370        1380
TTT CAC ACC TCT GTT GTT CTT CCA GAC GGA AGC ACG TTT ATT ACA GGA GGC CAA CGA CGT
 F   H   T   S   V   V   L   P   D   G   S   T   F   I   T   G   G   Q   R   R 1390        1400        1410        1420        1430        1440
GGA ATT CCG TTC GAG GAT TCA ACC CCG GTA TTT ACA CCT GAG ATC TAC GTC CCT GAA CAA
 G   I   P   F   E   D   S   T   P   V   F   T   P   E   I   Y   V   P   E   Q 1450        1460        1470        1480        1490        1500
GAC ACT TTC TAC AAG CAG AAC CCC AAC TCC ATT GTT CGC GCC TAC CAT AGC ATT TCC CTT
 D   T   F   Y   K   Q   N   P   N   S   I   V   R   A   Y   H   S   I   S   L 1510        1520        1530        1540        1550        1560
TTG TTA CCT GAT GGC AGG GTA TTT AAC GGT GGT GGT GGT CTT TGT GGC GAT TGT ACC ACG
 L   L   P   D   G   R   V   F   N   G   G   G   G   L   C   G   D   C   T   T 1570        1580        1590        1600        1610        1620
AAT CAT TTC GAC GCG CAA ATC TTT ACG CCA AAC TAT CTT TAC AAT AGC AAC GGC AAT CTC
 N   H   F   D   A   Q   I   F   T   P   N   Y   L   Y   N   S   N   G   N   L 1630        1640        1650        1660        1670        1680
GCG ACA CGT CCC AAG ATT ACC AGA ACC TCA ACA CAG AGC GTC AAG GTC GGT GGC AGA ATT
 A   T   R   P   K   I   T   R   T   S   T   Q   S   V   K   V   G   G   R   I 1690        1700        1710        1720        1730        1740
ACA ATC TCG ACG GAT TCT TCG ATT AGC AAG GCG TCG TTG ATT CGC TAT GGT ACA GCG ACA
 T   I   S   T   D   S   S   I   S   K   A   S   L   I   R   Y   G   T   A   T 1750        1760        1770        1780        1790        1800
CAC ACG GTT AAT ACT GAC CAG CGC CGC ATT CCC CTG ACT CTG ACA AAC AAT GGA GGA AAT
 H   T   V   N   T   D   Q   R   R   I   P   L   T   L   T   N   N   G   G   N
```

```
        1810            1820            1830            1840            1850            1860
AGC TAT TCT TTC CAA GTT CCT AGC GAC TCA GGT GTT GCT TTG CCT GGC TAC TGG ATG TTG
 S   Y   S   F   Q   V   P   S   D   S   G   V   A   L   P   G   Y   W   M   L 1870            1880            1890            1900            1910            1920
TTC GTG ATG AAC TCG GCC GGT GTT CCT AGT GTG GCT TCG ACG ATT CGC GTT ACT CAG
 F   V   M   N   S   A   G   V   P   S   V   A   S   T   I   R   V   T   Q
```

FIG. 28C

DIRECTED EVOLUTION OF OXIDASE ENZYMES

This patent application is a continuation-in-part of U.S. application No. 09/571,553, filed on May 16, 2000, which is incorporated herein by reference in its entirety.

This invention is concerned with the production of modified enzymes, particularly oxidase enzymes, and more particularly galactose oxidase enzymes. Recombinant techniques such as directed evolution are used to obtain polynucleotide and polypeptide products having desirable properties. Galactose oxidase variants with increased activity and increased thermostability relative to the wild-type enzyme are described.

BACKGROUND OF THE INVENTION

An "oxidation enzyme" is an enzyme that catalyzes one or more oxidation reactions, typically by adding, inserting, contributing or transferring oxygen from a source or donor to a substrate. Such enzymes are also called oxidoreductases or redox enzymes, and encompasses oxygenases, hydrogenases or reductases, oxidases and peroxidases. One such enzyme is galactose oxidase. This invention relates to the selection and production of polynucleotides that encode polypeptides or proteins with biological activity as oxidation enzymes, and in particular galactose oxidase enzymes. These enzymes are produced in facile expression systems such as robust prokaryotic cells (e.g. bacteria) and eukaryotic systems (e.g. fungi and yeast).

FIELD OF THE INVENTION

The invention concerns the recombinant production of functional eukaryotic proteins by host cells, in high yield, with increased activity, and/or with increased stability, e.g. thermostability. Preferred proteins of the invention include oxidase enzymes (oxidases) such as polypeptides evolved from galactose oxidase (D-galactose:oxygen 6-oxidoreductase or GAO, EC 1.1.3.9). Polynucleotides which encode and express these proteins in recombinant host cell expression systems, and the resulting polypeptides, are encompassed by the invention.

The publications and reference materials noted herein and listed in the appended Bibliography are each incorporated by reference in their entirety. They are referenced numerically in the text and the Bibliography below.

Production of Enzyme Variants

Many proteins of interest are produced by organisms having "eukaryotic" cells. These are cells having a nucleus surrounded by its own membrane and containing DNA on structures called chromosomes. All multicellular organisms, such as humans and animals, and many single-cell animals, have eukaryotic cells. Other single-cell organisms, such as bacteria have "prokaryotic" cells. These cells have a primitive nucleus with DNA in a defined structure, but without chromosomes and a nuclear membrane that is characteristic of eukaryotes. Prokaryotic organisms are generally much easier and less costly to grow, maintain and manipulate than eukaryotic cells.

Genetic engineering and recombinant DNA and RNA technologies have made it possible to produce proteins, hormones and enzymes that are native to one organism, by using the cells of a different organism as "factories" or host cell expression systems. In particular, it is often desirable to express a protein of eukaryotic origin in a prokaryotic host cell, because the prokaryotes can be grown in large quantities of identical cells, to produce large amounts of the desired foreign protein. For example, certain human proteins may be useful as drugs if they can be supplied in sufficient quantity to patients who have a protein deficiency. Such proteins may not easily or ethically be obtained by isolating them from human cells, nor can they easily be made by direct chemical synthesis or by growing them in isolated tissue cultures. Other proteins and enzymes are useful in industry. For example, certain enzymes can break down food products, and are useful in laundry detergent. However, commercial applications require large amounts of protein and a high degree of quality control. Desirable applications also require or would benefit from more active or more thermostable (heat resistant) proteins or enzymes.

To solve some of these problems, recombinant genetic engineering techniques have been developed to use genetic machinery of other cells, such as bacteria and yeast, to produce human or other proteins. Selected genetic material, such as a polynucleotide that encodes a desired protein, is "recombined" with genetic material in a host cell, so that the host cell expresses the introduced foreign genetic material and produces the desired polypeptide or protein. Bacteria, fungi and and yeast can be suitable host cells because they are easy and economical to grow and maintain in large quantities, and can be used to reliably and repeatably produce foreign proteins. Some proteins that are made by cells can be secreted or delivered outside the cell, which can improve the yield and the efficiency of subsequent isolation and purification steps.

Directed evolution has been successfully applied to improve a variety of enzyme properties, such as substrate specificity, activity in organic solvents, and stability at high temperatures, which are often critical for industrial applications (5). This evolutionary approach uses DNA shuffling, for simultaneous random mutagenesis and recombination, to generate a variant having an improved desirable property over the existing wild type protein. Point mutations are generated due to the intrinsic infidelity of Taq-based polymerase chain reactions (PCR) associated with reassembly of nucleic acid sequences. In one example, Stemmer and coworkers applied this technique to the gene encoding for green fluorescence protein (GFP), which resulted in a protein that folded better than the wild type in *E. Coli* (10). Other examples are in the literature. (11–18, 21–25, 27–34, 47–58, 60–63, 65–75). Eukaryotic enzymes have a myriad of existing and potential applications, but improvement of these and other proteins by directed evolution is desirable. For example, the difficulty of expressing certain oxidase enzymes in a facile expression host has posed technical challenges. Efforts to modify these enzymes for industrial applications by protein engineering methods have been impeded. Directed evolution, for example, exploits expression in a host such as *E. Coli* or *S. cerevisiae*, organisms in which large libraries of mutants or variants can be made. Also, the lack of efficient expression in an appropriate foreign (heterologous) host can prevent the mass production of some of these proteins on an economical scale. Thus, there continues to be a need for new ways to produce new proteins, and for new proteins and enzymes having new or enhanced biological properties.

Galactose Oxidase Enzymes

One protein of interest is the oxidation enzyme galactose oxidase. Galactose oxidase (D-galactose: oxygen 6-oxidoreductase, GAO, EC 1.1.3.9) is an enzyme containing a single copper ion, and is secreted by a number of fungal species. *Fusarium* NRRL 2903, formerly known as *Dactylium dendroides*, has been the most extensively studied (76).

The enzyme is a glycoprotein with a carbohydrate content of about 1.7% and consists of a single polypeptide chain of 639 amino acid residues with molecular mass of 68,000 Da (77, 78). The reaction catalyzed by GAO is the oxidation of primary alcohols to the corresponding aldehydes, coupled to the two-electron reduction of $O_2$ to hydrogen peroxide (79).

The enzyme oxidizes an unusually broad range of substrates. It accepts D-galactose (FIG. 1), alpha- and beta-galactopyranosides, oligo- and polysaccharides and considerably smaller molecules, such as glycerol and allyl alcohol, as substrates (77, 80–82). GAO exhibits prochiral (only the pro-S hydrogen is abstracted) as well as enantiomeric specificity for galactose (only D-galactose is oxidized by the enzyme) (80, 83). Furthermore, GAO strictly discriminates against D-glucose, the C-4 epimer of D-galactose, as a substrate or ligand. D-glucose does not bind to GAO at concentrations as high as 1 M (80, 84). The kinetic parameters of GAO for the oxidation of galactose are: $K_m$=67 mM, $k_{cat}$=3,000 sec$^{-1}$, $k_{cat}/K_m$=45×10$^3$ M$^{-1}$ sec$^{-1}$ (85).

The crystal structure of GAO has been reported (86). It consists of three predominantly beta-structure domains. The copper ion lies on the solvent-accessible surface of the second and largest domain (residues 156–532) (78, 87). Tyr-272, Tyr-495, His-496, His-581 and a water molecule are the copper ligands at pH 7.0. The crystal structure also reveals a novel thioether bond linking Cys-228 and Tyr-272 and supports the presence of a tyrosine free radical at the active site (79). The active site structure of GAO is shown in FIG. 2. Site-directed mutagenesis of Tyr-495 and Cys-228 have confirmed their involvement in catalysis (85, 88).

GAO is useful in a wide variety of applications, ranging from analytical and food chemistry to chemoenzymatic synthesis and clinical testing. For example, biological sensors based on GAO have been developed to determine the content of galactose (89), lactose and other GAO substrates (90). Such biosensors have also been used for quality control in dairy industries (91, 92), online bioprocess monitoring (93) and analysis of blood samples of patients with suspected galactosemia (94). The stereospecificity and broad substrate specificity of GAO have been exploited in the chemoenzymatic synthesis of L-sugars from polyols (95), which are usually difficult to prepare by chemical methods (96, 97), as well as sugar-containing polyamines (98) and 5-C-(hydroxymethyl)hexoses (99). GAO applications in synthesis have been limited due to its relatively low activity toward a large number of primary alcohols (100). Additionally, GAO is also used for the detection of the disaccharide D-galactose-beta-(1->3)—N-acetylgalactosamine (Gal-GalNAc), a tumor marker in colonic cancer and precancer, and provides a cost-effective screening test for patients with neoplasia or at the risk of developing neoplasia (101, 102). GAO finds applications in food chemistry. For example, it has been used in oxidized guar manufacture (103) and to treat the oligosaccharide fraction contained in honey (104). Finally, GAO is used to oxidize the cell surface polysaccharides of membrane-bound glycoproteins containing terminal non-reducing galactose residues: this is an essential step in the successful radiolabeling of these glycoconjugates (105, 106).

Modified and particularly improved or optimized GAO enzymes are useful to improve and expand the use of the enzyme in practical applications. For example, enzymes of the invention include GAO variants that are more active, more thermostable, or both. Increased activity and/or expression as well as high thermostability may significantly decrease the cost of enzyme production, simplify its purification and handling, and prolong its shelf-life. Other properties of the enzyme may also be varied, for example to optimize activity towards particular substrates or toward other substrates such as polymeric materials and glucose.

Use of these evolved enzymes in biosensors and diagnostics can increase the sensitivity, decrease the response time and enhance the detection range. In addition, a more stable enzyme will find applications in the construction of biosensors with prolonged stability. An evolved GAO with improved activity toward poor GAO substrates, such as allyl alcohol and glucose, will provide new and improved applications of the enzyme in organic synthesis and other sensor applications. For chemical synthesis applications, selective oxidation of alcohols to the corresponding aldehydes avoids the use of protecting groups, minimizes side reactions often observed in traditional chemical synthesis, and is an environmentally friendly process. Use of such GAO enzymes as a synthetic reagent would facilitate the use of more inexpensive, safe and biodegradable carbohydrate materials in industrial processes (107).

A more efficient enzyme is expected to be advantageous in the food chemistry applications of GAO, and, in particular in the selective modification of guar and other carbohydrate-based polymers. GAO variants according to the invention would also be useful for modification of carbohydrate-based (e.g. cellulosic) textiles and other materials. The aldehyde function produced by the GAO can be used to couple other substances selectively at the modified position on the polymer.

Accordingly, there is a need to develop new and improved GAO enzymes, as well as methods for expressing such proteins. In particular, there is a need for protein expression methods which are well-suited for use in connection with directed evolution techniques.

This invention describes methods for screening libraries of GAO mutants produced by error-prone PCR and DNA shuffling, to identify mutations that are expressed in bacteria (e.g. *E. coli*) and with improved GAO function. Micro-plate and membrane screening techniques are disclosed. In one embodiment, the mutant is a functional and active galactose oxidase (GAO) that is expressed in *E. Coli* at levels of about 65 times the activity of a parent recombinant wild type (for D-galactose). The activity for other substrates, such as allyl alcohol, is also about 65 times that of wild type. Mutants of the invention can have any fraction or multiple of the corresponding wild type activity, but preferably are more active, e.g. about 2 to 200 times as active. Mutants also are more thermostable. Enzyme yield is generally at least about 10 mg/l.

SUMMARY OF THE INVENTION

The observed constraints on the use of native proteins are thought to be a consequence of evolution. Proteins have evolved in the context and environment of a living organism, to carry out specific biological functions under conditions conducive to life—not in the laboratory or under industrial conditions. In some cases, evolution may favor or even require less than optimally efficient enzymes. The output, efficiency, working conditions, stability and other properties of known expression systems are not thought to be unalterable, nor are they limitations which should be seen as intrinsic to the nature of cellular expression systems. It is possible that the proteins used in these systems can be evolved in vitro, or that analogous proteins can be otherwise developed, to alter or enhance the protein's properties, for example, to obtain much more efficient expression, activity and thermostability. Improved proteins can also be obtained by screening cultures of native organisms or expressed gene libraries (3).

The invention provides a method for improving the expression, thermostability, and/or the activity toward one or more substrates, of a polynucleotide encoding oxidase enzymes by using directed evolution. The invention also provides polynucleotides encoding for variant oxidase enzymes which have improved properties in conventional expression systems. According to one embodiment of the invention, directed evolution or random mutagenesis is used to produce GAO variants which are more highly expressed, more active, and/or more thermostable in prokaryotic expression systems such as E. coli.

The above features and many other attendant advantages of the invention will become better understood by reference to the following detailed description when taken in conjunction with the accompanying drawings.

BRIEF DESCRIPTION OF THE DRAWINGS

FIG. 6 shows the sequences of PCR primers used herein for amplification, e.g. of the whole galactose oxidase gene.

FIG. 11 shows the structures and activities of representative plasmids encoding GAO according to the invention, with IPTG-induced expression in host E. coli. Permeable cells which were treated by freeze (−20° C.), thaw (4° C.) and 0.5 mg/l lysozyme for 30 minutes at 37° C. were used for assay. Activities given as * indicates that cells did not grow in test tube culture; **indicates that a transformant was not obtained.

FIG. 15 shows substrate specificities for a wild type galactose oxidase and a recombinant galactose oxidase enzyme of the invention. Partially purified galactose oxidase from D. dendroides (Sigma) and cell-free extract from E. coli BL21(DE3)/pGAO-010 were used. Relative activities for D-galactose were estimated as 100%. (+) indicates that oxidation was detected, but activities were too low to be estimated. n.d. indicates that activities were not distinguishable from background absorbance levels.

FIGS. 17A–C show the sequence of representative mutant 9.16.8D2 of the invention [SEQ. ID NO. 10 and 37]

FIGS. 18A–C show the sequence of representative mutant 9.16.6C11 of the invention [SEQ. ID NO. 11 and 38]

FIGS. 19A–C show the sequence of representative mutant 9.16.16D12 of the invention [SEQ. ID NO. 12 and 39]

FIGS. 20A–C show the sequence of representative mutant 11.03.6D3 of the invention [SEQ. ID NO. 13 and 40]

FIGS. 21A–C show the sequence of representative mutant 11.03.10C3 of the invention [SEQ. ID NO. 14 and 41]

FIGS. 22A–C show the sequence of representative mutant 11.03.10D6 of the invention [SEQ. ID NO. 15 and 42]

FIGS. 23A–C show the sequence of representative mutant 11.03.13E12 of the invention [SEQ. ID NO. 16 and 43]

FIGS. 24A–C show the sequence of representative mutant 1.06.20E7 of the invention [SEQ. ID NO. 17 and 44]

FIGS. 25A–C show the sequence of representative mutant 1.D4 of the invention [SEQ. ID NO. 18 and 45]

FIGS. 26A–C show the sequence of representative mutant 2G4 of the invention [SEQ. ID NO. 19 and 46]

FIGS. 27A–C show the sequence of representative mutant 3.H7 of the invention [SEQ. ID NO. 20 and 47]

FIGS. 28A–C show the sequence of representative mutant 4.F12 of the invention [SEQ. ID NO. 21 and 48]

DETAILED DESCRIPTION OF THE INVENTION

Figure 1:
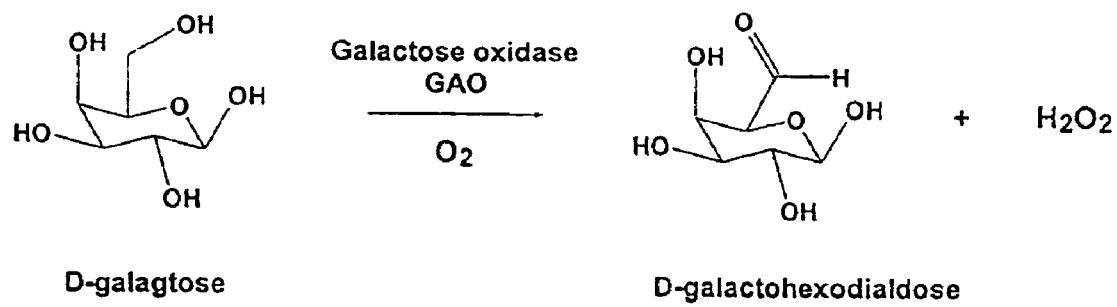
FIG. 1 shows a reaction scheme in which a D-galactose substrate is oxidized to produce a D-galactohexodialdose product, in the presence of galactose oxidase (GAO) enzyme.

This invention concerns methods for improving the expression, activity and/or thermostability of proteins using facile or conventional expression systems.

Definitions

As used herein, "about" or "approximately" shall mean within 20 percent, preferably within 10 percent, and more preferably within 5 percent of a given value or range.

The term "substrate" means any substance or compound that is converted or meant to be converted into another compound by the action of an enzyme catalyst. The term includes aromatic and aliphatic compounds, and includes not only a single compound, but also combinations of compounds, such as solutions, mixtures and other materials which contain at least one substrate.

An "oxidation reaction" or "oxygenation reaction", as used herein, is a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it receives oxygen or loses electrons. A compound is "reduced" when it loses oxygen or gains electrons. GAO typically catalyzes the oxidation of a primary alcohol group to an aldehyde.

The term "enzyme" means any substance composed wholly or largely of protein or polypeptides that catalyzes or promotes, more or less specifically, one or more chemical or biochemical reactions.

A "polypeptide" (one or more peptides) is a chain of chemical building blocks called amino acids that are linked together by chemical bonds called peptide bonds. A protein or polypeptide, including an enzyme, may be "native" or "wild-type", meaning that it occurs in nature or has the amino acid sequence of a native protein, respectively. These terms are sometimes used interchangeably. A polypeptide may or may not be glycosylated. A "recombinant wild-type" typically means the wild type sequence in a recombinant host without glycosylation. Comparisons in the examples and figures of this application are generally with reference to a wild type that is a recombinant wild type. A polypeptide may also be a "mutant", "variant" or "modified", meaning that it has been made, altered, derived, or is in some way different or changed from a native protein, or from another mutant. A native wild type protein comprises the natural sequence of amino acids in the polypeptide and typically includes glycosylation. A "parent" polypeptide or enzyme is any polypeptide or enzyme from which any other polypeptide or enzyme is derived or made, using any methods, tools or techniques, and whether or not the parent is itself a native or mutant polypeptide or enzyme. A parent polynucleotide is one that encodes a parent polypeptide. A "test enzyme" is a protein-containing substance that is tested to determine whether it has properties of an enzyme. The term "enzyme" can also refer to a catalytic polynucleotide (e.g. RNA or DNA).

The "activity" of an enzyme is a measure of its ability to catalyze a reaction, and may be expressed as the rate at which the product of the reaction is produced. For example, enzyme activity can be represented as the amount of product produced per unit of time, per unit (e.g. concentration or weight) of enzyme. The "stability" of an enzyme means its ability to function, over time, in a particular environment or under particular conditions. One way to evaluate stability is to assess its ability to resist a loss of activity over time, under given conditions. Enzyme stability can also be evaluated in other ways, for example, by determining the relative degree to which the enzyme is in a folded or unfolded state. Thus, one enzyme is more stable than another, or has improved stability, when it is more resistant than the other enzyme to a loss of activity under the same conditions, is more resistant to unfolding, or is more durable by any suitable measure. For example, a more "thermally stable" or "thermostable" enzyme is one that is more resistant to loss of structure (unfolding) or function (enzyme activity) when exposed to heat or an elevated temperature. One way to evaluate this is to determine the "melting temperature" or $T_m$ for the protein. The melting temperature, also called a midpoint, is the temperature at which half of the protein is unfolded from its fully folded state. This midpoint is typically determined by calculating the midpoint of a titration curve that plots protein unfolding as a function of temperature. Thus, a protein with a higher $T_m$ requires more heat to cause unfolding and is more stable or more thermostable. Stated another way, a protein with a higher $T_m$ indicates that fewer molecules of that protein are unfolded at the same temperature as a protein with a lower $T_m$, again meaning that the protein which is more resistant to unfolding is more stable (it has less unfolding at the same temperature). Another measure of stability is $T_{1/2}$ or $T_{50}$, which is the transition midpoint of the inactivation curve of the protein as a function of temperature. $T_{1/2}$ is the temperature at which the protein loses half of its activity. Thus, a protein with a higher $T_{1/2}$ requires more heat to deactivate it, and is more stable or more thermostable. Stated another way, a protein with a higher $T_{1/2}$ indicates that fewer molecules of that protein are inactive at the same temperature as a protein with a lower $T_{1/2}$, again meaning that the protein which is more resistant to deactivation is more stable (it has more activity at the same temperature). These assays are also called "thermal shift" assays, because the inactivation or unfolding curve, plotted against temperature, is "shifted" to higher or lower temperatures when stability increases or decreases. Thermostability can also be measured in other ways. For example, a longer half-life ($t_{1/2}$) for the enzyme's activity at elevated temperature is an indication of thermostability.

An "oxidation enzyme" is an enzyme that catalyzes one or more oxidation reactions, typically by adding, inserting, contributing or transferring oxygen from a source or donor to a substrate. Such enzymes are also called oxidoreductases or redox enzymes, and encompasses oxygenases, hydrogenases or reductases, oxidases and peroxidases.

The terms "oxygen donor", "oxidizing agent" and "oxidant" mean a substance, molecule or compound which donates oxygen to a substrate in an oxidation reaction. Typically, the oxygen donor is reduced (accepts electrons). Exemplary oxygen donors, which are not limiting, include molecular oxygen or dioxygen ($O_2$) and peroxides, including alkyl peroxides such as tbutyl peroxide, and most preferably hydrogen peroxide ($H_2O_2$). A peroxide is any compound having two oxygen atoms bound to each other.

A "luminescent" substance means any substance which produces detectable electromagnetic radiation, or a change in electromagnetic radiation, most notably visible light, by any mechanism, including color change, UV absorbance, fluorescence and phosphorescence. Preferably, a luminescent substance according to the invention produces a detectable color, fluorescence or UV absorbance. The term "chemiluminescent agent" means any luminescent substance which enhances the detectability of a luminescent (e.g., fluorescent) signal, for example by increasing the strength or lifetime of the signal. One exemplary and preferred chemiluminescent agent is azinobis(3-ethylbenzothiazoline-6-sulfonic acid) (ABTS). 5-amino-2,3-dihydro-1,4-phthalazinedione (luminol) and analogs. Others include 5-amino-2,3-dihydro-1,4-phthalazinedione (luminol) and analogs, 1,2-dioxetanes such as tetramethyl-1,2-dioxetane (TMD), 1,2-dioxetanones, and 1,2-dioxetanediones, o-anisidine, o-dianisidine, and o-tolidine. Another term for these kinds of materials is "chromogen."

The term "polymer" means any substance or compound that is composed of two or more building blocks ('mers') that are repetitively linked to each other. For example, a "dimer" is a compound in which two building blocks have been joined together.

The term "cofactor" means any non-protein substance that is necessary or beneficial to the activity of an enzyme. A "coenzyme" means a cofactor that interacts directly with and serves to promote a reaction catalyzed by an enzyme. Many coenzymes serve as carriers. For example, $NAD^-$ and $NADP^-$ carry hydrogen atoms from one enzyme to another. An "ancillary protein" means any protein substance that is necessary or beneficial to the activity of an enzyme.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA—DNA, DNA-RNA and RNA—RNA hybrids, as well as "protein nucleic acids" (PNA) formed by conjugating bases to an amino acid backbone. This also includes nucleic acids containing modified bases, for example thiouracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme. A coding sequence is "under the control" of transcriptional and translational control sequences in a cell when RNA polymerase transcribes the coding sequence into mRNA, which is then trans-RNA spliced and translated into the protein encoded by the coding sequence. Preferably, the coding sequence is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining this invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. As described above, promoter DNA is a DNA sequence which initiates, regulates, or otherwise mediates or controls the expression of the coding DNA. A promoter may be "inducible", meaning that it is influenced by the presence or amount of another compound (an "inducer"). For example, an inducible promoter includes those which initiate or increase the expression of a downstream coding sequence in the presence of a particular inducer compound. A "leaky" inducible promoter is a promoter that provides a high expression level in the presence of an inducer compound and a comparatively very low expression level, and at minimum a detectable expression level, in the absence of the inducer.

A "signal sequence" is included at the beginning of the coding sequence of a protein to be expressed in the periplasmic space, or outside the cell. This sequence encodes a signal peptide, N-terminal to the mature polypeptide, that directs the host cell to translocate the polypeptide. The term "translocation signal sequence" is also used to refer to a signal sequence. Translocation signal sequences can be found associated with a variety of proteins native to eukaryotes and prokaryotes, and are often functional in both types of organisms. Proteins of the invention may be further modified and improved by adding a sequence which directs the secretion of the protein outside the host cell. The addition of the signal sequence does not interfere with the folding of the secreted protein, and evidence thereof is easily tested for using techniques known in the art and depending on the protein (e.g., tests for activity of a given protein after modification).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

A polynucleotide or polypeptide is "over-expressed" when it is expressed or produced in an amount or yield that is substantially higher than a given base-line yield, e.g. a yield that occurs in nature. For example, a polypeptide is over-expressed when the yield is substantially greater than the normal, average or base-line yield of the native polypolypeptide in native host cells under given conditions, for example conditions suitable to the life cycle of the native host cells. Over-expression of a polypeptide can be obtained, for example, by altering any one or more of (a) the growth or living conditions of the host cells; (b) the polynucleotide encoding the polypeptide to be over-expressed; (c) the promoter used to control expression of the polynucleotide; and (d) the host cells themselves. This is a relative, and thus "over-expression" can also be used to compare or distinguish the expression level of one polypeptide to another, without regard for whether either polypeptide is a native polypeptide or is encoded by a native polynucleotide. Typically, over-expression means a yield that is at least about two times a normal, average or given base-line yield. Thus, a polypeptide is over-expressed when it is produced in an amount or yield that is substantially higher than the amount or yield of a parent polypeptide or under parent conditions. Likewise, a polypeptide is "under-expressed" when it is produced in an amount or yield that is substantially lower than the amount or yield of a parent polypeptide or under parent conditions, e.g. at least half the base-line yield. In this context, the expression level or yield refers to the amount or concentration of polynucleotide that is expressed, or polypeptide that is produced (i.e. expression product), whether or not in an active or functional form. As one example, a polynucleotide or polypeptide may be said to be under-expressed when it is expressed in detectable amounts under the control of an inducible promoter, but without induction, i.e. in the absence of an inducer compound.

An expression product can be characterized as intracellular, extracellular or secreted. The term "intracellular" means something that is inside a cell. The term "extracellular" means something that is outside a cell. A substance is "secreted" by a cell if it delivered to the periplasm or outside the cell, from somewhere on or inside the cell.

As used herein, the terms "expression-resistant polypeptide" and "resistant to functional expression" are synonymous and refer to a polypeptide that is difficult to functionally express in selected host cells. For example, an expression-resistant polypeptide is not produced, or is produced in very low yield or in non-functional form, when a polynucleotide encoding that polypeptide is transformed or introduced into host cells, e.g. into a facile host cell expression system.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct."

A common type of vector is a "plasmid", which generally is a self-contained molecule of double-stranded DNA, that can readily accept additional (foreign) DNA and which can readily introduced into a suitable host cell. A plasmid vector often contains coding DNA and promoter DNA and has one or more restriction sites suitable for inserting foreign DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Routine experimentation in biotechnology can be used to determine which vectors are best suited for used with the invention. In general, the choice of vector depends on the size of the polynucleotide sequence and the host cell to be employed in the methods of this invention.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

The term "expression system" means a host cell and compatible vector under suitable conditions, e.g. for the expression of a protein coded for by foreign DNA carried by the vector and introduced to the host cell. Common expression systems include bacteria (e.g. *E. coli* and *B. subtilis*) or yeast (e.g. *S. cerevisiae*) host cells and plasmid vectors, and insect host cells and *Baculovirus* vectors. As used herein, a "facile expression system" means any expression system that is foreign or heterologous to a selected polynucleotide or polypeptide, and which employs host cells that can be grown or maintained more advantageously than cells that are native or heterologous to the selected polynucleotide or polypeptide, or which can produce the polypeptide more efficiently or in higher yield. For example, the use of robust prokaryotic cells to express a protein of eukaryotic origin would be a facile expression system. Preferred facile expression systems include *E. Coli, B. subtilis* and *S. cerevisiae* host cells and any suitable vector.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant. Such changes also include changes in the promoter, ribosome binding site, etc.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, acidic, basic, hydrophobic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

The term "DNA reassembly" is used when recombination occurs between identical sequences. "DNA shuffling" refers to a group of in vitro or in vivo methods involving recombination of nucleic acid species. For example, homologous recombination of pools of nucleic acid fragments or polynucleotides can be employed to generate polynucleotide molecules having variant sequences of the invention. Such methods can be employed to generate polynucleotide molecules having variant sequences of the invention.

"Isolation" or "purification" of a polypeptide or enzyme refers to the derivation of the polypeptide by removing it from its original environment (for example, from its natural environment if it is naturally occurring, or form the host cell if it is produced by recombinant DNA methods). Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible. A purified polynucleotide or polypeptide may contain less than about 50%, preferably less than about 75%, and most preferably less than about 90%, of the cellular components with which it was originally associated. A "substantially pure" enzyme indicates the highest degree of purity which can be achieved using conventional purification techniques known in the art.

Polynucleotides are "hybridizable" to each other when at least one strand of one polynucleotide can anneal to another polynucleotide under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5× SSC at 65° C.) requires that the sequences exhibit some high degree of complementarity over their entire sequence. Conditions of intermediate stringency (such as, for example, an aqueous solution of 2× SSC at 65° C.) and low stringency (such as, for example, an aqueous solution of 2× SSC at 55° C.), require correspondingly less overall complementarity between the hybridizing sequences. (1× SSC is 0.15 M NaCl, 0.015 M Na citrate.) Polynucleotides that "hybridize" to the polynucleotides herein may be of any length. In one embodiment, such polynucleotides are at least 10, preferably at least 15 and most preferably at least 20 nucleotides long. In another embodiment, polynucleotides that hybridizes are of about the same length. In another embodiment, polynucleotides that hybridize include those which anneal under suitable stringency conditions and which encode polypeptides or enzymes having the same function, such as the ability to catalyze an oxidation, oxygenase, or coupling reaction of the invention.

The general genetic engineering tools and techniques discussed here, including transformation and expression, the use of host cells, vectors, expression systems, etc., are well known in the art.

Mutagenesis and Directed Evolution of Proteins

To improve the expression and function of proteins using conventional expression systems, the invention makes the unexpected discovery that directed evolution can be used to generate mutant libraries of polynucleotides which, when expressed using conventional or facile expression systems, result in functional proteins having increased activity and/or thermostability.

According to the invention, proteins that are expressed in facile gene expression systems can be obtained by using directed evolution to generate mutant polynucleotides in a library format for selection. General methods for generating libraries and isolating and identifying improved proteins (also described as "variants") according to the invention using directed evolution are described briefly below and more extensively, for example, in U.S. Pat. Nos. 5,741,691 and 5,811,238. See also, International Applications WO 98/42832, WO 95/22625, WO 97/20078, and WO 95/and U.S. Pat. Nos. 5,605,793 and 5,830,721 (143, 149–156). It should be understood that any method for generating mutations in polynucleotide sequences to provide an evolved polynucleotide for use in expression systems can be employed. Proteins produced by directed evolution methods can then be screened for improved expression, activity, thermostability, folding, secretion, and other functions and properties according to conventional methods.

Any source of nucleic acid in purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50,000 base pairs. It is contemplated that entire vectors containing the nucleic acid encoding the protein of interest may be used in the methods of this invention.

Any specific nucleic acid sequence can be used to produce the population of mutants by the present process. An initial population of the specific nucleic acid sequences having mutations may be created by a number of different known methods, some of which are set forth below.

Error-prone polymerase chain reaction (20,45,46) and cassette mutagenesis (38–44), in which the specific region optimized is replaced with a synthetically mutagenized oligonucleotide can be employed in the invention. Error-prone PCR can be used to mutagenize a mixture of fragments of unknown sequences. These techniques can also be employed under low-fidelity polymerization conditions to introduce a low level of point mutations randomly over a long sequence, or to mutagenize a mixture of fragments of unknown sequence.

Oligonucleotide-directed mutagenesis, which replaces a short sequence with a synthetically mutagenized oligonucleotide may also be employed to generate evolved polynucleotides having improved expression.

Alternatively, nucleic acid or DNA shuffling, which uses a method of in vitro or in vivo, generally homologous, recombination of pools of nucleic acid fragments or polynucleotides, can be employed to generate polynucleotide molecules having variant sequences of the invention.

Parallel PCR is another method that can be used to evolve polynucleotides for improved expression, function or properties in conventional expression systems, which uses a large number of different PCR reactions that occur in parallel in the same vessel, such that the product of one reaction primes the product of another reaction. Sequences can be randomly mutagenized at various levels by random fragmentation and reassembly of the fragments by mutual priming. Site-specific mutations can be introduced into long sequences by random fragmentation of the template followed by reassembly of the fragments in the presence of mutagenic oligonucleotides.

A particularly useful application of parallel PCR, which can be used in the invention, is called sexual PCR. In sexual PCR, also known as DNA shuffling, parallel PCR is used to perform ill vitro recombination on a pool of DNA sequences. Sexual PCR can also be used to construct libraries of chimaeras of genes from different species.

The polynucleotide sequences for use in the invention can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light, or by subjecting the polynucleotide to propagation in a host (such as $E.\ coli$) that is deficient in thenormal DNA damage repair function. Generally, plasmid DNA or DNA fragments so mutagenized are introduced into $E.\ coli$ and propagated as a pool or library of mutant plasmids.

Alternatively a mixed population of specific nucleic acids may be found in nature in that they may consist of different alleles of the same gene or the same gene from different related species (i.e., cognate genes). Alternatively, they may be related DNA sequences found within one species, for example, the oxidase class of genes. Once the mixed population of the specific nucleic acid sequences is generated, the polynucleotides can be used directly or inserted into an appropriate cloning vector, using techniques well-known in the art.

Once the evolved polynucleotide molecules are generated they can be cloned into a suitable vector selected by the skilled artisan according to methods well known in the art. If a mixed population of the specific nucleic acid sequence is cloned into a vector it can be clonally amplified by inserting each vector into a host cell and allowing the host cell to amplify the vector. The mixed population may be tested to identify the desired recombinant nucleic acid fragment. The method of selection will depend on the DNA fragment desired. For example, in this invention a DNA fragment which encodes for a protein with improved properties can be determined by tests for functional activity and/or stability of the protein. Such tests are well known in the art.

Using the methods of directed evolution, the invention provides a novel means for producing functional, and soluble proteins with improved activity toward one or more substrates. The mutants can be expressed in conventional or facile expression systems such as $E.\ coli$. Conventional tests can be used to determine whether a protein of interest produced from an expression system has improved expression, folding and/or functional properties. For example, to determine whether a polynucleotide subjected to directed evolution and expressed in a foreign host cell produces a protein with improved activity, one skilled in the art can perform experiments designed to test the functional activity of the protein. Briefly, the evolved protein can be rapidly screened, and is readily isolated and purified from the expression system or media if secreted. It can then be subjected to assays designed to test functional activity of the particular protein in native form. Such experiments for various proteins are well known in the art, and are discussed in the Examples below.

In one embodiment, the invention contemplates the use polynucleotides encoding for variants of oxidase enzymes. The invention employs directed evolution to generate novel oxidase enzymes, such as GAO, which are expressed in host cells (e.g. *E. coli*) used in an expression system, and which exhibit increased functional activity and increased thermostability.

The invention can also be applied to select or optimize an expression system, including selection of host cells, promoters, and signal sequences. Expression conditions can also be optimized according to the invention.

Directed Evolution of Galactose Oxidase

Figure 2:
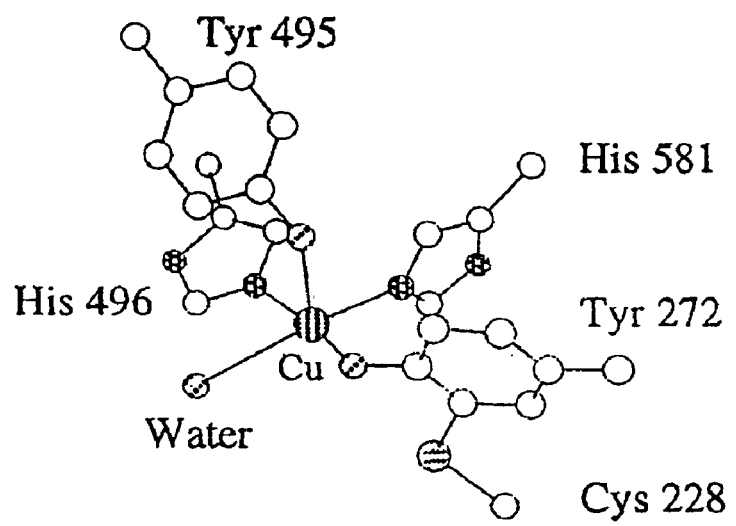
FIG. 2 shows the active site structure of GAO pH 7.0

Galactose oxidase (EC 1.1.3.9) is an alcohol oxidase enzyme. It oxidizes the hydroxyl group of the sixth carbon of D-galactose. It also oxidizes many other kinds of sugars and alcohols (77, 108, 114, 115, 118–120). Although many fungi produce galactose oxidase, no bacterium has been reported to produce the enzyme (109). There are many reports about galactose oxidase from *Eusarium* ssp. NRRL2903, which is identical to *Dactylium dendroides* ATCC46032 (76–78, 84–86, 88, 95, 99, 108, 110–128). FIG. 1 The native enzyme is an extracellular monomer enzyme and has molecular weight as 67,000. It has one copper (II) ion associated with it active site and related to its oxidation properties. FIG. 2. Structure and amino acid residues related to catalysis have been characterized and reported (76, 78, 84–86, 88, 111–113, 116–119).

Galactose oxidase is currently used mainly for assays of D-galactose and D-galactosamine. The enzyme oxidizes the hydroxyl group in the substrate to an aldehyde, which is reactive. Therefore, the enzyme is implicated for use in production of non-natural sugars and derivatives of sugars (118, 119, 95, 99, 128). Hyper-production of galactose oxidase would be useful for a wide variety of applications. The gene of the galactose oxidase has been cloned (110) and expressed in *Escherichia coli* (127). This recombinant galactose oxidase was produced as a fused protein with the N-terminal sequence of LacZ. However, the yield of the galactose oxidase by this recombinant *E. coli* was not satisfactory.

According to the invention, galactose oxidase enzyme (GAO) has been produced in high activity and with improved properties by recombinant techniques in *E. coli*.

The following Examples are understood to be exemplary only, and do not limit the scope of the invention or the appended claims A person of ordinary skill in the art will appreciate that the invention can be practiced in many forms according to the claims and disclosures here.

EXAMPLE 1

Activity Assays for Galactose Oxidase Expressed in *E. coli*

This Example describes assays used for evaluating galactose oxidase activity. Galactose oxidase generates equimolar amounts of hydrogen peroxide by oxidation of a substrate. Colorimetric detection of hydrogen peroxide was therefore used to assay galactose oxidase activity, employing the following reaction scheme:

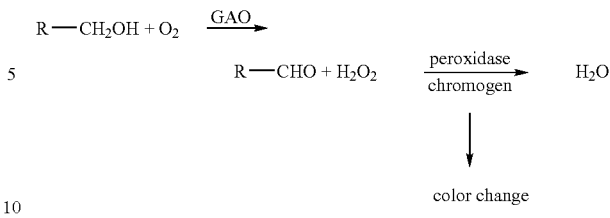

This system can be used to assay for oxidation of various substrates, with a very high sensitivity. In the reaction scheme above, an alcohol group of a substrate R is oxidized to produce an aldehyde and hydrogen peroxide ($H_2O_2$) is released. For example, D-galactose is converted to D-galactohexodialdose plus $H_2O_2$. The chromogen, in the presence of hydrogen peroxide and peroxidase enzyme, e.g. horseradish peroxidase (HRP), produces a detectable color change, indicating that the reaction catalyzed by GAO has occurred.

A. Test Tube Assay

The activity of galactose oxidase produced in *E. coli* was investigated using fungal galactose oxidase (Sigma, partially purified) as a standard. For detecting hydrogen peroxide with peroxidase (Sigma, type I from horseradish), a chromogen was selected for the GAO assays (85).

1. Materials

Cells. *E. Coli* DH5aMCR (Life Technologies) was used for gene manipulation. *E. coli* BL21(DE3) (Novagen) was used as a host strain for expression of galactose oxidase gene. *E. Coli* KY-14478 (SN0029, lacking catalase, Kyowa Hakko Kogyo, Co. Ltd.) was also used for manipulation and expression of genes (157). Competent cells for electroporation were prepared (147).

Cultivation Media. Luria-Bertani LB medium (10 g/l bacto tryptone, 5 g/l bacto yeast extract, 10 g/l NaCl, pH 7.5) was used mainly for cultivation of *E. Coli* (19). LB plates contained 15 g/l agar in LB medium. Ampicillin (100 mg/l) was added to the medium when required.

Buffers. Solutions of sodium phosphate, potassium phosphate and Tris-HCl at various pHs were tested as buffer solution for the assay.

Chromogens. Many aromatic compounds can be used as a chromogen for the assay. Four chromogens showed particularly strong color formation; green, orange, red and red, respectively: (a) 2,2'-azinobis(3-ethylbenzothiazoline-6-sulfonic acid) (ABTS) (85); (b) o-anisidine; (c) o-dianisidine (127, 123, 121, 122) and (d) o-tolidine (114, 119). Their peaks of absorbance were 410 nm, 490 nm, 460 nm and 420 nm.

2. Methods

Cultivation. Three steps of cultivation were performed for production of galactose oxidase. Recombinant *E. coli* strains were cultivated on LB plate containing ampicillin at 30° C. for 18 hours. The cells were inoculated to LB containing ampicillin. After cultivation at 30° C. for 12 hours, the culture was transfered to a new test tube containing 3 ml LB supplemented with ampicillin. The inoculation rate was 0.5% of medium. Isopropyl beta-D-thiogalactopyranoside (IPTG) (1 mM) was added for induction after cultivation at 30° C. for 7 hours. Cultivation was continued at 30° C. for 6 hours.

Permeabilization. Permeable cells were prepared by freezing (−20° C.)—thawing (4° C.) and treatment with 0.5 mg/l lysozyme (Sigma, from chicken egg white) for 30 minutes at 37° C. This pre-treatment for permeablization was used for assay in evaluation of recombinant galactose oxidase. (Example 3).

Activity assay. The extract was assayed for galactose oxidase activity. Copper (II) sulfate solution (0.4 mM) was added to the cell-free extract. The cell-free extract was diluted in the buffer solution. Peroxidase (Sigma, type I from horseradish) (10 units/ml) and azinobis(3-etlhylbenzothiazoline-6-sulfonic acid) (ABTS) (2 g/l) were added to the reaction solution. The reaction solution was pre-incubated at 37° C. for 5 minutes. Substrate was added to the solution to be 100 mM. The increase of absorbance (410 mm or 405 nm) was measured at 37° C. for 1 minute. Fungal galactose oxidase (Sigma, partially purified) was used as standard for estimation of the activity.

3. Results

From these experiments, ABTS was selected as a preferred chromogen for these types of assays, since ABTS formed its color most strongly and sensitively. Moreover, the highest assay sensitivity and lowest background was achieved when using a 100 mM sodium phosphate buffer solution (pH 7.0) for the assay.

Minimum detectable activity of galactose oxidase for this assay system was 0.05 units/ml. Galactose oxidase activity between 0.1 and 1 units/ml was measured quantitatively by photometer at 410 nm or 405 nm.

Catalase produced by $E.$ $coli$ degrades hydrogen peroxide and may influence the assay. In practice, catalase was not observed to pose a problem, because the activity of the galactose oxidase was greatly higher than that of catalase.

Provided below are additional galactose oxidase screening techniques and/or activity assays, having the following advantages: high specificity for galactose oxidase, high sensitivity, good reproducibility, quantitative measurements, simplicity, flexibility for many substrates, and low cost. One screening system utilizes microplates and the other utilizes membranes. Both systems applies horseradish peroxidase (type 1, Sigma) together with a chromogen (ABTS).

B. Microplate Screening Method

The following micro-plate assay has a high sensitivity. Moreover, the enzyme activity can be determined quantitatively. To increase throughput, the method can be automated, for example robotically. This method is particularly suitable as a second screen, after active clones are identified by a more rapid first screen, such as a membrane screen. In experiments using these procedures, the active cultures on the microplate had galactose oxidase activity as indicated by strong green color formation, where each positive well on the microplate was visible as a dark circle GAO activity was screened in 96-well plates.

Briefly, single colonies were picked from LB-Ampicillin (LB-Ap) agar plates into deep-well plates and grown in LB-Ap. The master plates were duplicated into new deep-well plates containing LB-Ap-1 mM IPTG. Following cultivation at 30° C., $CuSO_4$ was added and the cells were lysed with lysozyme and SDS. Cell extracts were reacted with galactose and allyl alcohol using the GAO-HRP coupled assay described above.

1. Methods for Approach A

Single colonies were picked from Luria-Bertani/100 µg/ml ampicillin (LB-Ap) agar plates into deep-well polypropylene plates (well depth: 2.4 cm; volume: 1 ml; from Beckton Dickinson Labware) and cells were grown for 10 h at 30° C. and 270 rpm in 200 µl LB-Ap. The master plates were duplicated by transferring a 10 µl aliquot to a new deep-well plate containing 300 µl LB-Ap and 1 mM isopropyl-beta-D-thiogalactopyranoside (IPTG) and grown for 12 h at 30° C. and 250 rpm. The cultures were then centrifuged for 10 min at 5000 rpm and the cell pellet was resuspended in 300 µl 100 mM sodium phosphate (NaPi) buffer, pH 7.0 containing 0.4 mM $CuSO_4$. Following addition of 0.5 mg/ml lysozyme (35 min at 37° C.) and 2.5% (w/v) SDS (overnight at 4° C.), the GAO activity was assayed using the GAO-horseradish peroxidase (HRP) coupled assay (85). Aliquots of the cell extracts were reacted with galactose (50 mM for generation A1 or 25 mM for generations A2 and A3) and allyl alcohol (0.5 M for all generations) at pH 7.0. The initial rate of $H_2O_2$ formation was followed by monitoring the HRP-catalyzed oxidation of 2,2'-azino-bis(3-ethylbenzthiazoline-6-sulfonic acid) (ABTS) at 405 nm. To assay thermostability, the plates were heated at a given temperature for 10 min, cooled down on ice for 10 min, and allowed to reach room temperature for ca. 5 min before the activity toward galactose was measured. The thermostability index was determined from the ratio of the residual GAO activity to the initial activity. Mutants identified as thermostable were then grown in test tubes (3 ml cultures) and the residual activity after heating at various temperatures was measured at room temperature.

2. Methods for Approach B

Single colonies were picked from LB-Ap agar plates into deep-well polypropylene plates (well depth: 4.4 cm; volume: 2.2 ml; from Qiagen) and cells were grown for 8 h at 30° C. and 270 rpm in 500 µl LB-Ap. The master plates were duplicated by transferring a 10 µl aliquot to a new deep-well plate containing 500 µl LB-Ap-1 mM IPTG and grown overnight at 30° C. and 270 rpm. An aliquot of the culture was transferred to a microtiter plate. Following addition of 0.5 mg/ml (30 min at 37° C.) and 0.4% (w/v) SDS –0.4 mM $CuSO_4$ in 100 mM NaPi buffer, pH 7.0 (4 h at 4° C.), the GAO activity was assayed using the GAO-HRP coupled assay as described above. The galactose concentration used was 25 mM (generations B1 and B2) or 10 mM (generations B3 and B4).

C. Membrane Screening Method

Although the micro-plate screening system is highly sensitivity and quantitative, it is desirable to provide a method that contemporaneously assay many more, e.g. thousands more clones in a sensitive, accurate, practical and efficient manner. Methods for detection of galactose oxidase activities directly from colonies on agar-plate were examined, but were found to exhibit relatively low sensitivity, low reproducibility, and very slow color formation. Hence, to evaluate very large number of mutants, methods for detection of their activities directly from colonies on agar-plate or from colonies transferred onto a membrane were examined. These methods were based on colorimetric detection using chromogen and peroxidase, as in the micro-plate screening system.

A suitable screening method using membranes was developed, as is shown here in one optimized form. After transformants formed colonies on an LB-Ap plate (100 mg/l at 30° C. for 18–24 hours), these colonies were transferred to a membrane, i.e. they were adsorbed onto the membrane and lifted. for cultivation, the membrane was placed on a new LB-Ap plate (100 mg/l) and was incubated at 30° C. till new colonies were formed on the membrane (6–12 hours). The membrane then was transferred to a new LB-Ap (100 mg/l) plate with 1 mM IPTG, at 30° C. for 6 hours, for induction. Then, the membrane was put on a filter paper at room temperature, containing lysozyme (0.5 mg/ml), D-galactose (100 mM), ABTS (2 mg/ml), peroxidase (10 units/ml) and $CuSO_4$ (0.4 mM). In experiments using these procedures, colonies which had galactose oxidase activities showed as deep purple on the filter paper. This simple method has suitable sensitivity and can be used to evaluate several thousands colonies on one membrane at once.

Several thousands colonies can be evaluate by the screening method with one membrane. This method can be used with an image analyzer, for quantitative determination of activity of each colony. Although the sensitivity of this method is not as high as others, the method is fast and is suitable for a first or initial screening, because many thousands or even millions of colonies can be contemporaneously or rapidly evaluated.

In a preferred embodiment, galactose oxidase activities of colonies which were transferred on a membrane were estimated directly. Colonies, which were formed on LB-Apicillin plate at 30° C. for 24 hours, were transferred onto a membrane (Immobilon NC (HATF), surfactant-free, 45 mm, 82 mm, Millipore). The membrane was put on a new LB-Apicillin plate and was kept at 30° C. for 6~12 hours till colonies were re-formed. Then the membrane was transferred onto an LB-Apicillin plate containing 1 mM IPTG and was incubated for 6 hours at 30° C. After the membrane was put on filter paper containing 0.5 mg/l lysozyme, 100 mM substrate, 2 mg/ml ABTS, 10 units/ml peroxidase and 0.4 mM $CuSO_4$ in 100 mM sodium phosphate buffer solution (pH 7.0), the membrane was kept at room temperature for one day, covered with a shield (ABTS is light sensitive). Active colonies showed deep purple color formations.

D. Assay Reagents and Conditions

Figure 3:
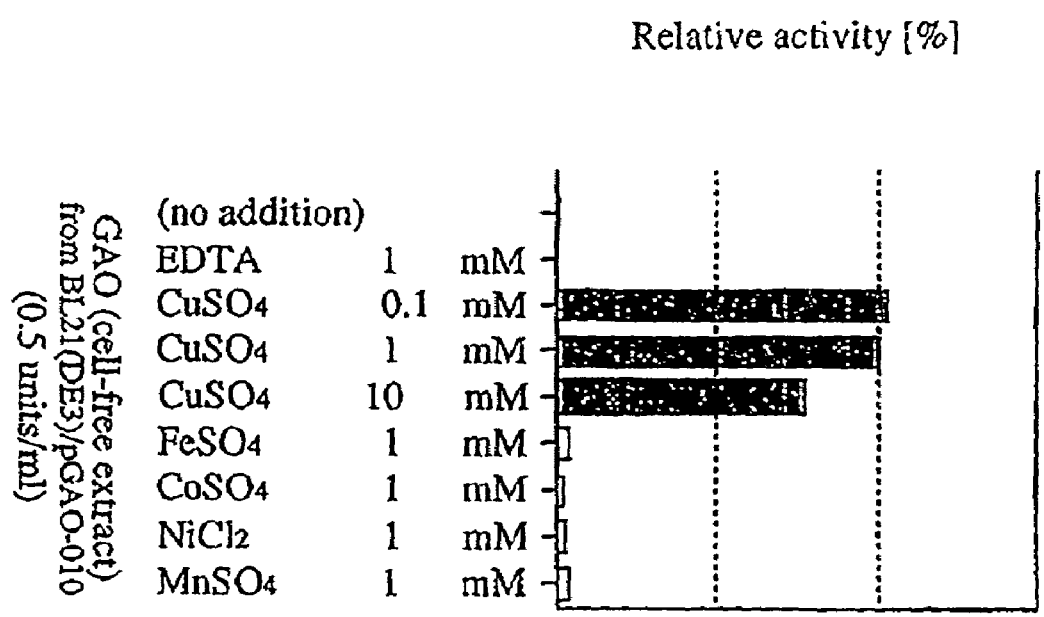
FIG. 3 is a graph showing the effect of metal ions (particularly copper ions) on the activity of a recombinant wild-type GAO, pGAO-010. Enzyme solutions with additives were kept at 4° C. for 1 hr before assay. Relative activity of enzyme solution with 1 mM copper (II) sulfate was estimated as 100%.

Some of the assays herein use $CuSO_4$, and/or SDS. Copper sulfate is used to provide copper (II) ion to activate the recombinant (mutant or variant) enzyme. The activity of partially purified galactose oxidase from *D. dendroides* (Sigma) was detected well by using peroxidase and ABTS as described; the addition of copper (II) ion and other cofactors was not needed. (The Sigma enzyme already includes copper ions.) However, experiments with cell-free extracts of recombinant GAO enzymes of the invention showed that almost no activity was detected in the absence of copper (II) ions. Thus, the presence of copper (II) ion is preferred, and without being bound by any theory, is believed to be essential, to activate recombinant GAO enzymes produced by *E. coli* as described herein. Treatment with copper ions at 4° C. is preferred. Copper ion can be provided as copper sulfate ($CuSO_4$). Experiments showed that 0.1 mM $CuSO_4$ is sufficient, whereas 10 mM $CuSO_4$ slightly inhibited GAO activity. Experiments under assay conditions showed that the preferred concentration of $CuSO_4$ for activating crude enzyme solution is 0.4 mM. The metal (II) ions of iron, cobalt, nickel, and manganese, and the metal chelator EDTA, did not affect activation of the recombinant GAO in experiments under assay conditions. Experimental results are shown in FIG. 3. under assay conditions, with and without various metal (II) ions or EDTA.

Detection enhancers. In certain assay embodiments, sodium azide or sodium sulfide may be added, for example in an amount of from about 0.01 mM to less than 1 mM. These reagents may enhance detection of GAO activity in some circumstances.

Detergents. Addition of detergents to the assay solution also increased the observed activity. Pretreatment with SDS was most effective for increasing the galactose oxidase activity. Treatment with SDS for longer than 12 hours at 4° C. after treatment with lysozyme was suitable for the assay. The galactose oxidase activity did not change within the treatment for 12 to 24 hours at 4° C. Cultivation, pretreatment and assay were done as described above.

Other detergents may also be used, as shown in TABLE 1. In these experiments, approximately 0.1 units/ml culture of *E. coli* BL21 (DE3)/pGAO-010 and 0.25 units of partially purified galactose oxidase (Sigma) were used. Cells were treated with 0.5 mg/ml lysozyme at 37° C. for 30 minutes. Enzyme and cells were treated with detergents at 4° C. for 1–12 hours. Galactose oxidase activities were assayed using the microplate method described above.

Cultivation. Activation on LB-Ap (100 mg/l) plate for 12~24 hours at 30° C. and seed-cultivation in LB-Ap (100 mg/l) 200–500 μl/well for 8–10 hours at 30° C. provided uniform growth for cultivation. These conditions are suitable if not necessary for the assay, using the cells, reactants and reagents in these experiments.

The addition of IPTG as an inducer was observed to be necessary for the expression of galactose oxidase on microplate cultivation in these experiments. Initial addition of IPTG to the medium was preferred to the addition of IPTG during cultivation. A cultivation time of 12–16 hours was preferred, and provided superior results (overall higher activities) for almost all recombinant *E. coli* which had a plasmid for expression of galactose oxidase in these experiments. The growth of cells was stopped before 16 hours and the cell extracts had almost no activity at 37° C. Cultivation at about 30° C. was the optimal temperature in these experiments.

TABLE 1

| SDS [% w/v] | Treatment | 0 | 0.00001 | 0.0001 | 0.001 | 0.01 | 0.1 |
|---|---|---|---|---|---|---|---|
| Relative activity of culture [%] | 4° C. 12 hr | 100[1] | 131 | 106 | 146 | 241 | 394 |
| Relative activity of culture [%] | 4° C. 1 hr | 100[2] | 96 | 118 | 134 | 146 | 189 |
| Relative activity of GAO[4] [%] | 4° C. 12 hr | 100[3] | 99 | 95 | 103 | 99 | 101 |
| Triton X-100 [% w/v] | Treatment | 0 | 0.00001 | 0.0001 | 0.001 | 0.01 | 1 |
| Relative activity of culture [%] | 4° C. 12 hr | 100[1] | 133 | 145 | 190 | 220 | 250 |
| Relative activity of culture [%] | 4° C. 1 hr | 100[2] | 85 | 95 | 123 | 118 | 149 |
| Relative activity of GAO [%] | 4° C. 12 hr | 100[3] | 114 | 114 | 109 | 108 | 98 |
| Tween 80 [% w/v] | Treatment | 0 | 0.00001 | 0.0001 | 0.001 | 0.01 | 1 |
| Relative activity of culture [%] | 4° C. 12 hr | 100[1] | 135 | 113 | 142 | 139 | 140 |
| Relative activity of culture [%] | 4° C. 1 hr | 100[2] | 159 | 125 | 144 | 122 | 139 |
| Relative activity of GAO [%] | 4° C. 12 hr | 100[3] | 120 | 113 | 106 | 114 | 102 |
| DMSO [% w/v] | Treatment | 0 | 0.00001 | 0.0001 | 0.001 | 0.01 | 1 |
| Relative activity of culture [%] | 4° C. 12 hr | 100[1] | 152 | 140 | 150 | 155 | 152 |
| Relative activity of culture [%] | 4° C. 1 hr | 100[2] | 169 | 106 | 116 | 116 | 96 |
| Relative activity of GAO [%] | 4° C. 12 hr | 100[3] | 104 | 107 | 103 | 97 | 99 |

([1]0.09 units/ml, [2]0.07 units/ml, [3]0.25 units/ml) [4]GAO obtained from SIGMA

EXAMPLE 2

Construction of Galactose Oxidase Plasmids

Plasmids were constructed to express galactose oxidase gene (gao) from *Fusarium* ssp. as described below. Several vectors were examined for high expression. Plasmids with different promoters and different sequences between the GAO gene and the ribosime binding site were constructed, as described. *Escherichia coli* strain BL21(DE3) and KY-14478 were transformed with these plasmids. Permable cells from test tube cultures were used for the assay.

A. Construction of Plasmids

1. Modified pUC18 Vector Plasmids

Figure 7:
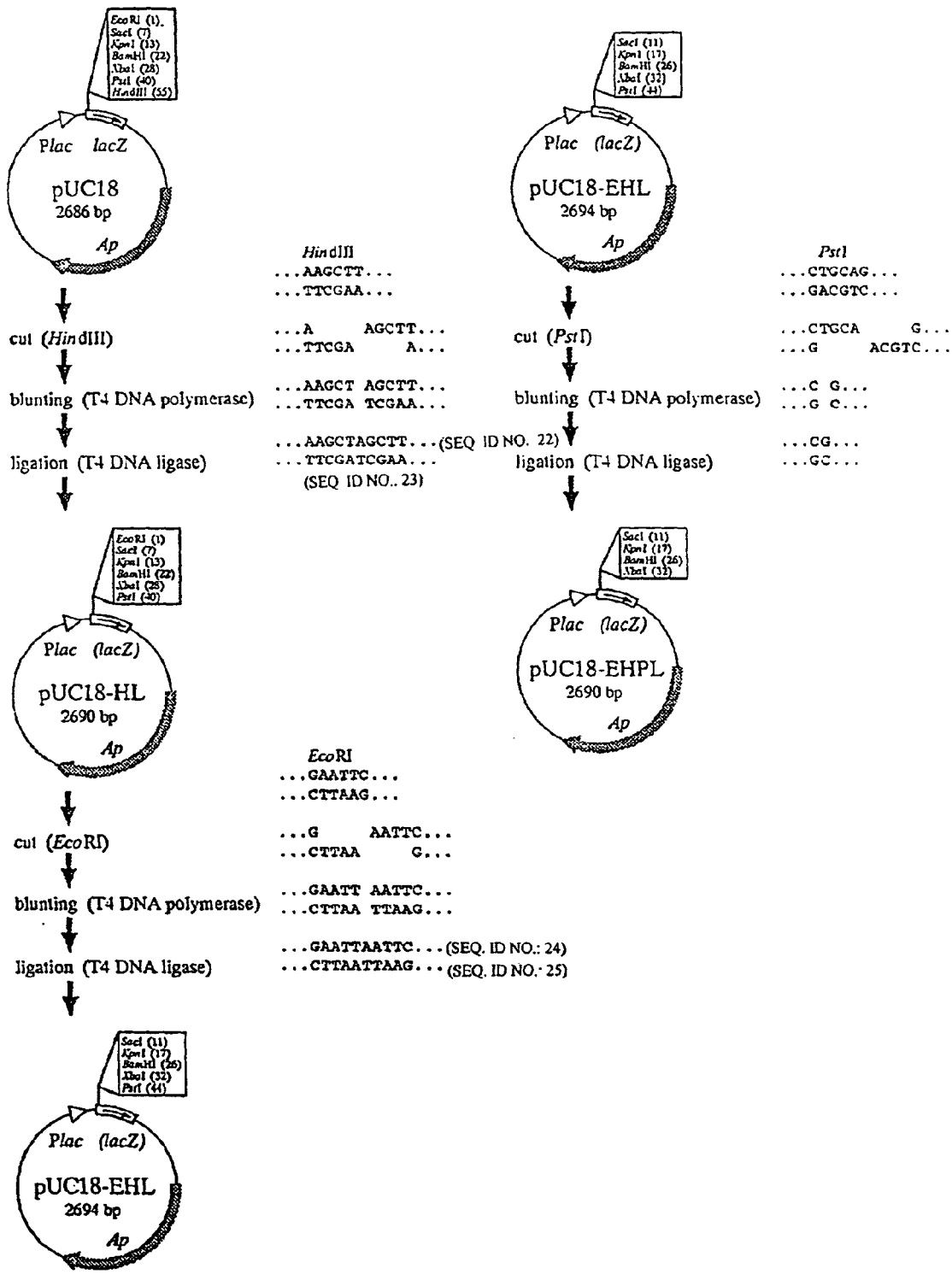
FIG. 7 is a schematic representation of the construction of plasmid pUC18-EHL.

Modified pUC18 plasmids were made to be used for constructing galactose oxidase expression plasmids. As shown in FIG. 7, vector pUC18 was digested with the restriction enzyme HindIII, blunted with T4 DNA polymerase and ligated with T4 DNA ligase to create vector pUC 18-HL lacking the HindIII site. pUC 18-HL was digested with EcoRI, blunted with T4 DNA polymerase and ligated with T4 DNA ligase to create vector pUC18-EHL lacking the EcoRI and HindIII sites. Similarly, pUC18-EHL was digested with PstI, blunted with T4 DNA polymerase and ligated with T4 DNA ligase to create vector pUC 18-EHPL, lacking the EcoRI, HindIII, and PstI sites.

2. GAO Vector Plasmids

Figure 8:
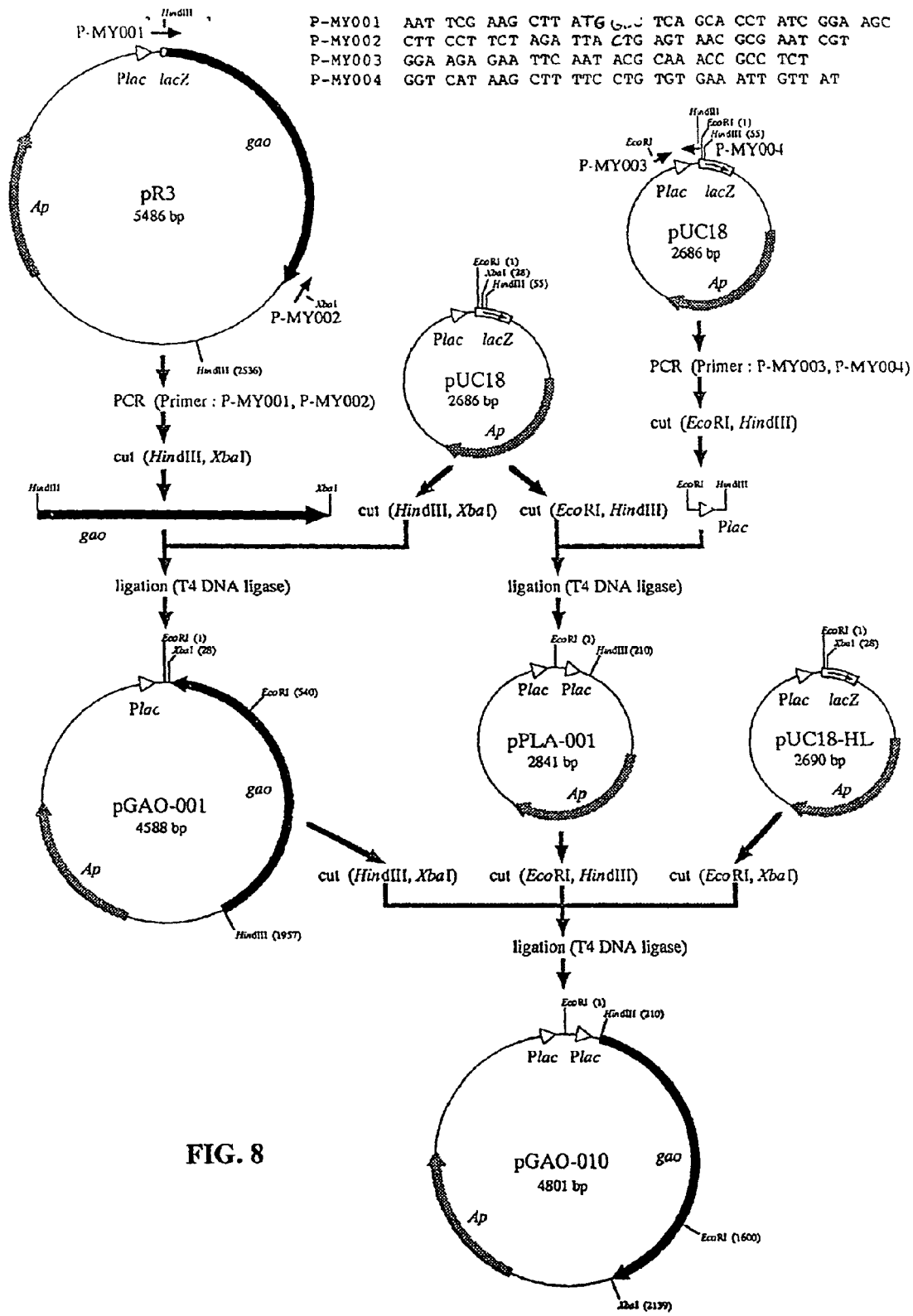
FIG. 8 is a schematic representation of the construction of plasmid pGAO-010.

As shown in FIG. 8, plasmid pGAO-010 expressing GAO was made using plasmid pR3. Plasmid pR3 contains the gene for mature galactose oxidase (GAO) fused to the 5' end of the IacZ fragment, and was obtained from Dr. Howard K. Kuramitsu (Dept. of Oral Biology, State University of New York, Buffalo, N.Y.). The GAO gene was amplified from pR3 by PCR using primers P-MY001 and P-MY002 in order to introduce a HindIII restriction site followed by an ATG initiation codon immediately upstream from the mature GAO sequence, and an XbaI site immediately downstream from the stop codon. (Primer sequences are shown in FIG. 6). The PCR product was digested with HindIII and XhaI and ligated into a similarly digested pUC18 vector to create pGAO-001. Plasmid pPLA-001 is a modified pUC18 vector containing a double lac promoter. The lac promoter from pUC18 was amplified using primers P-MY003 and P-MY004. The PCR product was digested with EcoRI and HindIII and ligated into a similarly digested pUC18 vector. Following digestion of pGAO-001 with HindIII and XbaI, pPLA-001 with EcoRI and HindIII, and pUC18-HL with EcoRI and XbaI, plasmid pGAO-010 was generated by ligation with T4-DNA ligase.

Figure 9:
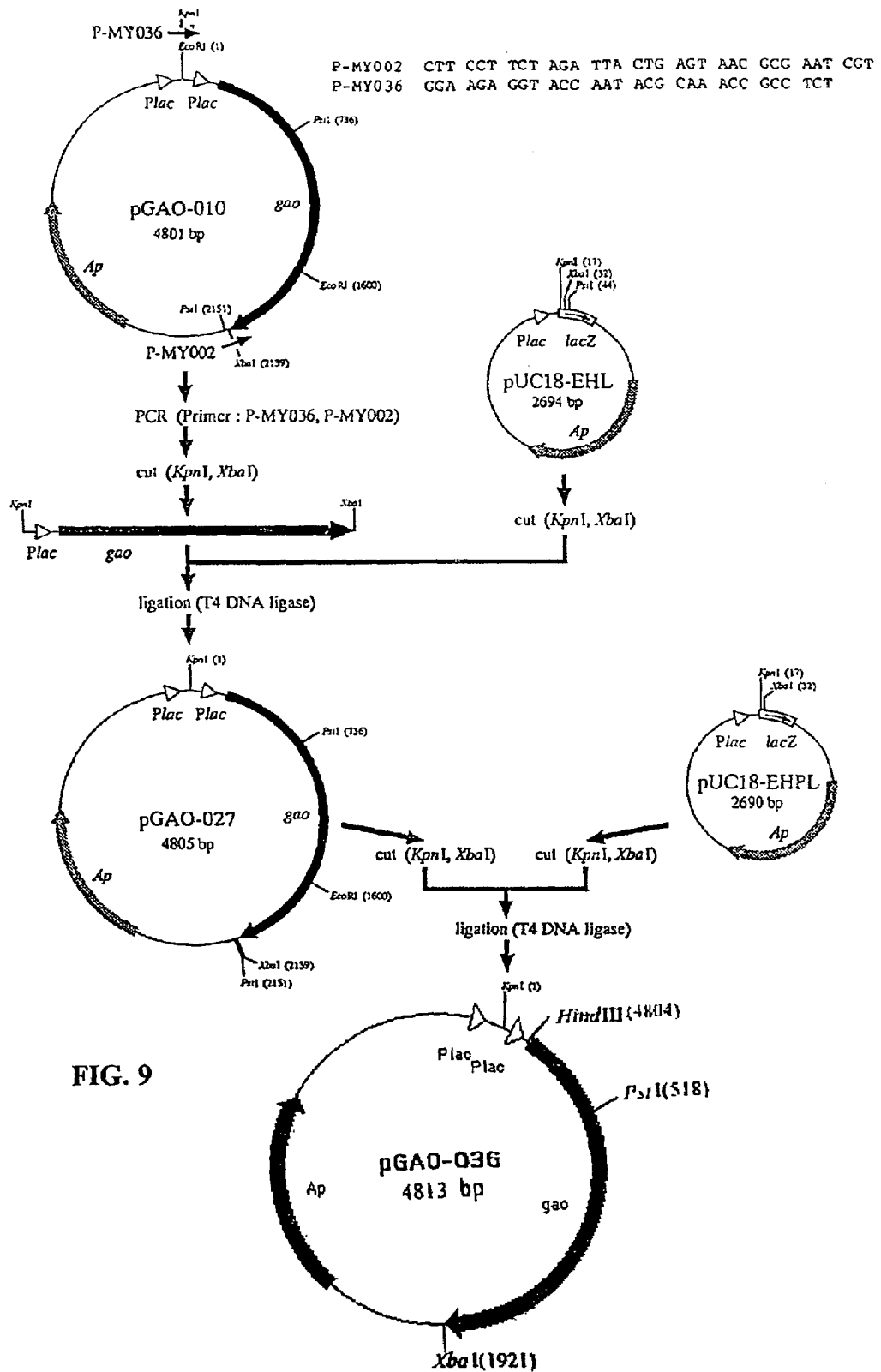
FIG. 9 is a schematic representation of the construction of plasmids pGAO-027 and pGAO-036.

Another plasmid, pGAO-036, was made by amplifying pGAO-010 using primers P-MY036 and P-MY002. FIG. 9. The PCR product was digested with KpnI and XbaI and ligated with a similarly digested pUC18-EHL to create plasmid pGAO-027. Plasmid pGAO-027 was digested with KpnI and XhaI and ligated with a similarly digested pUC18-EHPL to create plasmid pGAO-036. This plasmid contains a unique PstI site. Plasmid pGAO-036 was used as a for directed evolution experiments described herein.

Figure 10:
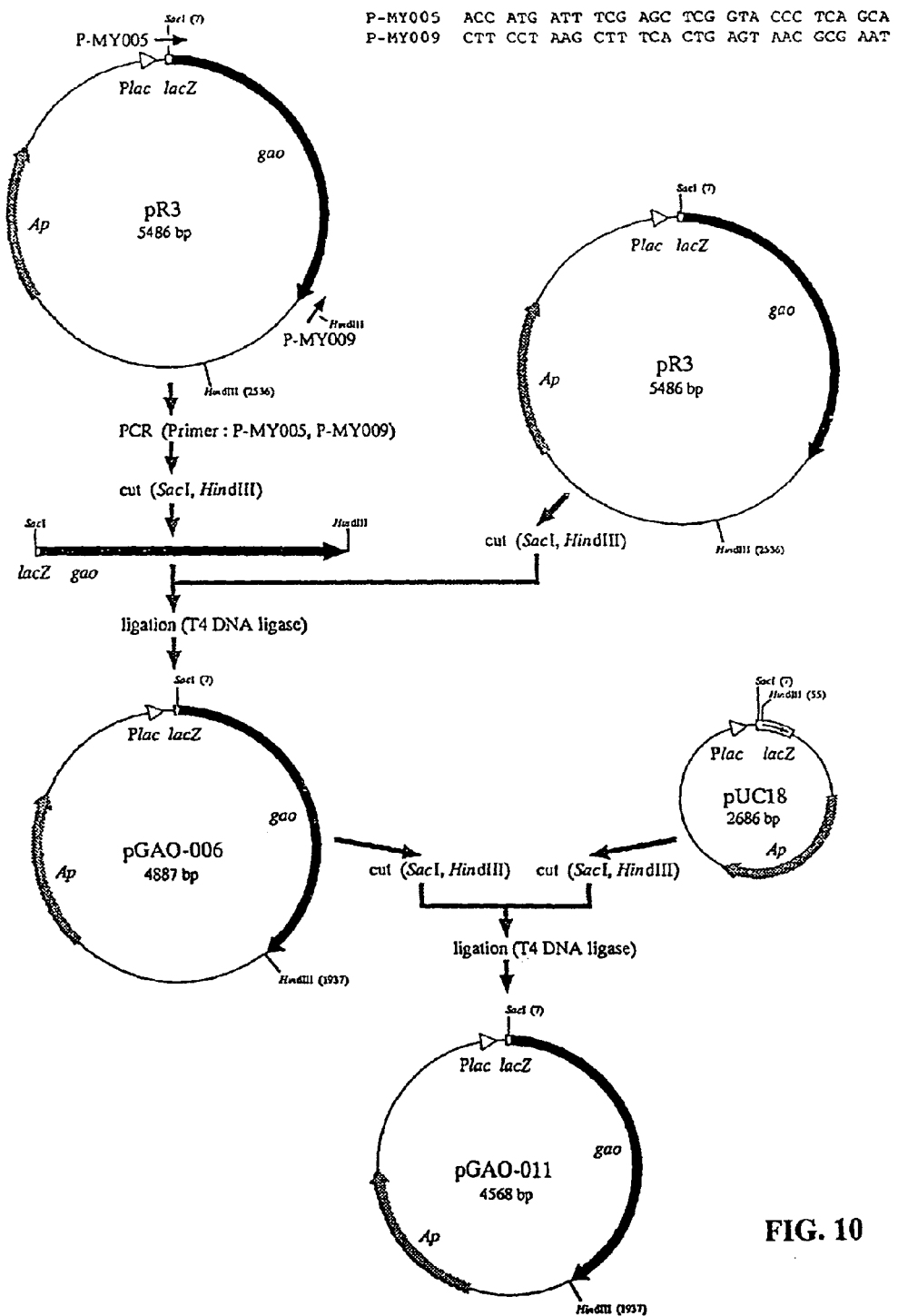
FIG. 10 is a schematic representation of the construction of plasmids pGAO-006 and pGAO-011.

Another plasmid, pGAO-011, was made using similar techniques, as shown in FIG. 10

B. Plasmids and transformation

Plasmids for expression of galactose oxidase were constructed as described above. The galactose oxidase enzyme was amplified from pR3 (*Fusarium* ssp.) by PCR. The lac promoter of pUC18 and T7 promoter of pET-22b(+) (Novagen) were used for expression. In addition to expression as mature sequence of galactose oxidase, expression of the gene as a fused protein with other peptides was examined. The N terminal sequence of LacZ was selected to express the galactose oxidase as a fused protein (127). PelB leader sequence was also used to produce galactose oxidase in periplasm. Furthermore, His-tag which is useful for purification of recombinant proteins was examined as an additional sequence of the C-terminal of galactose oxidase. T7 terminator sequence was used for stabilization of expression. Two different oris were chosen for replication of plasmid. The copy number of plasmid with ori from pUC series is higher than the plasmid with ori from pBR series.

In more detail, plasmids pUC18, pET-22b(+) (Novagen) and derivatives were used as vector plasmids. Galactose oxidase gene from *Fusarium* ssp. was amplified from pR3 according to known techniques. (110, 127). Genes were manipulated according to conventional methods using kits from Qiagen (Valencia, Calif.). The QIAprep Spin Miniprep Kit, QIAquick Gel Extraction Kit and QIAEX II Gel Extraction Kit, were used resepctively for purification of plasmids from cells, purification of DNA fragments and extraction of DNA fragments from agarose gel. *E. coli* DH5aMCR was transformed with plasmids by treatment with $CaCl_2$ (19). Electroporation was used for transformation of *E. coli* BL21(DE3) with plasmids (147, 148).

pUC18 and pET-22b(+) (Navagen) were used as vector plasmids. The gene of galactose oxidase from pR3 (127) was used. lac promoter from pUC18, tac promoter from pKK223-3 (Amercham Pharmacia Biotech) and T7 promoter from pET-22b(+) were selected for expression of the gene. The N terminal sequence of LacZ from pUC18, PelB leader, His-tag and T7 terminator sequences from pET-22b (+) were used for production of galactose oxidase. The gene and parts for expression were prepared by PCR. PCR was done in 100 ml of reaction solution containing PCR buffer (10 mM Tris-HCl, pH 8.5, 50 mM KCl, 2.5 mM $MgCl_2$, 0.01% gelatin), 1 ng of DNA as template, 50 p mole of each primers, 2.5 units of Taq DNA polymerase (Perkin Elmer) and 50 n mole of each dNTPs. DNA fragments were amplified in 30 cycles of 30 seconds at 94° C., 30 seconds at 50° C. and 60 seconds at 72° C. PCR products were purified by QIAquick PCR Purification Kit (Qiagen). Cutting and ligation of DNA by enzymes were according by "molecular cloning" (19). *E. coli* cells were transformed with plasmids by electroporation (Bio-Rad, gene Pulser). QIAprep Spin Miniprep Kit (Qiagen) was used for purification of plasmid from *E. coli* recombinant cells.

Using these strategies, plasmids were designed to produce the galactose oxidase gene. The plasmids were transformed to *E. coli* DH5aMCR, BL21(DE3) and KY-14478. Representative plasmids are shown diagrammatically in FIG. 11, according to the general scheme shown in FIG. 12.

Expression of the galactose oxidase gene in all constructed plasmids was controlled by the lac operator. Therefore, induction by isopropyl b-D-thiogalactopyranoside (IPTG) was necessary for production of the enzyme (FIG. 11). The expression of galactose oxidase was highest when IPTG (1 mM) was added after cultivation for 7 hours and cells were incubated for 6 more hours. Cultivation at 30° C. gave greatest activity of galactose oxidase per cultivation. Expression of the enzyme was remarkably decreased at 37° C. Lower temperatures than 27° C. were not suitable in the experiments because the cells grew very slowly.

Incubation on LB plate at 30° C. for 18 hours and pre-cultivation in LB at 30° C. for 12 hours stabilized the main cultivation. The optimal culture conditions were selected as shown above.

C. Galactose oxidase activity

Galactose oxidase activities of the recombinant E. coli were measured (FIG. 11). Some recombinant strains showed much higher activities than the recombinant plasmid pR3. These recombinants hold plasmids which were constructed with lac promoter and ori from pUC series. Some recombinant E. coli with plasmids, pGAO-018 and pGAO-023, expressing the galactose oxidase gene by T7 promoter did not grow well. Their galactose oxidase activities were not detected. Although some recombinants holding plasmid with T7 promoter, pGAO-008 and pGAO-009, grow normally, they showed low galactose oxidase activity. From these results, lac promoter was suitable for expression of galactose oxidase gene. Furthermore, double lac promoter seemed to be stronger than single lac promoter in some but not all cases.

Figures 12, 13:
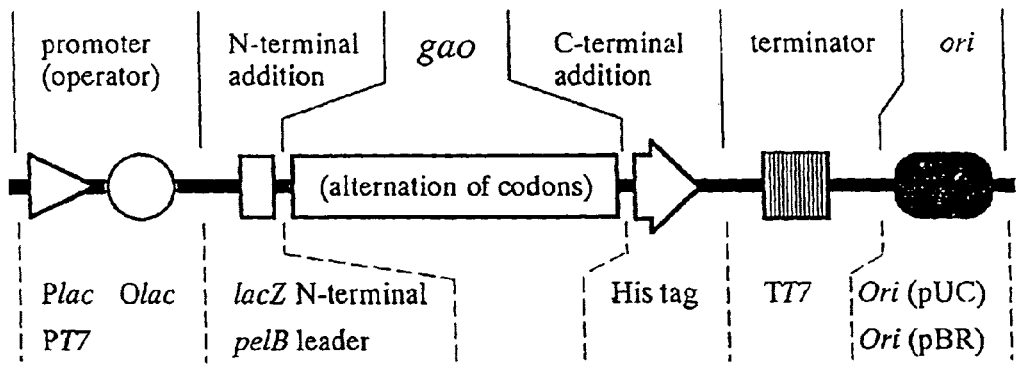
FIG. 12 shows a scheme for the design of plasmids according to the invention.
FIG. 13 shows the structures and activities of additional plasmids encoding GAO according to the invention, with IPTG-induced expression in host E. coli.

For example, plasmid pGAO-025 was designed to have double lac promoter and lacZ-gao fused gene (FIG. 13). However, galactose oxidase activity of a recombinant with pGAO-025 was almost the same as a recombinant with pGAO-011 which had a single lac promoter in KY-1447 cells but was more active than pGAO-011 in BL21(DE3) cells. Triple lac promoter was also examined to express the galactose oxidase gene. The effect of triple promoter was about the same as double promoter, e.g. in pGAO-028 and pGAO-010 (FIGS. 15 and 17), Galactose oxidase which was fused with the N-terminal sequence of LacZ or PelB leader was produced, as well as non-fused proteins. The activity of galactose oxidase fused with PelB leader was not detected without a pre-treatment of cells. Detection of activity of the enzyme required same the pre-treatment of recombinant cells as others. In these experiments GAO was not secreted in the medium, although a secretion signal sequence was present.

Plasmids pGAO-003 and pGAO-005 were designed to produce galactose oxidase in fused form with His-tag at its C-terminal. No galactose oxidase activity was detected from recombinant strains with these plasmids.

Terminator sequence sometimes stabilizes gene expression. In these experiments, introduction of T7 terminator sequence apparently did not increase GAO expression. Compare pGAO-020 with pGAO-010 or pGAO-022 with pGAO-017.

E. coli DH5aMCR expressed the galactose oxidase gene with these plasmids. However their activities were lower then that of recombinant strains of E. coli BL21(DE3) and E. coli KY-14478 (data not shown). E. Coli BL21(DE3) and E. Coli KY-14478 with plasmid pGAO-010 or pGAO-027 successfully expressed galactose oxidase in high activity. These two plasmids have the same sequence except for one restriction endonuclease site in the vector sequence. Their structure is suitable to express the galactose oxidase in a mature fungal sequence. Consequently, E. coli BL21 (DE3) and E. coli KY-14478 harvesting plasmid pGAO-010, pGAO-027 or their derivatives were used for continued experiments.

D. Codon Alternation

Codon alternation of the N-terminal sequence of a gene, without changing the peptide sequence, may cause higher expression of the gene in some cases. Codons of six N-terminal amino acid residues of galactose oxidase were exchanged randomly by PCR with a mixed primer, with the following alternations.

|  |  |  |  |  |  |  |  |  |  | SEQ ID NO: |
|---|---|---|---|---|---|---|---|---|---|---|
|  | (M) | A | S | A | P | I | G | S | A | 26 |
| Wild-type sequence | ATG | GCC | TCA | GCA | CCT | ATC | GGA | AGC | GCC ... | 27 |
| Random Alternation | --- | --N | --N | --N | --N | --A | --N | --- | --- ... | 28 |
|  |  |  | T |  |  |  |  |  |  |  |
|  |  |  | C |  |  |  |  |  |  |  |

Figure 14:
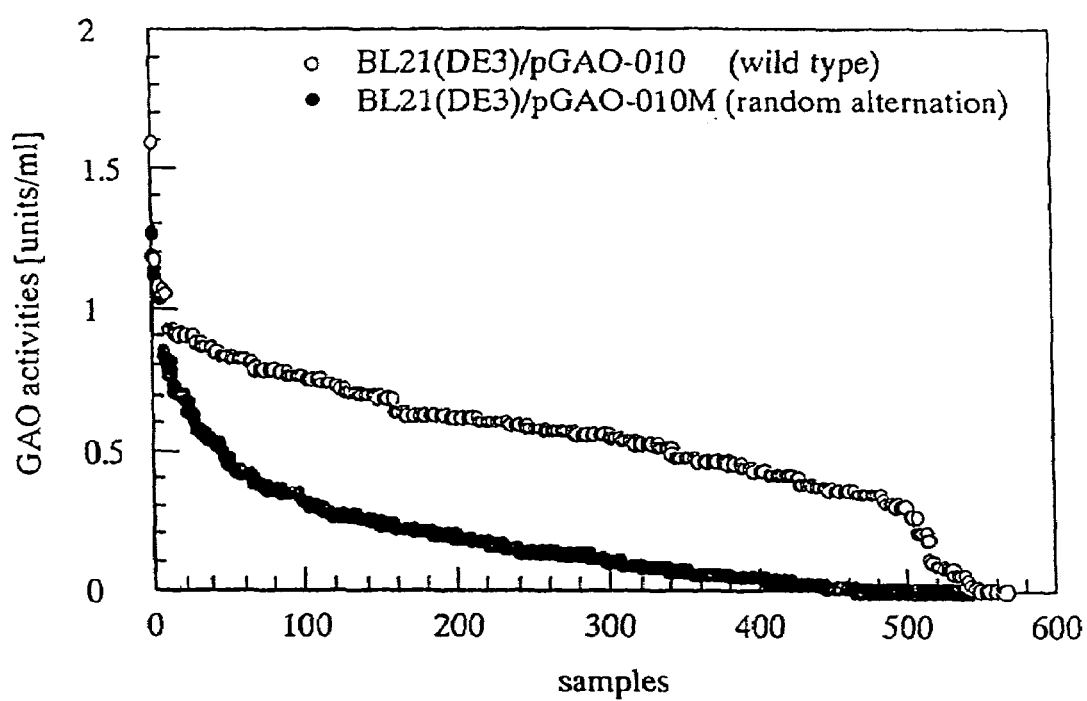
FIG. 14 is a graph comparing the GAO activities of GAO plasmids with and without random codon alternation.

The galactose oxidase gene of pGAO-010 was replaced with PCR products comprising the galactose oxidase gene with random codon alternation. The plasmids of this library were named pGAO-010M. This random codon alternation of the N-terminal sequence did not cause higher expression (FIG. 14), and in many cases GAO activity was reduced. No significant difference was observed when E. coli KY-14478 was used as a host strain, compared with E. coli BL21(DE3).

E. Optimization of Upper Sequence of gao

The region between the Shine-Dalgarno ("SD") sequence AGGA and the initiation codon, ATG, is sensitive for efficient RNA translation and has a significant influence on expression of gene. One to three bases were inserted between SD of the lac promoter and the ATG of the galactose oxidase gene in pGAO-027 to investigate the impact of altering the distance between SD and ATG. A change in the length of the region between SD and ATG causes a decrease in galactose oxidase activity when E. coli BL21(DE3) was used as a host strain (TABLE 2; SEQ ID NOS: 29–36). The original sequence of pGAO-027 or the one-base extended sequence of pGAO-029 were preferred for expression of the gene. When E. coli KY-14478 was used as a host strain one or two bases extension of the sequence between SD and ATG were preferred to express the gene

TABLE 2

|  |  |  | GAO Activity (units/ml) | |
|---|---|---|---|---|
| Plasmid* | Sequence between SD and ATG | Promoter | BL21(DE3) | KY-14478 |
| 027 | ...AGGAAAAGCTTATG... | Plac | 19.0 | 12.5 |
| 029 | ...AGGAAAAAGCTTATG... |  | 19.1 | 15.7 |

TABLE 2-continued

| Plasmid* | Sequence between SD and ATG | Promoter | GAO Activity (units/ml) BL21(DE3) | GAO Activity (units/ml) KY-14478 |
|---|---|---|---|---|
| 030 | ...AGGAAACAAGCTTATG... | | 16.3 | 15.9 |
| 031 | ...AGGAACAAAGCTTATG... | | 14.3 | 13.1 |
| 032 | ...AGGAAAAGCTTATG... | Ptac | 30.6 | 52.4 |
| 033 | ...AGGAAAAAGCTTATG... | | 25.7 | 56.2 |
| 034 | ...AGGAAACAAGCTTATG... | | 34.6 | 49.8 |
| 035 | ...AGGAACAAAGCTTATG... | | 22.1 | 38.7 |

*Plasmids are designated pGAO-XXX, where XXX is 027 through 035

The tac promoter often if not usually expresses genes at higher levels than lac promoter. tac promoter was prepared from pKK223-3 (Amercham Pharmacia Biotech) by PCR. lac promoters of plasmids, pGAO-027, pGAO-29, pGAO-030 and pGAO-031 were replaced with lac promoter. Recombinant strains with plasmids using tac promoter for expression showed approximately twice as much activity than the recombinant strains using lac promoter (TABLE 3). The optimal distance between SD and ATG under the tac promoter was almost the same as that under the lac promoter in both *E. coli* strains.

Recombinant strains *E. coli* BL21(DE3)/pGAO-034 and *E. coli* KY-14478/pGAO-033 were considered to be good for expression of galactose oxidase. Optimal culture conditions for these strains were as described above.

F. Properties of Recombinant Galactose Oxidase

Galactose oxidase from *Dactylium dendroides* (*Fusarium* ssp.) and the enzyme from recombinant *E. coli* BL21(DE3)/pGAO-010 differs only in glycosilation; their amino acid sequences are identical.

Substrate specificities of recombinant galactose oxidase from *E. coli* and the enzyme from fungi were compared. Cell-free extract of *E. coli* BL21(DE3)/pGAO-010 was used as a crude recombinant enzyme from *E. coli*. Partially purified galactose oxidase from *Dactylium dendroides* (Sigma, partially purified) was used as fungal enzyme. Substrate specificities of these two enzymes were almost same (FIG. 15).

EXAMPLE 3

Optimization of error-prone PCR conditions

A. General PCR Conditions

Mutation of the galactose oxidase gene (gao) was induced by error-prone PCR and according to known techniques (66, 129–133, 136–139). Wild type gao on pGAO-027 was replaced by the PCR products which were mutant galactose oxidase genes. The resultant plasmids were named as pGAO-027M. *E. coli* BL21(DE3) was transformed with these plasmids. Almost all transformants carrying error prone PCR products instead of wild type gao lost their galactose oxidase activities (FIG. 7). Mutations were induced on the whole galactose oxidase gene by error-prone PCR, using conditions "A" of TABLE 3.228 clones were selected randomly from each set of conditions with different manganese concentrations. These clones were cultivated and assayed with micro-plates. More than 65% of transformants lost their galactose oxidase activity, even though manganese ions were not added to the PCR solution.

Figure 5:
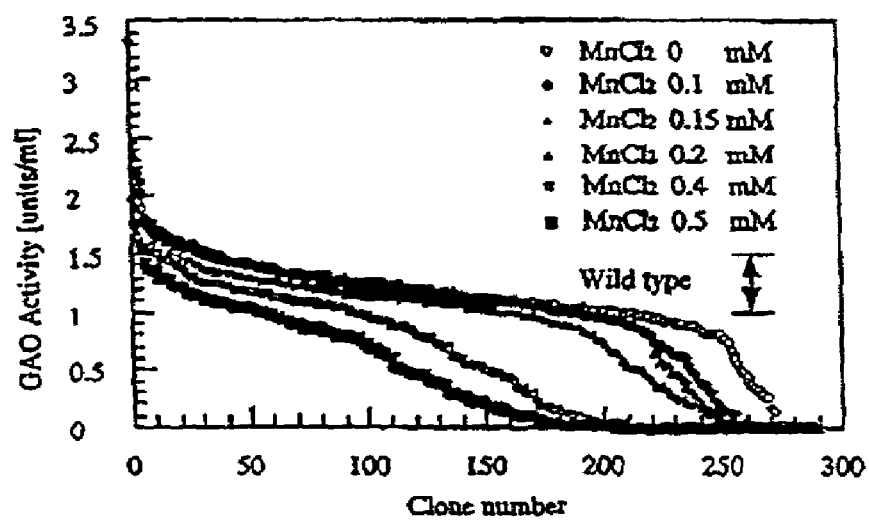
FIG. 5 is a graph showing GAO activity for various clones generated by error-prone PCR, with varying concentrations of $MnCl_2$ using conditions C of TABLE 3.

Various reaction conditions for error-prone PCR were compared, and in particular milder conditions were examined for mutation of the galactose oxidase gene. Conditions "A" and "C" are the previous conditions of error-prone PCR (above) and normal PCR conditions, respectively. The use of a buffer solution for error-prone PCR (Buffer EP) increased the error rate. Non-uniform composition of dNTPs for error-prone PCR (dNTPs EP) induced mutations in a higher rate than uniform composition of dNTPs for normal PCR (dNTPs normal). Taq DNA polymerase from Promega Corporation showed a higher error rate than the enzyme from Perkin Elmer. Since the rate of inactivation was 31% at most in condition "C" (FIG. 5), induction of mutation was not optimal, and may have been insufficient. In FIG. 5, mutations were induced in the whole galactose oxidase gene by error-prone PCR using conditions "C" of TABLE 3. Activities of 288 clones from each set of conditions with different manganese concentration were estimated using micro-plate screening.

From the alternatives examined in these experiments, Error-prone PCR condition "F" had a suitable frequency of error and was selected to induce mutation on the galactose oxidase gene in further experiments. The composition of buffer solution, the content of dNTPs and thermophilic DNA polymerase each affected the rate of mutation. For example, the difference between the buffer solution for normal PCR and the buffer solution for error-prone PCR was that the EP buffer contained gelatin. Since gelatin is not expected to influence the error rate of the PCR reaction, the observed rate difference may be due to a small difference in the final pH of reaction mixtures with these buffer solutions. More error was induced by non-uniform content of dNTPs for error-prone PCR than uniform content of dNTPs for normal PCR. Selection of the thermophilic DNA polymerase can be significant when optimizing an error-prone PCR experiment, as the particular polymerase may influence the mutation rate.

PCR conditions selected for mutation of the whole galactose oxidase gene in these experiments was milder than previously disclosed conditions (66, 129–133, 136–139). When the PCR conditions described previously were used for error-prone PCR of galactose oxidase gene, the mutation rate was too high, resulting in too many inactive or low activity clones. This result may be related to the fact that the galactose oxidase gene is as much as twice as large as genes previously used for error-prone PCR in the literature. Without being bound by any theory, deadly mutations may be induced more frequently as the target gene becomes larger.

In TABLE 3, 96 of 288 clones were selected randomly from each library. Their galactose oxidase activities were estimated by micro-plate screening method. Rates of clones which lost their galactose oxidase activities are show in the table.

Figure 4:
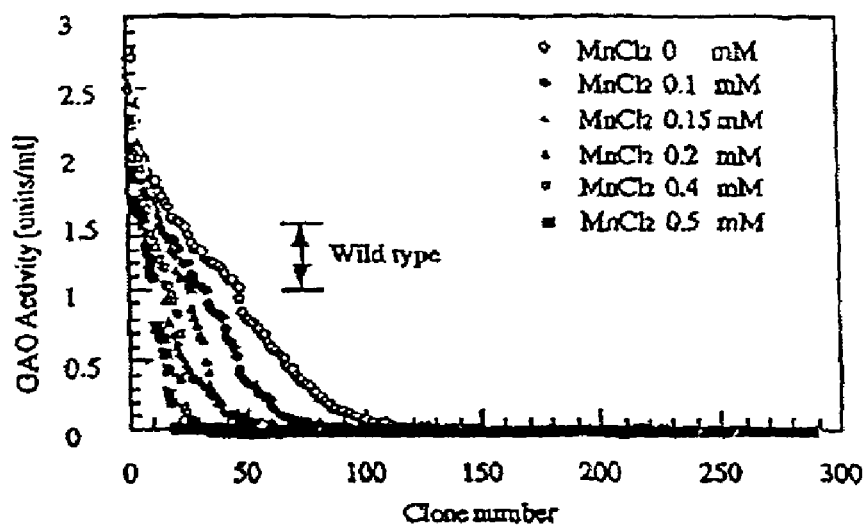
FIG. 4 is a graph showing GAO activity for various clones generated by error-prone PCR, with varying concentrations of $MnCl_2$, using conditions A of TABLE 3.

FIG. 4 and FIG. 5 show the effect of varying amounts of $MnCl_2$ in these experiments.

In the mutagenesis methods used herein, the error rate is from 1–6 mutations per polynucleotide, preferably 4–6, and most preferably 6. In certain embodiments with more than one round of directed evolution, the error rate may be different from one round to another. For example, the error rate may be about 1–2 mutations per polynucleotide in one round (e.g. a first round), and may be about 4–6 mutations per polynucleotide in another round (e.g. a second round).

(45) have been performed (generations B1 through B4). *E. coli* strain BL21(DE3) (Novagen) was used for the expression of GAO.

1. Approach A

Error-prone PCR was carried out in a 100 µl reaction mixture containing about 0.3 µg plasmid DNA as template, 30 pmol of each primer, 0.2 mM dGTP, 0.2 mM dATP, 1 mM dCTP, 1 mM dTTP, 7 mM $MgCl_2$, 0.1 mM $MnCl_2$, and 2.5 U Taq polymerase (Perkin Elmer) in 10 mM Tris-HCl, 50 mM KCl buffer, pH 8.5. PCR conditions were as follows: 30 cycles of 94° C. for 30 seconds, 50° C. for 30 seconds and 72° C. for 60 seconds. The percentage of inactive clones was between 30 and 50%.

StEP recombination of the four improved variants identified in generation A2 was performed in a 100 µl reaction mixture containing about 0.3 mg (total) plasmid DNA as template (prepared by mixing equal amounts of all four

TABLE 3

| | PCR conditions | | | | Inactivated clones [%] | | | | | |
|---|---|---|---|---|---|---|---|---|---|---|
| Buffer | $MgCl_2$ | dNTPs | TaqDNA polymerase | | $MnCl_2$ 0 mM | $MnCl_2$ 0.1 mM | $MnCl_2$ 0.15 mM | $MnCl_2$ 0.2 mM | $MnCl_2$ 0.4 mM | $MnCl_2$ 0.5 mM |
| A EP | 7 mM | EP | Promega | 50 u/ml | 60 (173/288) | 69 (199/288) | 77 (223/288) | 76 (220/288) | 90 (258/288) | 94 (270/288) |
| B EP | 7 mM | normal | Promega | 50 u/ml | 55 (53/96) | 61 (59/96) | | | | |
| C normal | 2.5 mM | normal | Perkin Elmer | 25 u/ml | 3 (3/96) | 10 (10/96) | | | | |
| | | | | | 5 (14/288) | 9 (27/288) | 10 (29/288) | 11 (31/288) | 28 (81/288) | 31 (90/288) |
| D EP | 7 mM | EP | Perkin Elmer | 25 u/ml | 45 (43/96) | 61 (59/96) | | | | |
| E EP | 7 mM | EP | Perkin Elmer | 50 u/ml | 39 (37/96) | 52 (50/96) | | | | |
| F normal | 7 mM | EP | Perkin Elmer | 25 u/ml | 23 (22/96) | 41 (22/96) | | | | |
| G normal | 7 mM | EP | Promega | 50 u/ml | 41 (39/96) | 52 (50/96) | | | | |
| H EP | 7 mM | normal | Promega | 50 u/ml | 51 (49/96) | 61 (59/96) | | | | |

Buffer EP: (× 10) 500 mM KCl, 100 mM Tris-HCl (pH 8.3), 0.1% (w/v) gelatin
Buffer (normal): (× 10) 500 mM KCl, 100 mM Tris-HCl (pH 8.3)
dNTPs EP: 0.2 mM dGTP, 0.2 mM dATP, 1 mM dCTP, 1 mM dTTP
dNTPs (normal): 0.5 mM dGTP, 0.5 mM dATP, 0.5 mM dCTP, 0.5 mM dTTP

EXAMPLE 4

Production of Galactose Oxidase Mutants

The directed evolution of galactose oxidase (GAO) is described. GAO variants with increased activity toward allyl alcohol and D-galactose and increased thermostability relative to wild-type have been identified.

A. Construction of GAO Mutant Libraries

Plasmid pGAO-036, expressing wild-type GAO, was used as the parent for the directed evolution of GAO (FIG. 9).

Two strategies have been followed for the directed evolution of the enzyme: (A) mutagenesis of the whole GAO gene (bases 1–1917) and (B) mutagenesis of part of the GAO gene (bases 518–1917). In Approach A, two rounds of error-prone PCR (45) have been performed (generations A1 and A2), followed by one round of StEP recombination (generation A3) (139) of four improved variants identified in library A2. In Approach B, four rounds of error-prone PCR plasmids), 10 pmol of each primer, 0.5 mM of each dNTP, 2.5 mM $MgCl_2$, and 5 U Taq polymerase (Perkin Elmer) in 10 mM Tris-HCl, 50 mM KCl buffer, pH 8.5. PCR conditions were 95° C. for 3 minuntes and 100 cycles of 94° C. for 30 seconds and 58° C. for 10 seconds. The primers used for error-prone PCR and StEP were: 5'-AATTCGAAGCT-TATGGCCTCAGCACCTATCGGAAGC-3' (forward) [SEQ. ID. NO. 1] and 5'-CTTCCTTCTAGATTACTGAG-TAACGCGAATCGT-3' (reverse) [SEQ. ID. NO. 2].

2. Approach B

Error-prone PCR was carried out in a 100 µl reaction mixture containing 10 ng plasmid DNA as template, 50 pmol of each primer, 0.2 mM of each dNTP, 7 mM (generations B1 and B2) or 4 mM $MgCl_2$ (generations B3 and B4), and 5 U Taq polymerase (Boehringer Mannheim) in 10 mM Tris-HCl, 50 mM KCl buffer, pH 8.3. PCR conditions were as follows: 94° C. for 2 minutes and 25 cycles of 94° C. for 30 seconds, 58° C. for 30 seconds and 72° C. for 60 seconds. The primers used were: 5'-TTGTTCCTGCGGCTGCAG-CAATTGAACCG-3' (forward) [SEQ. ID. NO. 8] and 5'-TGCCGGTCGACTCTAGATTACTGAGTAACG-3' (reverse) [SEQ. ID. NO. 9]. The percentage of inactive clones was between 30 and 40%.

B. Screening of GAO Libraries

GAO activity was screened in 96-well plates, using the methods of Approaches A and B, respectively, as described in Example 1(D).

C. Laboratory Evolution of GAO

Figure 16:
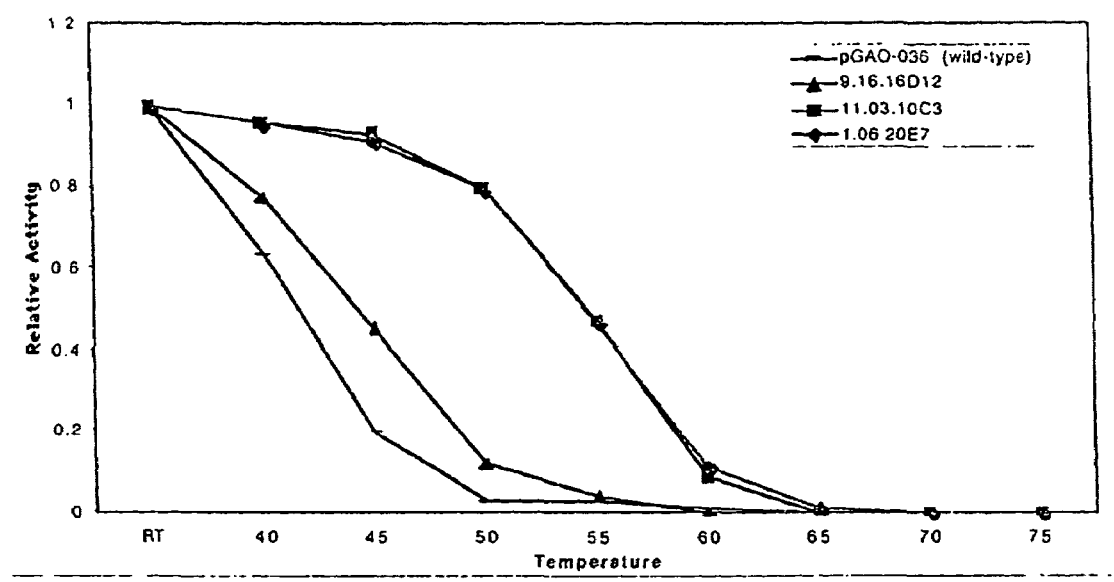
FIG. 16 is a graph showing the thermal stability of selected GAO mutants.

The thermal stability curves of selected GAO variants are shown in FIG. 16. Variants were grown in test tubes (3 ml cultures). Following centrifugation and resuspension of the cell pellets in NaPi buffer, pH 7.0 containing $CuSO_4$, the cells were lysed. Aliquots of the cell extracts were heated at each temperature for 10 min and then cooled down on ice for 10 min before the residual activity toward D-galactose was determined at room temperature.

Results of the laboratory evolution of GAO to increase activity and thermostability are listed in TABLE 4. $T_{50}$ is an operational measure of stability and is defined as the temperature at which the enzyme loses 50% of its activity following incubation for a set time. Wild type GAO (pGAO-036) was used as the parent for generation A1 of GAO variants. After screening about 1500 clones, three mutants, 9.16.8D2, 9.16.6C11 and 9.16.16D12, were identified as more active toward allyl alcohol and/or galactose. Clone 9.16.16D12, which was also more thermostable than wild-type GAO, was used to parent generation A2 of GAO variants. Four improved mutants were identified in this library following screening of about 1500 clones: 11.03.6D3, 11.03.10C3, 11.03.10D6 and 11.03.13E12. These clones were more active than the parent toward allyl alcohol and galactose. Clone 11.03.10C3 was substantially more thermostable than the parent, as well. These four improved variants were recombined by StEP in generation A3. Screening of about 2000 clones led to the identification of variant 1.06.20E7 which shows about a 200-fold increased activity toward allyl alcohol and D-galactose and exhibits about a 12° C. higher $T_{50}$ with respect to wild-type GAO.

Wild-type GAO (pGAO-036) was used as the parent for generation B1 of GAO variants. After screening about 900 clones, variant 1.D4 was identified as more active toward galactose and used to parent generation B2. Mutant 2.G4 was identified as more active toward galactose in this library following screening of about 1500 clones. Library B3 of GAO variants was generated using 2.G4 as the parent, and clone 3.H7 was identified as an improved variant after screening about 1500 clones. Finally, library 4B was created using 3.H7 as the parent and about 1500 clones were screened. Variant 4.F12 was identified as about 15-fold more active toward galactose relative to wild-type GAO.

D. Active and Thermostable Mutations

Most beneficial mutations occur in domains II and III of the GAO gene (residues 156–532 and 533–639, respectively) (87). Mutation V494A, which was identified several times in the screen, is located at the bottom of the active site adjacent to the copper ligand Y495. Its presence increases the binding affinity for galactose approximately 3-fold. N535D is found in a solvent-exposed loop in domain III. The amino acid substitution G195E is largely responsible for the observed increase in thermostability of variant 1.06.20E7 relative to wild-type. See FIG. 16 and TABLE 4.

It should also be noted that a large number of mutations (five in these experiments) resulted from the substitution of a neutral residue by a negatively charged residue. This tends to decrease the isoelectric point of GAO in the mutants (the pI of wild type GAO is 12). A decrease in pI is advantageous, in that it may lead to fewer interactions between the mutant GAO and other macromolecules, and lower adhesion to glass. It may also permit increased use of crude galactose oxidase preparations in organic synthesis (107).

TABLE 4

Mutations identified in GAO variants and their effects on GAO properties.

| GEN | GAO name | nucleotide base substitution | amino acid substitution | relative activity for allyl alcohol* | relative activity for D-galactose | $T_{50}$ (° C.) |
|---|---|---|---|---|---|---|
| 0 | pGAO-036 | N/A (WT) | N/A (WT) | 1.0 | 1.0 | 42 |
| A1 | 9.16.8D2 | A1609G | N537D | 2.6 | 4.6 | |
| A1 | 9.16.6C11 | T1481C<br>T1543A | V494A<br>C515S | 2.8 | 1.3 | |
| A1 | 9.16.16D12 | T1481C<br>T408C | V494A<br>P136 | 3.0 | 4.9 | 44 |
| A2 | 11.03.6D3 | T1481C<br>T408C<br>T28C | V494A<br>P136<br>S10P | 6.4 | 11 | |
| A2 | 11.03.10C3 | T1481C<br>T408C<br>G584A<br>A9C | V494A<br>P136<br>G195E<br>A3 | 3.8 | 9.6 | 54 |
| A2 | 11.02.10D6 | T1481C<br>T408C<br>A936G<br>A1603G<br>T654C | V494A<br>P136<br>L312<br>N535D<br>T218 | 5.4 | 11 | |
| A2 | 11.03.13E12 | T1481C<br>T408C<br>A208G | V494A<br>P136<br>M70V | 5.1 | 9.1 | |
| A3 | 1.06.20E7 | T1481C<br>T28C<br>T408C<br>A208G<br>G584A<br>A1603G | V494A<br>S10P<br>P136<br>M70V<br>G195E<br>N535D | 20 | 55 | 54 |

TABLE 4-continued

Mutations identified in GAO variants and their effects on GAO properties.

| GEN | GAO name | nucleotide base substitution | amino acid substitution | relative activity for allyl alcohol* | relative activity for D-galactose | $T_{50}$ (° C.) |
|---|---|---|---|---|---|---|
| B1 | 1.D4 | A1237G | N413D | | 2.4 | |
| B2 | 2.G4 | A1237G | N413D | | 4.0 | |
|    |      | T1650A | S550 | | | |
| B3 | 3.H7 | A1237G | N413D | | 8.6 | |
|    |      | T1650A | S550 | | | |
|    |      | T1481C | V494A | | | |
| B4 | 4.F12 | A1237G | N413D | | 15.2 | |
|    |       | T1650A | S550 | | | |
|    |       | T1481C | V494A | | | |
|    |       | T1830A | S610 | | | |

*Allyl alcohol is oxidized by wild-type GAO at ca. 3% the rate of galactose oxidation.

Mutations identified at residues A3, L312, T218, P136, S550 and S610 are synonymous and, without being bound by theory, the observed increase in activity is probably due to higher expression of GAO in E. coli. Given the low expression level of recombinant wild-type GAO (less than 3% of total intracellular protein as determined by SDS-PAGE), this is a much needed improvement.

The variants identified also exhibit increased activity toward a variety of GAO substrates. Mutant 1.06.20E7 is about 200-fold more active toward 3-pyridylcarbinol and mutant 4.F 12 is about 15-fold more active toward glycerol, xylitol, beta-D-lactose, and IPTG.

The sequences of representative mutants of the invention identified in TABLE 4 are shown in FIGS. 17–28.

As shown in the above Examples, the galactose oxidase gene can be expressed in E. coli in relatively high yield, with an increased activity toward at least one substrate. In certain embodiments the activity is greatly increased toward several substrates. In certain embodiments the mutants exhibit thermostability.

The inducible promoters Plac or Ptac were effective for expression of the galactose oxidase gene and are preferred. Much higher expression may be possible when other strong promoters are used. However, some strong promoters may be counterproductive. For example, E. coli did not grow well when T7 promoter, which is stronger than lac promoter, was used for expression of the galactose oxidase gene. Double promoters of two Plac—Plac or Plac-Ptac were selected to express the galactose oxidase gene. Double promoters express the gene stronger than single promoter as compared pGAO-025 and pGAO-011. Triple promoters expressed the gene as well as double promoters. Upper promoter of double promoters seemed to be less effective than lower promoter in the Examples. Therefore, double promoters of Plac—Plac or Plac—Ptac are preferred. Induction of gene by IPTG was necessary when lac promoter or tac promoter was used. Timing of induction and incubation time after that were optimized.

In these experiments the fused form of GAO (i.e. as a fusion protein with lacZ) was not found to provide advantages, and was not necessary to express the fungal gene.

Galactose oxidase generally had reduced activity or lost its activity when codons were alternated or when it was produced as fused enzyme with His-tag. Culture condition was also important for production of the enzyme.

Galactose oxidase was engineered by directed evolution to produce more active variants toward natural and additional substrates. Activity of the present mutants was as high as about 65 times that of wild-type GAO. Mutants of the invention also are more stable than wild-type, and in particular exhibit improved thermal stability.

BIBLIOGRAPHY

1. Cleland, J. L. Wang, D. I. C. Bio Technology 8, 1274 (1990).
2. Bernarderz-Clark, E. D., Georgiou, G. Inclusion Bodies and Recovery of Proteins from the Aggregated States. In Protein Refolding, Bernarderz-Clark, E. D., Georgiou, G., Eds, ACS Washington, D.C. p. 1–20 (1990)
3. Thatcher, D. R.; Hitchcock, A. Protein Folding in Biotechnology. In Mechanisms of Protein Folding, Pain, R. H., Ed., IRL Press: Oxford p. 229–261 (1994).
4. Parekh, R., Forrester, K.; Wittrup, D. Protein Expres. Purif. 6, 537 (1995).
5. Arnold, F. H. Accounts Chem. Res. 31, 125 (1998).
6. Mitraki, A., King, J. FEBS Lett. 307, 20 (1992).
7. Zhang, J. X.; Goldenberg, D. P. Biochemistry 32, 14075 (1993).
8. Wetzel, R.; Perry, L. P.; Veilleux, C. Bio./Technology 9, 731 (1991).
9. Knappik, A.; Pluckthun, A. Protein Eng. 8, 81 (1995).
10. Crameri, A.; Whiteborn, E. A.; Tate, E.; Stemmer, W. P. C. Nature Biotechnol. 14, 315 (1996).
11. Tams, J. W.; Welinder, K. G. FEBS Lett. 421, 234 (1998).
12. Ortlepp, S. A.; Pollard-Knight, D.; Chiswell, D. J. J. Biotechnol. 11, 353 (1989).
13. Smith, A. T. et al. J. Biol. Chem. 265, 13335–13343 (1990).
14. Egorov, A. M.; Gazaryan, I. G.; Savelyev, S. V.; Fechina, V. A.; Veryovkin, A. N.; Kim, B. B. Ann. N.Y. Acad. Sci. 646, 35 (1991).
15. Moore, J. C.; Arnold, F. H. Nature Biotechnol. 14, 458 (1996).
16. Fitzgerald, M. M.; Churchill, M. J.; McRee, D. E., Goodin, D. B. Biochemistry 33, 3807 (1994).
17. Goodin, D. B.; Davidson, M. G.; Roe, J. A.; Mauk, A. G.; Smith, M. Biochemistry 30, 4953 (1991)
18. De Sutter, K.; Hostens, K.; Vandekerckhove, J.; Fiers, W. GENE 141, 163 (1994).
19, Sambrook, J.; Fritsch E. F.; Maniatis, T. Molecular Cloning: A Laboratory Manual Cold Spring Harbor Laboratory New York (1989).
20. Caldwell, R. C.; Joyce, G. F. PCR Methods Applic. 2, 28 (1992).

21. Beckman, R. A.; Mildvan, A. S., Loeb, L. A. *Biochemistry* 24, 5810 (1994).
22. Shafikhani, S.; Siegel, R. A.; Ferrari, E.; Schellenberger, V. *Biotechiques* 23, 304 (1997).
23. Stemmer, W. P. C. *Proc. Natl. Acad. Sci.* USA 91, 10747–51 (1994).
24. Zhao, H. M.; Arnold, F. H. *Nucleic Acids Res* 25, 1307 (1997).
25. Carbon, J.; Clarke, L.; Ilgen, C.; Ratzkin, B. The Construction and Use of Hybrid Plasmid Gene Banks in *Escherichia coli*. In *Recombinant Molecules: Impact on Science and Society*; Beers, R. F. J., Bassett, E. G., Eds, Raven Press: New York, pp 355–378 (1977).
26. Shindler, J S.; Childs, R. E.; Bardsley, W. G. *Eur. J. Biochem.* 65, 325 (1976).
27. Lei, S. P.; Lin, H. C.; Wang, S. S.; Callaway, J.; Wilcox, G. *J. Bacteriol.* 169, 4379 (1987).
28. Better, M.; Chang, C. P.; Robinson, R. R.; Horwitz, A. H. *Science* 240, 1041 (1988).
29. Goshorn, S. C.; Svensson, H. R.; Kerr, D. E.; Somerville, J. E.; Senter, P. D.; Fell, H. P. *Cancer Res.* 53, 2123 (1993).
30. Rathore, D.; Nayak, S. K.: Batra, J. K. *FEBS Lett.* 392, 259 (1996).
31. Studier, F. W.; Rosenberg, A. H.; Dunn, J. J.; Dubendorff, J. W. *Meth. Enzymol.* 185, 60 (1990).
32. Ostermeier, M.; Desutter, K.; Georgiou, G. Eukaryotic *J. Biol. Chem.* 271, 10616 (1996).
33. Savenkova, M. I.; Kuo, J. M.; Ortiz de Montellano, P. R. *Biochemistry* 37, 10828 (1998).
34. Gajhede, M.; Schuller, D. J.; Henriksen, A.; Smith, A. T.; Poulos, T. L. *Nature Struct. Biol.* 4, 1032 (1997).
35. Anfinsen, C. B. *Science* 181, 223 (1973).
36. Schein, C. H. *Bio Technology*, 8, 308 (1990).
37. Martineau, P. Jones, P.; Winter, G. *J. Mol. Biol.* 20, 117 (1998).
38. Stemmer, W. P. C. et al., *Biotechniques* 14, 256 (1992).
3). Arkin, A. and Youvan, D. C. *Proc. Natl. Acad. Sci. USA* 89, 7811 (1992).
40. Oliphant, A. R. et al., *Gene* 44, 177 (1986).
41. Hermes, J. D. et al., *Proc. Natl. Acad. Sci. USA* 87, 696 (1990).
42. Delagrave et al. *Protein Engineering* 6, 327 (1993).
43. Delagrave et al. *Bio Technology* 11, 1548 (1993)
44. Goldman, E. R. and Youvan D. C. *Bio Technology* 10,1557 (1992).
45. Leung, D. W. et al., *Technique* 1, (1989).
46. Gramm, H. et al., *Proc. Natl. Acad. Sci. USA* 89, 3576 (1992).
47. Castelli, M. C. et al., *Gene* 142, 113 (1994).
48. Gietz, D., Schiestl, R. H., Willems, A., Woods, R. A., *Yeast* 11, 355 (1995).
49. Welinder, K. G., *Eur J Biochem* 96, 483–502 (1979).
50. Sirotkin, K. J. *Theor. Biol.* 123, 261 (1986).
51. Glover, D. M. (ed.), 1985, DNA Cloning: A Practical Approach, MRL Press, Ltd., Oxford, U.K. Vol. I, II.
52. Schatz, P. J. Et al., *Annu. Rev. Genet.* 24, 215–248 (1990).
53. Gussow, D. & Clackson, T. (1989) *Nucleic Acids Res.*, 17, 4000–4000.
54. Gillam, E. M., Guo, Z., Martin, M. V., Jenkins, C. M. & Guengerich, F. P. (1995) Arch. Biochem. Biophys., 319, 540–550.
55. Guengerich, F. P., Martin, M. V., Guo, Z. & Chun, Y. J. (1996) *Meth. Enzymol.,* 272, 35–44.
56. Joo, H., Lin, Z. & Arnold, F. H. (1999) *Nature,* 399, 670–673.
57. Joo, H. Arisawa, A., Lin, Z. & Arnold, F. H. (1999) *Chem. Biol.,* 6, 669–706.
58. Khosla, C., Curtis, J E, Demodena, J., Rinas, U. & Bailey, J E (1990) *Bio Technology,* 8, 849–853
59. Bradford, M. (1978) Anal. Biochem., 72, 248–254
60. Dunford, H. B. (1991) *Peroxidases in Chemistry and Biology*, Vol 2. pp. 1–24
61. Miele, R. G., Prorok, M., Costa V. A. & Casteino F. J. (1999) J. Biol. Chem., 274, 7769–7776
62. Gazaryan, I. G. (1994) *LABPV Newsletters,* 4, 8–15
63. Rodriguez-Lopez, J. N., Smith, A. T., and Thorneley, R. N. F. (1995) *J. Biol. Chem.,* 271, 4023–4030
64. Haschke, R. H. & Friedhoff,. J. M. (1978) *Biochim. Biophys. Res. Commun.,* 90, 1039–1042
65. Smith, A. T., & Veitch, N. C. (1998) *Curr. Opin. Chem. Biol.* 2, 269–278
66. Chen, K. & Arnold, F. H. (1993) *Proc. Natl. Acad. USA,* 90, 5618–5622
67. Giver, L., Gershenson, A., Freskgard, P-O. & Arnold, F. H. (1998) *Proc. Natl. Acad. Sci. USA,* 95, 12809–12813
68. Yano, T., Oue, S. & Kagamliyama, H. (1998) *Proc. Natl. Acad. Sci. USA,* 95, 5511–5515
69. Cherry, J. R., Lamsa, M. H., Schneider, P., Vind, J., Svendson, A., Jones, A., & Pederson, A. H. (1999) *Nat. Biotechnol.,* 17, 379–384
70. Romanos, M. A., Scorer, C. A. & Clare J. J. (1992) *Yeast,* 8, 423–488
71. Fiedler, K. & Simons, K. (1995) *Cell,* 81, 309–312
72. Nagayama, Y., Namba, H., Yokoyama, N., Yamashita, S. & Niwa, M. (1998) *J. Biol. Chem.,* 273, 33423–33428
73. Helenius, A. (1994) *Mol. Biol Cell,* 5, 253–265
74. Miyazaki, K., Wintrode, P. L., Grayling, R. A., Rubingh, D. N. & Arnold, F. H. (2000) *J. Mol. Biol.* in press.
75. Zhao, H. M. & Arnold, F. H. (1999) *Protein Eng.* 12, 47–53
76. Borman, C. D., Saysell, C. G., and Sykes, A. G. (1997) *J. Biol. Inorg. Chem.* 2, 480–487.
77. Mendonca, M. H., and Zancan, G. T (1987) *Arch. Biochem. Biophys.* 272, 507–514.
78. Ito, N., Phillips, S. E. V., Yadav, K. D. S., and Knowles, P. F. (1994) *J. Mol. Biol* 238, 794–814.
79. Whitaker, M. W., and Whitaker, J. W. (1988) *J. Biol. Chem.* 263, 6074–6080.
80. Avigad, G., Amaral D., Asensio, C., and Horecker, B. L. (1962) *J. Biol. Chem.* 237, 2736–2743.
81. Amaral, D., Kelly-Falcoz, F., and Horecker, B. L. (1966) *Methods Enzymol.* 9, 87–2.
82. Klibanov, A. M., Alberti, B. N., and Marietta, M. A. (1982) *Biochem. Biophys. Res. Commun.* 108, 804–808.
83. Maradufu, A., Cree, G. M., and Perlin, A. S. (1971) *Canad. J. Chem.* 49, 3429–3436.
84. Wachter, R. M., and Branchaud, B. L. (1996) *J. Am. Chem. Soc.* 118, 2782–2789.
85. Baron, A. J., Stevens, C., Wilmot, C., Seneviratne, K. D., Blakeley, V., Dooley, D. M., Phillips, S. E. V., Knowles, P. F., and McPherson, M. J. (1994) *J. Biol. Chem.* 269, 25095–25105.
86. Ito, N., Phillips, S. E. V., Stevens, C., Ogel, Z. B., McPherson, M. J., Keen, J. N., Yadav, K. D. S., and Knowles, P. F. (1991) *Nature* 350, 87–90.
87. Ito, N., Knowles, P. F., and Phillips, S. E. V. (1995) *Methods Enzymol.* 258, 235–262.
88. Reynolds, M. P., Baron, A. J., Wilmot, C. M., Vinecombe, E., Stevens, C., Phillips, S.

E. V., Knowles, P. F., and McPherson, M. J. (1997) *J. Biol. Inorg. Chem.* 2, 327–335.
89. Tkac, J., Gemeiner, P., and Sturdik, E. (1999) *Biotechnology Techniques* 13, 931–936.
90. Vega, F. A., Nunez, C. G., Weigel, B., Hitzmann, B., and Ricci, J. C. D. (1998) *Anal. Chim. Acta* 373, 57–62.
91. Adanyi, N., Szabo, E. E., and Varadi, M. (1999) *European Food Research and Technology* 209, 220–226.
92. Mannino, S., Cosio, M. S., and Buratti. S. (1999) *Italian Journal of Food Science* 11, 57–65.
93. Szabo, E E., Adanyi, N., and Varadi, M. (1996) *Biosensors &Bioelectronics* 11, 1051–1058.
94. Vrbova, E., Peckova, J., and Marek, M. (1992) Collection of Czechoslovak Chemical Communications 57, 2287–2294.
95. Root, R. L., Durrwachter, J. R., and Wong, C. H., (1985) *J. Am. Chem. Soc.* 107, 2997–2999.
96. Dahlhoff, W. V., Idelmann, P., and Koster, R., (1980) *Angew. Chem. Int. Ed. Engl.* 19, 546–547.
97. Koster, R., Idelmann, P., and Dahlhoff, W. V. (1982) *Synthesis*, 650–652.
98. Liu, X. C., and Dordick, J. S. (1999) *J. Am. Chem. Soc.* 121, 466–467.
99. Mazur, A. W., and Hiler, G. D. (1997) *J. Org. Chem.* 62, 4471–4475.
100. Arts, S. J. H. F., Mombarg, E. J. M., vanbekkum, H., and Sheldon, R. A. (1997) *Synthesis-Stuttgart* 6, 597–610.
101. Yang, G. Y., and Shamsuddin, A. M. (1996) *Histol. Histopathol.* 11, 801–806.
102. Said, 1. T., Shamsuddin, A. M., Sherief, M. A., Taleb, S. G., Aref, W. F., and Kumar, D.(1999) *Histol. Histopathol.* 14, 351–357.
103. Marrs, B. L. in *IBC's Fifth Annual World Congress on Enzyme Technologies* (2000) Las Vegas, Nev.
104. Martin, I. G., Macias, E. M., Sanchez, J. S., and Rivera, B. G. (1998) *Food Chemistry* 61, 281–286.
105. Calderhead, D. M., and Lienhard, G. E. (1988) *J. Biol. Chem.* 263, 12171–12174.
106. Gahmberg, C. G., and Tolvanen, M. (1994) *Methods Enzymol.* 230, 32–44.
107. Mazur, A. in *Enzymes in Carbohydrate Synthesis* (1991) Bednarski, M. D. and Simon, E. S. Eds, pp. 99–110.
108. Tressel, P. (1980) Ph.D. Thesis, State University of New York, Buffalo.
109. Aisaka, K., and Terada, O (1981) Production of galactose oxidase by *Gibberella fujikuroi.*, Agric. Biol. Chem., 45(10), 2311–2316.
110. McPherson, M. J., Ogel, Z. B., Stevens, C., Yadav, K. D. S., Keen, J. N., and Knowles, P. F. (1992) Galactose oxidase of Dactylium dendroides., J. Biol. Chem., 267 (12), 8146–8152.
111. McPherson, M. J., Stevens, C., Baron, A. J., Ogel, Z. B., Sneviratne, K., Wilmot, C., Ito, N., Brocklebank, I., Phillips, S. E. V., and Knowles, P. F. (1993) Galactose oxidase: Molecular analysis and mutagenesis studies., Biochem. Soc. Transact., 21, 752–756.
112. Saysell, C. G., Barna, T., Borman, C. D., Baron, A. J., McPherson, M. J., and Sykes, A. G. (1997) Properties of the Trp290His variant of *Fusarium* NRRL 2903 galactose oxidase: Interaction of GOasesemi state with different buffer, its redox activity and ability to bind azide., JBIC, 2, 702–709.
113. Whittaker, M. M., Ballou, D. P., and Whittaker, J. W. (1998) Kinetic isotope effects as probes of the mechanism of galactose oxidase., Biochemistry, 37, 8426–8436.
114. Maradufu, A., et al. (1974) A non-hydrogen-binding role for the 4-hydroxyl group of D-galactose in its reaction with D-galactose oxidase., Carbohydr. Res. 32, 93–99.
115. Schlegel, R. A., Gerbeck, C. M., and Montgomery, R. (1968) Substrate specificity of D-galactose oxidase., Carbohydr. Res., 7, 193–199.
116. Hamilton, G. A., de Jersey, J., and Adolf, P. K. (1973) Galactose oxidase: The complexities of a simple enzyme., in King, T. E., et al. Eds., Oxidases and related redox enzyme, University Park Press, Baltimore, Md., 103–124.
117. Hamilton, F. A., Adolf, P. K., de Jersey, J., DuBois, G. C., Dyrkacz, G. R., and Libby, D. (1978.) Trivalent copper, superoxide, and galactose oxidase., J. Am. Chem. Soc., 100(6), 1899–1912.
118. Arts, S. J. H. F., Monbarg, E. J. M., van Bekkum, H., and Sheldon, R. A. (1997) Hydrogen peroxide and oxygen in catalytic oxidation of carbohydrates and related compounds., Synthesis, June, 1997, 597–613.
119. Kosman, D. J. (1984) Galactose oxidase., in Lontie, R., Eds., Copper proteins and copper enzymes. Vol. 2., CRC Press, Boca Raton, Fla., 1–26.
120. Mendonca, M. H., and Zancan, G. T. (1988) Role of carbohydrate content on the properties of galactose oxidase from Dactylium dendroides., Arch. Biochem. Biophys., 266(2), 427–434.
121. Koroeva, O. V., Rabinovich, M. L., Buglova, T. T., and Yaropolov, A. I. (1983) Some properties of galactose oxidase from *Fusarium graminearum.*, Prikl. Biokhim. Mikrobiol., 19(5), 632–637.
122. Avigad, G. (1985) Oxidation rates of some desialylated glycoproteins by galactose oxidase., Arch. Biochem. Biophys., 239(2), 531–537.
123. Tressel, P. S., and Kosman, D. J. (1989) Galactose oxidase from Dactylium dendroides., Methods Enzymol., 89, 163–171.
124. Tressel, P., and Kosman, D. J. (1980) A simple purification procedure for galactose oxidase., Anal. Biochem., 105, 150–153.
125. Avigad, G. (1978) An NADH coupled assay system for galactose oxidase., Anal. Biochem., 86. 470–476.
126. Kiba, N., Shitara, K., and Furusawa, M. (1989) A post-column co-immobilized galactose oxidase/peroxidase reactor for fluorometric detection of saccharides in a liquid chromatographic system., J. Chromatogr., 463, 183–187.
127. Lis, M., and Kuramitsu, H. K. (1997) Galactose oxidase-glucan binding domain fusion proteins as targeting inhibitors of dental plaque bacteria., Antimicrob. Agents Chemother., 41(5), 999–1003.
128. Martin, B. D., Linhardt, R. J., and Dordick, J. S. (1998) Highly swelling hydrogels from ordered galactose-based polyacrylates., Biomaterials, 19(1–3), 69–76.
129. Arnold, F. H. (1993) Engineering proteins for nonnatural environments., FEBS J., 7, 744–749.
130. Moore, J. C., and Arnold, F. H. (1996) Directed evolution of a para-nitrobenzyl esterase for aqueous-organic solvents., Nature Biotechnol., 14, 458–467.
131. You, L., and Arnold, F. H. (1996) Directed evolution of subtilisin E in *Bacillus* subtilisin to enhance total activity in aqueous dimethylformamide., Protein Eng., 9, 77–83.
132. Moore, J. C., Jin, H. M., Kuchner, O., and Arnold, F. H. (1997) Strategies for the in vitro evolution of protein function: Enzyme evolution by random recombination of improved sequences., J. Mol. Biol., 272, 336–347.

133. Arnold, F. H., and Moore, J. C. (1997) Optimization industrial enzymes by directed evolution., Adv Biochem. Eng. Biotechnol., 58, 1–14.
134. Zhao H., and Arnold, F. H. (1997) Optimization of DNA shuffling for high fidelity recombination., Nucleic acids Res., 25(6), 1307–1308.
135. Zhao, H., and Arnold, F. H. (1997) Functional and nonfunctional mutation distinguished by random recombination of homologous gene., PNAS. USA, 94, 7997–800.
136. Giver, L., Gershenson, A., Freskgard, P. O., and Arnold, F. H. (1998) Directed evolution of a thermostable esterase., Proc. Natl. Acad. Sci. USA, 95, 1209–12813.
137. Giver, L., and Arnold, F. H. (1998) Combinatorial protein design by in vitro recombination., Curr. Opinion Chem. Biol., 2, 335–338.
138. Arnold, F. H. (1998) Design by directed evolution., Accounts Chem. Res., 31, 125–131.
139 Zhao, H. M., Giver, L., Shao, Z. X., Affholter, J. A., and Arnold, F. H. (1998) Molecular evolution by staggered extension process (StEP) in vitro recombination., Nature Biotechnol., 16, 258–261.
140 Shao, Z. X., Zhao, H. M., Giver, L., and Arnold, F. H. (1998) Random-priming in vitro recombination, Nucleic Acids Res., 26, 681–683.
141 Kuchner, O., and Arnold, F. H. (1997) Directed evolution of enzyme catalysts., Trends Biotechnol., 15, 523–530.
142 Stemmer, W. P. C. (1994) Rapid evolution of a protein in vitro by DNA shuffling., Nature, 370, 389–391.
143 Stemmer, W. P. C. (1994) Methods for in vitro recombination., U.S. Pat. No. 5,605,793.
144 Crameri, A., Whitehorn, E. A., Tate, E., and Stemmer, W. P. C. (1996) Improved green fluorescent protein by molecular evolution using DNA shuffling., Nature Biotechnol., 14, 315–318.
145 Zhang, J. H., Dawes, G., and Stemmer, W. P. C. (1997) Directed evolution of fucosidase from a galactosidase by DNA shuffling and screening., Proc. Natl. Acad. Sci. USA, 94, 4504–4509.
146 Crameri, A., Dawes, G., Rodriguez, E. Jr., Silver, S., and Stemmer, W. P. C. (1997) Molecular evolution of an arsenate detoxification pathway by DNA shuffling., Nature Biotechnol., 15, 436–438.
147. Dower, W. J., Miller, J. F., and Ragsdale, C. W. (1988) High Efficiency transformation of *E. coli* by high voltage electroporation., Nucleic Acids Res., 16(13), 6127–6145.
148. Calvin, N. M., and Hanawalt, P. C. (1988) High-efficiency transformation of bacteria cells by electroporation, J. Bacteriol., 170(6), 2796–2801.
149. U.S. Pat. No. 5,741,691
150. U.S. Pat. No. 5,811,238
151. U.S. Pat. No. 5,830,721
152. International Application WO 98/42832
153. International Application WO 95/22625
154. International Application WO 97/20078
156. International Application WO 95/41653
157. Nakagawa, S., Ishino, S., and Teshiba, S. (1996) Construction of catalase deficient *Escherichia coli* strains for production of uricase. *Biosci. Biotech, Biochem.*, 60(3), 415–420.

What is claimed is:

1. An isolated polypeptide selected from the group consisting of:
   a) a polypeptide comprising the amino acid sequence of SEQ ID NO:10, 11, 12, 13, 14, 15, 16, 17, 18, 19, 20 or 21; and
   b) a polypeptide consisting of the amino acid sequence of SEQ ID NO: 10, 11, 12, 13, 14, 15, 16, 17, 18, 19, 20 or 21; wherein said polypeptide has galactose oxidase activity.

2. An isolated polypeptide selected from the group consisting of:
   a) a polypeptide encoded by a nucleic acid molecule comprising the nucleotide sequence of SEQ ID NO:37, 38, 39, 40, 41, 42, 43, 44, 45, 46, 47 or 48; and
   b) a polypeptide encoded by a nucleic acid molecule consisting of the nucleotide sequence of SEQ ID NO:37, 38, 39, 40, 41, 42, 43, 44, 45, 46, 47 or 48; wherein said polypeptide has galactose oxidase activity.

* * * * *

SEQUENCE LISTING

<160> NUMBER OF SEQ ID NOS: 48

<210> SEQ ID NO 1
<211> LENGTH: 36
<212> TYPE: DNA
<213> ORGANISM: Artificial Sequence
<220> FEATURE:
<223> OTHER INFORMATION: Primer

<400> SEQUENCE: 1
aattcgaagc ttatggcctc agcacctatc ggaagc           36

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
cttccttcta gattactgag taacgcgaat cgt              33

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3

-continued ggaagagaat tcaatacgca aaccgcctct    30

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
ggtcataagc ttttcctgtg tgaaattgtt at    32

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
accatgattt cgacgtcggt accctcagca    30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cttcctaagc tttcactgag taacgcgaat    30

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ggaagaggta ccaatacgca aaccgcctct    30

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
ttgttcctgc ggctgcagca attgaaccg    29

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
tgccggtcga ctctagatta ctgagtaacg    30

<210> SEQ ID NO 10
<211> LENGTH: 639
<212> TYPE: PRT
<213> ORGANISM: Artificial Sequence
<220> FEATURE:
<223> OTHER INFORMATION: Mutant 9.16.8D2 (N537D) of D. dendroides GaO

<400> SEQUENCE: 10

```
Ala Ser Ala Pro Ile Gly Ser Ala Ile Ser Arg Asn Asn Trp Ala Val
  1               5                  10                  15

Thr Cys Asp Ser Ala Gln Ser Gly Asn Glu Cys Asn Lys Ala Ile Asp
             20                  25                  30

Gly Asn Lys Asp Thr Phe Trp His Thr Phe Tyr Gly Ala Asn Gly Asp
         35                  40                  45

Pro Lys Pro Pro His Thr Tyr Thr Ile Asp Met Lys Thr Thr Gln Asn
 50                  55                  60

Val Asn Gly Leu Ser Met Leu Pro Arg Gln Asp Gly Asn Gln Asn Gly
 65                  70                  75                  80

Trp Ile Gly Arg His Glu Val Tyr Leu Ser Ser Asp Gly Thr Asn Trp
                 85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125

Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
        275                 280                 285

Ser Trp Ser Gly Gly Val Phe Glu Lys Asn Gly Glu Val Tyr Ser Pro
290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Cys Gly
370                 375                 380

Asn Ala Val Met Tyr Asp Ala Val Lys Gly Lys Ile Leu Thr Phe Gly
385                 390                 395                 400
```

-continued

```
Gly Ser Pro Asp Tyr Gln Asp Ser Asp Ala Thr Thr Asn Ala His Ile
            405                 410                 415
Ile Thr Leu Gly Glu Pro Gly Thr Ser Pro Asn Thr Val Phe Ala Ser
        420                 425                 430
Asn Gly Leu Tyr Phe Ala Arg Thr Phe His Thr Ser Val Val Leu Pro
        435                 440                 445
Asp Gly Ser Thr Phe Ile Thr Gly Gly Gln Arg Arg Gly Ile Pro Phe
    450                 455                 460
Glu Asp Ser Thr Pro Val Phe Thr Pro Glu Ile Tyr Val Pro Glu Gln
465                 470                 475                 480
Asp Thr Phe Tyr Lys Gln Asn Pro Asn Ser Ile Val Arg Val Tyr His
            485                 490                 495
Ser Ile Ser Leu Leu Pro Asp Gly Arg Val Phe Asn Gly Gly
        500                 505                 510
Gly Leu Cys Gly Asp Cys Thr Thr Asn His Phe Asp Ala Gln Ile Phe
    515                 520                 525
Thr Pro Asn Tyr Leu Tyr Asn Ser Asp Gly Asn Leu Ala Thr Arg Pro
    530                 535                 540
Lys Ile Thr Arg Thr Ser Thr Gln Ser Val Lys Val Gly Gly Arg Ile
545                 550                 555                 560
Thr Ile Ser Thr Asp Ser Ser Ile Ser Lys Ala Ser Leu Ile Arg Tyr
                565                 570                 575
Gly Thr Ala Thr His Thr Val Asn Thr Asp Gln Arg Arg Ile Pro Leu
            580                 585                 590
Thr Leu Thr Asn Asn Gly Gly Asn Ser Tyr Ser Phe Gln Val Pro Ser
        595                 600                 605
Asp Ser Gly Val Ala Leu Pro Gly Tyr Trp Met Leu Phe Val Met Asn
    610                 615                 620
Ser Ala Gly Val Pro Ser Val Ala Ser Thr Ile Arg Val Thr Gln
625                 630                 635

<210> SEQ ID NO 11
<211> LENGTH: 639
<212> TYPE: PRT
<213> ORGANISM: Artificial Sequence
<220> FEATURE:
<223> OTHER INFORMATION: Mutant 9.16.6C11 (V494A, C515S) of D.
      dendroides GaO

<400> SEQUENCE: 11

Ala Ser Ala Pro Ile Gly Ser Ala Ile Ser Arg Asn Asn Trp Ala Val
1               5                   10                  15
Thr Cys Asp Ser Ala Gln Ser Gly Asn Glu Cys Asn Lys Ala Ile Asp
            20                  25                  30
Gly Asn Lys Asp Thr Phe Trp His Thr Phe Tyr Gly Ala Asn Gly Asp
        35                  40                  45
Pro Lys Pro Pro His Thr Tyr Thr Ile Asp Met Lys Thr Thr Gln Asn
    50                  55                  60
Val Asn Gly Leu Ser Met Leu Pro Arg Gln Asp Gly Asn Gln Asn Gly
65              70                  75                  80
Trp Ile Gly Arg His Glu Val Tyr Leu Ser Ser Asp Gly Thr Asn Trp
                85                  90                  95
Gly Ser Pro Val Ala Ser Gly Ser Trp Phe Ala Asp Ser Thr Thr Lys
            100                 105                 110
Tyr Ser Asn Phe Glu Thr Arg Pro Ala Arg Tyr Val Arg Leu Val Ala
```

-continued

```
            115                 120                 125
Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ile
                165                 170                 175

Glu Pro Thr Ser Gly Arg Val Leu Met Trp Ser Ser Tyr Arg Asn Asp
                180                 185                 190

Ala Phe Gly Gly Ser Pro Gly Gly Ile Thr Leu Thr Ser Ser Trp Asp
                195                 200                 205

Pro Ser Thr Gly Ile Val Ser Asp Arg Thr Val Thr Thr Lys His
210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
                260                 265                 270

Gln Ser Ser Ala Thr Met Ser Asp Gly Arg Val Phe Thr Ile Gly Gly
                275                 280                 285

Ser Trp Ser Gly Gly Val Phe Glu Lys Asn Gly Glu Val Tyr Ser Pro
                290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
                340                 345                 350

Ala Met Asn Trp Tyr Tyr Thr Ser Gly Ser Gly Asp Val Lys Ser Ala
                355                 360                 365

Gly Lys Arg Gln Ser Asn Arg Gly Val Ala Pro Asp Ala Met Cys Gly
370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415

Ile Thr Leu Gly Glu Pro Gly Thr Ser Pro Asn Thr Val Phe Ala Ser
                420                 425                 430

Asn Gly Leu Tyr Phe Ala Arg Thr Phe His Thr Ser Val Val Leu Pro
                435                 440                 445

Asp Gly Ser Thr Phe Ile Thr Gly Gly Gln Arg Gly Ile Pro Phe
450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly
                500                 505                 510

Gly Leu Ser Gly Asp Cys Thr Thr Asn His Phe Asp Ala Gln Ile Phe
                515                 520                 525

Thr Pro Asn Tyr Leu Tyr Asn Ser Asn Gly Asn Leu Ala Thr Arg Pro
530                 535                 540
```

-continued

```
Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635

<210> SEQ ID NO 12
<211> LENGTH: 639
<212> TYPE: PRT
<213> ORGANISM: Artificial Sequence
<220> FEATURE:
<223> OTHER INFORMATION: Mutant 9.16.16D12 (P136, V494A) of D.
      dendroides GaO

<400> SEQUENCE: 12

Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
                20                  25                  30

Gly Asn Lys Asp Thr Phe Trp His Thr Phe Tyr Gly Ala Asn Gly Asp
            35                  40                  45

Pro Lys Pro Pro His Thr Tyr Thr Ile Asp Met Lys Thr Thr Gln Asn
        50                  55                  60

Val Asn Gly Leu Ser Met Leu Pro Arg Gln Asp Gly Asn Gln Asn Gly
65              70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125

Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
    210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
```

```
                      260                 265                 270
        Gln Ser Ser Ala Thr Met Ser Asp Gly Arg Val Phe Thr Ile Gly Gly
                    275                 280                 285

Ser Trp Ser Gly Gly Val Phe Glu Lys Asn Gly Glu Val Tyr Ser Pro
                    290                 295                 300

Ser Ser Lys Thr Trp Thr Ser Leu Pro Asn Ala Lys Val Asn Pro Met
        305                 310                 315                 320

Leu Thr Ala Asp Lys Gln Gly Leu Tyr Arg Ser Asp Asn His Ala Trp
                        325                 330                 335

Leu Phe Gly Trp Lys Lys Gly Ser Val Phe Gln Ala Gly Pro Ser Thr
                        340                 345                 350

Ala Met Asn Trp Tyr Tyr Thr Ser Gly Ser Gly Asp Val Lys Ser Ala
                        355                 360                 365

Gly Lys Arg Gln Ser Asn Arg Gly Val Ala Pro Asp Ala Met Cys Gly
                        370                 375                 380

Asn Ala Val Met Tyr Asp Ala Val Lys Gly Lys Ile Leu Thr Phe Gly
        385                 390                 395                 400

Gly Ser Pro Asp Tyr Gln Asp Ser Asp Ala Thr Thr Asn Ala His Ile
                        405                 410                 415

Ile Thr Leu Gly Glu Pro Gly Thr Ser Pro Asn Thr Val Phe Ala Ser
                        420                 425                 430

Asn Gly Leu Tyr Phe Ala Arg Thr Phe His Thr Ser Val Val Leu Pro
                        435                 440                 445

Asp Gly Ser Thr Phe Ile Thr Gly Gly Gln Arg Arg Gly Ile Pro Phe
                        450                 455                 460

Glu Asp Ser Thr Pro Val Phe Thr Pro Glu Ile Tyr Val Pro Glu Gln
        465                 470                 475                 480

Asp Thr Phe Tyr Lys Gln Asn Pro Asn Ser Ile Val Arg Ala Tyr His
                        485                 490                 495

Ser Ile Ser Leu Leu Leu Pro Asp Gly Arg Val Phe Asn Gly Gly Gly
                        500                 505                 510

Gly Leu Cys Gly Asp Cys Thr Thr Asn His Phe Asp Ala Gln Ile Phe
                        515                 520                 525

Thr Pro Asn Tyr Leu Tyr Asn Ser Asn Gly Asn Leu Ala Thr Arg Pro
                        530                 535                 540

Lys Ile Thr Arg Thr Thr Gln Ser Val Lys Val Gly Gly Arg Ile
        545                 550                 555                 560

Thr Ile Ser Thr Asp Ser Ser Ile Ser Lys Ala Ser Leu Ile Arg Tyr
                        565                 570                 575

Gly Thr Ala Thr His Thr Val Asn Thr Asp Gln Arg Arg Ile Pro Leu
                        580                 585                 590

Thr Leu Thr Asn Asn Gly Gly Asn Ser Tyr Ser Phe Gln Val Pro Ser
                        595                 600                 605

Asp Ser Gly Val Ala Leu Pro Gly Tyr Trp Met Leu Phe Val Met Asn
                        610                 615                 620

Ser Ala Gly Val Pro Ser Val Ala Ser Thr Ile Arg Val Thr Gln
        625                 630                 635

<210> SEQ ID NO 13
<211> LENGTH: 639
<212> TYPE: PRT
<213> ORGANISM: Artificial Sequence
<220> FEATURE:
<223> OTHER INFORMATION: Mutant 11.03.6D3 (S10P, P136, V494A) of D.
      dendroides GaO
```

<400> SEQUENCE: 13

```
Ala Ser Ala Pro Ile Gly Ser Ala Ile Pro Arg Asn Asn Trp Ala Val
  1               5                  10                  15

Thr Cys Asp Ser Ala Gln Ser Gly Asn Glu Cys Asn Lys Ala Ile Asp
             20                  25                  30

Gly Asn Lys Asp Thr Phe Trp His Thr Phe Tyr Gly Ala Asn Gly Asp
             35                  40                  45

Pro Lys Pro Pro His Thr Tyr Thr Ile Asp Met Lys Thr Thr Gln Asn
         50                  55                  60

Val Asn Gly Leu Ser Met Leu Pro Arg Gln Asp Gly Asn Gln Asn Gly
 65                  70                  75                  80

Trp Ile Gly Arg His Glu Val Tyr Leu Ser Ser Asp Gly Thr Asn Trp
                 85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
            115                 120                 125

Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
            195                 200                 205

Pro Ser Thr Gly Ile Val Ser Asp Arg Thr Val Thr Val Thr Lys His
        210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
            275                 280                 285

Ser Trp Ser Gly Gly Val Phe Glu Lys Asn Gly Glu Val Tyr Ser Pro
        290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
            355                 360                 365

Gly Lys Arg Gln Ser Asn Arg Gly Val Ala Pro Asp Ala Met Cys Gly
        370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
```

-continued

```
                    405                 410                 415
Ile Thr Leu Gly Glu Pro Gly Thr Ser Pro Asn Thr Val Phe Ala Ser
                420                 425                 430

Asn Gly Leu Tyr Phe Ala Arg Thr Phe His Thr Ser Val Val Leu Pro
            435                 440                 445

Asp Gly Ser Thr Phe Ile Thr Gly Gly Gln Arg Arg Gly Ile Pro Phe
        450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asn Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635
```

<210> SEQ ID NO 14
<211> LENGTH: 639
<212> TYPE: PRT
<213> ORGANISM: Artificial Sequence
<220> FEATURE:
<223> OTHER INFORMATION: Mutant 11.03.10C3 (A3, P136, G195E, V494A) of
      D. dendroides GaO

<400> SEQUENCE: 14

```
Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
        35                  40                  45

Pro Lys Pro Pro His Thr Tyr Thr Ile Asp Met Lys Thr Thr Gln Asn
    50                  55                  60

Val Asn Gly Leu Ser Met Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125
```

-continued

```
Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
                180                 185                 190

Ala Phe Glu Gly Ser Pro Gly Gly Ile Thr Leu Thr Ser Ser Trp Asp
                195                 200                 205

Pro Ser Thr Gly Ile Val Ser Asp Arg Thr Val Thr Val Thr Lys His
                210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
                260                 265                 270

Gln Ser Ser Ala Thr Met Ser Asp Gly Arg Val Phe Thr Ile Gly Gly
                275                 280                 285

Ser Trp Ser Gly Gly Val Phe Glu Lys Asn Gly Glu Val Tyr Ser Pro
290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
                340                 345                 350

Ala Met Asn Trp Tyr Tyr Thr Ser Gly Ser Gly Asp Val Lys Ser Ala
                355                 360                 365

Gly Lys Arg Gln Ser Asn Arg Gly Val Ala Pro Asp Ala Met Cys Gly
370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415

Ile Thr Leu Gly Glu Pro Gly Thr Ser Pro Asn Thr Val Phe Ala Ser
                420                 425                 430

Asn Gly Leu Tyr Phe Ala Arg Thr Phe His Thr Ser Val Val Leu Pro
                435                 440                 445

Asp Gly Ser Thr Phe Ile Thr Gly Gly Gln Arg Arg Gly Ile Pro Phe
                450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Pro Asp Gly Arg Val Phe Asn Gly Gly Gly
                500                 505                 510

Gly Leu Cys Gly Asp Cys Thr Thr Asn His Phe Asp Ala Gln Ile Phe
                515                 520                 525

Thr Pro Asn Tyr Leu Tyr Asn Ser Gly Asn Leu Ala Thr Arg Pro
530                 535                 540

Lys Ile Thr Arg Thr Ser Thr Gln Ser Val Lys Val Gly Gly Arg Ile
```

-continued

```
             545                 550                 555                 560
Thr Ile Ser Thr Asp Ser Ser Ile Ser Lys Ala Ser Leu Ile Arg Tyr
            565                 570                 575
Gly Thr Ala Thr His Thr Val Asn Thr Asp Gln Arg Arg Ile Pro Leu
            580                 585                 590
Thr Leu Thr Asn Asn Gly Gly Asn Ser Tyr Ser Phe Gln Val Pro Ser
            595                 600                 605
Asp Ser Gly Val Ala Leu Pro Gly Tyr Trp Met Leu Phe Val Met Asn
            610                 615                 620
Ser Ala Gly Val Pro Ser Val Ala Ser Thr Ile Arg Val Thr Gln
625                 630                 635

<210> SEQ ID NO 15
<211> LENGTH: 639
<212> TYPE: PRT
<213> ORGANISM: Artificial Sequence
<220> FEATURE:
<223> OTHER INFORMATION: Mutant 11.03.10D6 (P136, T218, L312, V494A,
      N535D) of D. dendroides GaO

<400> SEQUENCE: 15

Ala Ser Ala Pro Ile Gly Ser Ala Ile Ser Arg Asn Asn Trp Ala Val
1               5                   10                  15
Thr Cys Asp Ser Ala Gln Ser Gly Asn Glu Cys Asn Lys Ala Ile Asp
            20                  25                  30
Gly Asn Lys Asp Thr Phe Trp His Thr Phe Tyr Gly Ala Asn Gly Asp
        35                  40                  45
Pro Lys Pro Pro His Thr Tyr Thr Ile Asp Met Lys Thr Thr Gln Asn
    50                  55                  60
Val Asn Gly Leu Ser Met Leu Pro Arg Gln Asp Gly Asn Gln Asn Gly
65                  70                  75                  80
Trp Ile Gly Arg His Glu Val Tyr Leu Ser Ser Asp Gly Thr Asn Trp
                85                  90                  95
Gly Ser Pro Val Ala Ser Gly Ser Trp Phe Ala Asp Ser Thr Thr Lys
            100                 105                 110
Tyr Ser Asn Phe Glu Thr Arg Pro Ala Arg Tyr Val Arg Leu Val Ala
            115                 120                 125
Ile Thr Glu Ala Asn Gly Gln Pro Trp Thr Ser Ile Ala Glu Ile Asn
        130                 135                 140
Val Phe Gln Ala Ser Ser Tyr Thr Ala Pro Gln Pro Gly Leu Gly Arg
145                 150                 155                 160
Trp Gly Pro Thr Ile Asp Leu Pro Ile Val Pro Ala Ala Ala Ile
                165                 170                 175
Glu Pro Thr Ser Gly Arg Val Leu Met Trp Ser Ser Tyr Arg Asn Asp
            180                 185                 190
Ala Phe Gly Gly Ser Pro Gly Gly Ile Thr Leu Thr Ser Ser Trp Asp
        195                 200                 205
Pro Ser Thr Gly Ile Val Ser Asp Arg Thr Val Thr Val Thr Lys His
    210                 215                 220
Asp Met Phe Cys Pro Gly Ile Ser Met Asp Gly Asn Gly Gln Ile Val
225                 230                 235                 240
Val Thr Gly Gly Asn Asp Ala Lys Lys Thr Ser Leu Tyr Asp Ser Ser
                245                 250                 255
Ser Asp Ser Trp Ile Pro Gly Pro Asp Met Gln Val Ala Arg Gly Tyr
            260                 265                 270
```

```
Gln Ser Ser Ala Thr Met Ser Asp Gly Arg Val Phe Thr Ile Gly Gly
            275                 280                 285

Ser Trp Ser Gly Gly Val Phe Glu Lys Asn Gly Glu Val Tyr Ser Pro
        290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Cys Gly
370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
        435                 440                 445

Asp Gly Ser Thr Phe Ile Thr Gly Gly Gln Arg Arg Gly Ile Pro Phe
450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asp Ser Asn Gly Asn Leu Ala Thr Arg Pro
530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
610                 615                 620

Ser Ala Gly Val Pro Ser Val Ala Ser Thr Ile Arg Val Thr Gln
625                 630                 635

<210> SEQ ID NO 16
<211> LENGTH: 639
<212> TYPE: PRT
<213> ORGANISM: Artificial Sequence
<220> FEATURE:
<223> OTHER INFORMATION: Mutant 11.03.13E12 (M70V, P136, V494A) from D.
      Dendroides GaO

<400> SEQUENCE: 16
```

-continued

```
Ala Ser Ala Pro Ile Gly Ser Ala Ile Ser Arg Asn Asn Trp Ala Val
 1               5                  10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
        35                  40                  45

Pro Lys Pro Pro His Thr Tyr Thr Ile Asp Met Lys Thr Thr Gln Asn
    50                  55                  60

Val Asn Gly Leu Ser Val Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
                100                 105                 110

Tyr Ser Asn Phe Glu Thr Arg Pro Ala Arg Tyr Val Arg Leu Val Ala
            115                 120                 125

Ile Thr Glu Ala Asn Gly Gln Pro Trp Thr Ser Ile Ala Glu Ile Asn
130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
        195                 200                 205

Pro Ser Thr Gly Ile Val Ser Asp Arg Thr Val Thr Val Thr Lys His
    210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
        275                 280                 285

Ser Trp Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Cys Gly
    370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415
```

```
Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
            435                 440                 445

Asp Gly Ser Thr Phe Ile Thr Gly Gly Gln Arg Arg Gly Ile Pro Phe
            450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Pro Asp Gly Arg Val Phe Asn Gly Gly
            500                 505                 510

Gly Leu Cys Gly Asp Cys Thr Thr Asn His Phe Asp Ala Gln Ile Phe
            515                 520                 525

Thr Pro Asn Tyr Leu Tyr Asn Ser Asn Gly Asn Leu Ala Thr Arg Pro
            530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
            595                 600                 605

Asp Ser Gly Val Ala Leu Pro Gly Tyr Trp Met Leu Phe Val Met Asn
            610                 615                 620

Ser Ala Gly Val Pro Ser Val Ala Ser Thr Ile Arg Val Thr Gln
625                 630                 635

<210> SEQ ID NO 17
<211> LENGTH: 639
<212> TYPE: PRT
<213> ORGANISM: Artificial Sequence
<220> FEATURE:
<223> OTHER INFORMATION: Mutant 1.06.20E7 (S10P, M70V, P136, G195E,
      V494A, N535D) from D. Dendroides GaO

<400> SEQUENCE: 17

Ala Ser Ala Pro Ile Gly Ser Ala Ile Pro Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
        35                  40                  45

Pro Lys Pro Pro His Thr Tyr Thr Ile Asp Met Lys Thr Thr Gln Asn
50                  55                  60

Val Asn Gly Leu Ser Val Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125

Ile Thr Glu Ala Asn Gly Gln Pro Trp Thr Ser Ile Ala Glu Ile Asn
    130                 135                 140
```

```
Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ile
                165                 170                 175

Glu Pro Thr Ser Gly Arg Val Leu Met Trp Ser Ser Tyr Arg Asn Asp
                180                 185                 190

Ala Phe Glu Gly Ser Pro Gly Gly Ile Thr Leu Thr Ser Ser Trp Asp
                195                 200                 205

Pro Ser Thr Gly Ile Val Ser Asp Arg Thr Val Thr Thr Lys His
210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
                260                 265                 270

Gln Ser Ser Ala Thr Met Ser Asp Gly Arg Val Phe Thr Ile Gly Gly
                275                 280                 285

Ser Trp Ser Gly Gly Val Phe Glu Lys Asn Gly Glu Val Tyr Ser Pro
290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
                340                 345                 350

Ala Met Asn Trp Tyr Tyr Thr Ser Gly Ser Gly Asp Val Lys Ser Ala
                355                 360                 365

Gly Lys Arg Gln Ser Asn Arg Gly Val Ala Pro Asp Ala Met Cys Gly
370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asn Ala His Ile
                405                 410                 415

Ile Thr Leu Gly Glu Pro Gly Thr Ser Pro Asn Thr Val Phe Ala Ser
                420                 425                 430

Asn Gly Leu Tyr Phe Ala Arg Thr Phe His Thr Ser Val Val Leu Pro
                435                 440                 445

Asp Gly Ser Thr Phe Ile Thr Gly Gly Gln Arg Arg Gly Ile Pro Phe
450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
                485                 490                 495

Ser Ile Ser Leu Leu Leu Pro Asp Gly Arg Val Phe Asn Gly Gly Gly
                500                 505                 510

Gly Leu Cys Gly Asp Cys Thr Thr Asn His Phe Asp Ala Gln Ile Phe
                515                 520                 525

Thr Pro Asn Tyr Leu Tyr Asp Ser Asn Gly Asn Leu Ala Thr Arg Pro
                530                 535                 540

Lys Ile Thr Arg Thr Ser Thr Gln Ser Val Lys Val Gly Gly Arg Ile
545                 550                 555                 560
```

```
Thr Ile Ser Thr Asp Ser Ser Ile Ser Lys Ala Ser Leu Ile Arg Tyr
            565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
            595                 600                 605

Asp Ser Gly Val Ala Leu Pro Gly Tyr Trp Met Leu Phe Val Met Asn
            610                 615                 620

Ser Ala Gly Val Pro Ser Val Ala Ser Thr Ile Arg Val Thr Gln
625                 630                 635

<210> SEQ ID NO 18
<211> LENGTH: 639
<212> TYPE: PRT
<213> ORGANISM: Artificial Sequence
<220> FEATURE:
<223> OTHER INFORMATION: Mutant 1.D4 (N413D) from D. Dendroides GaO

<400> SEQUENCE: 18

Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
            35                  40                  45

Pro Lys Pro Pro His Thr Tyr Thr Ile Asp Met Lys Thr Thr Gln Asn
        50                  55                  60

Val Asn Gly Leu Ser Met Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
            115                 120                 125

Ile Thr Glu Ala Asn Gly Gln Pro Trp Thr Ser Ile Ala Glu Ile Asn
        130                 135                 140

Val Phe Gln Ala Ser Ser Tyr Thr Ala Pro Gln Pro Gly Leu Gly Arg
145                 150                 155                 160

Trp Gly Pro Thr Ile Asp Leu Pro Ile Val Pro Ala Ala Ala Ala Ile
                165                 170                 175

Glu Pro Thr Ser Gly Arg Val Leu Met Trp Ser Ser Tyr Arg Asn Asp
            180                 185                 190

Ala Phe Gly Gly Ser Pro Gly Gly Ile Thr Leu Thr Ser Ser Trp Asp
            195                 200                 205

Pro Ser Thr Gly Ile Val Ser Asp Arg Thr Val Thr Val Thr Lys His
        210                 215                 220

Asp Met Phe Cys Pro Gly Ile Ser Met Asp Gly Asn Gly Gln Ile Val
225                 230                 235                 240

Val Thr Gly Gly Asn Asp Ala Lys Lys Thr Ser Leu Tyr Asp Ser Ser
                245                 250                 255

Ser Asp Ser Trp Ile Pro Gly Pro Asp Met Gln Val Ala Arg Gly Tyr
            260                 265                 270

Gln Ser Ser Ala Thr Met Ser Asp Gly Arg Val Phe Thr Ile Gly Gly
            275                 280                 285
```

```
Ser Trp Ser Gly Gly Val Phe Glu Lys Asn Gly Glu Val Tyr Ser Pro
    290                 295                 300

Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
                325                 330                 335

Leu Phe Gly Trp Lys Lys Gly Ser Val Phe Gln Ala Gly Pro Ser Thr
                340                 345                 350

Ala Met Asn Trp Tyr Tyr Thr Ser Gly Ser Gly Asp Val Lys Ser Ala
                355                 360                 365

Gly Lys Arg Gln Ser Asn Arg Gly Val Ala Pro Asp Ala Met Cys Gly
    370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asp Ala His Ile
                405                 410                 415

Ile Thr Leu Gly Glu Pro Gly Thr Ser Pro Asn Thr Val Phe Ala Ser
                420                 425                 430

Asn Gly Leu Tyr Phe Ala Arg Thr Phe His Thr Ser Val Val Leu Pro
                435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Val Tyr His
                485                 490                 495

Ser Ile Ser Leu Leu Leu Pro Asp Gly Arg Val Phe Asn Gly Gly Gly
                500                 505                 510

Gly Leu Cys Gly Asp Cys Thr Thr Asn His Phe Asp Ala Gln Ile Phe
                515                 520                 525

Thr Pro Asn Tyr Leu Tyr Asn Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
                565                 570                 575

Gly Thr Ala Thr His Thr Val Asn Thr Asp Gln Arg Arg Ile Pro Leu
                580                 585                 590

Thr Leu Thr Asn Asn Gly Gly Asn Ser Tyr Ser Phe Gln Val Pro Ser
    595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635

<210> SEQ ID NO 19
<211> LENGTH: 639
<212> TYPE: PRT
<213> ORGANISM: Artificial Sequence
<220> FEATURE:
<223> OTHER INFORMATION: Mutant 2.G4 (N413D, S550) from D. Dendroides
      GaO

<400> SEQUENCE: 19

Ala Ser Ala Pro Ile Gly Ser Ala Ile Ser Arg Asn Asn Trp Ala Val
1               5                   10                  15
```

-continued

```
Thr Cys Asp Ser Ala Gln Ser Gly Asn Glu Cys Asn Lys Ala Ile Asp
             20                  25                  30
Gly Asn Lys Asp Thr Phe Trp His Thr Phe Tyr Gly Ala Asn Gly Asp
             35                  40                  45
Pro Lys Pro Pro His Thr Tyr Thr Ile Asp Met Lys Thr Thr Gln Asn
 50                  55                  60
Val Asn Gly Leu Ser Met Leu Pro Arg Gln Asp Gly Asn Gln Asn Gly
 65                  70                  75                  80
Trp Ile Gly Arg His Glu Val Tyr Leu Ser Ser Asp Gly Thr Asn Trp
                 85                  90                  95
Gly Ser Pro Val Ala Ser Gly Ser Trp Phe Ala Asp Ser Thr Thr Lys
            100                 105                 110
Tyr Ser Asn Phe Glu Thr Arg Pro Ala Arg Tyr Val Arg Leu Val Ala
            115                 120                 125
Ile Thr Glu Ala Asn Gly Gln Pro Trp Thr Ser Ile Ala Glu Ile Asn
130                 135                 140
Val Phe Gln Ala Ser Ser Tyr Thr Ala Pro Gln Pro Gly Leu Gly Arg
145                 150                 155                 160
Trp Gly Pro Thr Ile Asp Leu Pro Ile Val Pro Ala Ala Ala Ile
                165                 170                 175
Glu Pro Thr Ser Gly Arg Val Leu Met Trp Ser Ser Tyr Arg Asn Asp
            180                 185                 190
Ala Phe Gly Gly Ser Pro Gly Gly Ile Thr Leu Thr Ser Ser Trp Asp
            195                 200                 205
Pro Ser Thr Gly Ile Val Ser Asp Arg Thr Val Thr Val Thr Lys His
            210                 215                 220
Asp Met Phe Cys Pro Gly Ile Ser Met Asp Gly Asn Gly Gln Ile Val
225                 230                 235                 240
Val Thr Gly Gly Asn Asp Ala Lys Lys Thr Ser Leu Tyr Asp Ser Ser
                245                 250                 255
Ser Asp Ser Trp Ile Pro Gly Pro Asp Met Gln Val Ala Arg Gly Tyr
            260                 265                 270
Gln Ser Ser Ala Thr Met Ser Asp Gly Arg Val Phe Thr Ile Gly Gly
            275                 280                 285
Ser Trp Ser Gly Gly Val Phe Glu Lys Asn Gly Glu Val Tyr Ser Pro
290                 295                 300
Ser Ser Lys Thr Trp Thr Ser Leu Pro Asn Ala Lys Val Asn Pro Met
305                 310                 315                 320
Leu Thr Ala Asp Lys Gln Gly Leu Tyr Arg Ser Asp Asn His Ala Trp
            325                 330                 335
Leu Phe Gly Trp Lys Lys Gly Ser Val Phe Gln Ala Gly Pro Ser Thr
            340                 345                 350
Ala Met Asn Trp Tyr Tyr Thr Ser Gly Ser Gly Asp Val Lys Ser Ala
            355                 360                 365
Gly Lys Arg Gln Ser Asn Arg Gly Val Ala Pro Asp Ala Met Cys Gly
370                 375                 380
Asn Ala Val Met Tyr Asp Ala Val Lys Gly Lys Ile Leu Thr Phe Gly
385                 390                 395                 400
Gly Ser Pro Asp Tyr Gln Asp Ser Asp Ala Thr Thr Asp Ala His Ile
                405                 410                 415
Ile Thr Leu Gly Glu Pro Gly Thr Ser Pro Asn Thr Val Phe Ala Ser
            420                 425                 430
```

```
Asn Gly Leu Tyr Phe Ala Arg Thr Phe His Thr Ser Val Val Leu Pro
            435                 440                 445

Asp Gly Ser Thr Phe Ile Thr Gly Gly Gln Arg Arg Gly Ile Pro Phe
        450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Val Tyr His
            485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asn Ser Asn Gly Asn Leu Ala Thr Arg Pro
        530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
            565                 570                 575

Gly Thr Ala Thr His Thr Val Asn Thr Asp Gln Arg Arg Ile Pro Leu
        580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
        610                 615                 620

Ser Ala Gly Val Pro Ser Val Ala Ser Thr Ile Arg Val Thr Gln
625                 630                 635

<210> SEQ ID NO 20
<211> LENGTH: 639
<212> TYPE: PRT
<213> ORGANISM: Artificial Sequence
<220> FEATURE:
<223> OTHER INFORMATION: Mutant 3.H7 (N413D, S550, V494A) from D.
      Dendroides GaO

<400> SEQUENCE: 20

Ala Ser Ala Pro Ile Gly Ser Ala Ile Ser Arg Asn Asn Trp Ala Val
1               5                   10                  15

Thr Cys Asp Ser Ala Gln Ser Gly Asn Glu Cys Asn Lys Ala Ile Asp
            20                  25                  30

Gly Asn Lys Asp Thr Phe Trp His Thr Phe Tyr Gly Ala Asn Gly Asp
        35                  40                  45

Pro Lys Pro Pro His Thr Tyr Thr Ile Asp Met Lys Thr Thr Gln Asn
    50                  55                  60

Val Asn Gly Leu Ser Met Leu Pro Arg Gln Asp Gly Asn Gln Asn Gly
65                  70                  75                  80

Trp Ile Gly Arg His Glu Val Tyr Leu Ser Ser Asp Gly Thr Asn Trp
                85                  90                  95

Gly Ser Pro Val Ala Ser Gly Ser Trp Phe Ala Asp Ser Thr Thr Lys
            100                 105                 110

Tyr Ser Asn Phe Glu Thr Arg Pro Ala Arg Tyr Val Arg Leu Val Ala
        115                 120                 125

Ile Thr Glu Ala Asn Gly Gln Pro Trp Thr Ser Ile Ala Glu Ile Asn
    130                 135                 140

Val Phe Gln Ala Ser Ser Tyr Thr Ala Pro Gln Pro Gly Leu Gly Arg
145                 150                 155                 160
```

```
Trp Gly Pro Thr Ile Asp Leu Pro Ile Val Pro Ala Ala Ala Ile
            165                 170                 175
Glu Pro Thr Ser Gly Arg Val Leu Met Trp Ser Ser Tyr Arg Asn Asp
            180                 185                 190
Ala Phe Gly Gly Ser Pro Gly Ile Thr Leu Thr Ser Ser Trp Asp
            195                 200                 205
Pro Ser Thr Gly Ile Val Ser Asp Arg Thr Val Thr Thr Lys His
            210                 215                 220
Asp Met Phe Cys Pro Gly Ile Ser Met Asp Gly Asn Gly Gln Ile Val
225                 230                 235                 240
Val Thr Gly Gly Asn Asp Ala Lys Lys Thr Ser Leu Tyr Asp Ser Ser
                245                 250                 255
Ser Asp Ser Trp Ile Pro Gly Pro Asp Met Gln Val Ala Arg Gly Tyr
                260                 265                 270
Gln Ser Ser Ala Thr Met Ser Asp Gly Arg Val Phe Thr Ile Gly Gly
            275                 280                 285
Ser Trp Ser Gly Gly Val Phe Glu Lys Asn Gly Glu Val Tyr Ser Pro
290                 295                 300
Ser Ser Lys Thr Trp Thr Ser Leu Pro Asn Ala Lys Val Asn Pro Met
305                 310                 315                 320
Leu Thr Ala Asp Lys Gln Gly Leu Tyr Arg Ser Asp Asn His Ala Trp
                325                 330                 335
Leu Phe Gly Trp Lys Lys Gly Ser Val Phe Gln Ala Gly Pro Ser Thr
                340                 345                 350
Ala Met Asn Trp Tyr Tyr Thr Ser Gly Ser Gly Asp Val Lys Ser Ala
                355                 360                 365
Gly Lys Arg Gln Ser Asn Arg Gly Val Ala Pro Asp Ala Met Cys Gly
                370                 375                 380
Asn Ala Val Met Tyr Asp Ala Val Lys Gly Lys Ile Leu Thr Phe Gly
385                 390                 395                 400
Gly Ser Pro Asp Tyr Gln Asp Ser Asp Ala Thr Thr Asp Ala His Ile
                405                 410                 415
Ile Thr Leu Gly Glu Pro Gly Thr Ser Pro Asn Thr Val Phe Ala Ser
                420                 425                 430
Asn Gly Leu Tyr Phe Ala Arg Thr Phe His Thr Ser Val Val Leu Pro
                435                 440                 445
Asp Gly Ser Thr Phe Ile Thr Gly Gly Gln Arg Arg Gly Ile Pro Phe
450                 455                 460
Glu Asp Ser Thr Pro Val Phe Thr Pro Glu Ile Tyr Val Pro Glu Gln
465                 470                 475                 480
Asp Thr Phe Tyr Lys Gln Asn Pro Asn Ser Ile Val Arg Ala Tyr His
                485                 490                 495
Ser Ile Ser Leu Leu Leu Pro Asp Gly Arg Val Phe Asn Gly Gly Gly
                500                 505                 510
Gly Leu Cys Gly Asp Cys Thr Thr Asn His Phe Asp Ala Gln Ile Phe
                515                 520                 525
Thr Pro Asn Tyr Leu Tyr Asn Ser Asn Gly Asn Leu Ala Thr Arg Pro
                530                 535                 540
Lys Ile Thr Arg Thr Ser Thr Gln Ser Val Lys Val Gly Gly Arg Ile
545                 550                 555                 560
Thr Ile Ser Thr Asp Ser Ser Ile Ser Lys Ala Ser Leu Ile Arg Tyr
                565                 570                 575
```

```
Gly Thr Ala Thr His Thr Val Asn Thr Asp Gln Arg Arg Ile Pro Leu
            580                 585                 590
Thr Leu Thr Asn Asn Gly Gly Asn Ser Tyr Ser Phe Gln Val Pro Ser
        595                 600                 605
Asp Ser Gly Val Ala Leu Pro Gly Tyr Trp Met Leu Phe Val Met Asn
    610                 615                 620
Ser Ala Gly Val Pro Ser Val Ala Ser Thr Ile Arg Val Thr Gln
625                 630                 635
```

<210> SEQ ID NO 21
<211> LENGTH: 639
<212> TYPE: PRT
<213> ORGANISM: Artificial Sequence
<220> FEATURE:
<223> OTHER INFORMATION: Mutant 4.F12 (N413D, S550, V494A, S610) from D. Dendroides GaO

<400> SEQUENCE: 21

```
Ala Ser Ala Pro Ile Gly Ser Ala Ile Ser Arg Asn Asn Trp Ala Val
1               5                   10                  15
Thr Cys Asp Ser Ala Gln Ser Gly Asn Glu Cys Asn Lys Ala Ile Asp
            20                  25                  30
Gly Asn Lys Asp Thr Phe Trp His Thr Phe Tyr Gly Ala Asn Gly Asp
        35                  40                  45
Pro Lys Pro Pro His Thr Tyr Thr Ile Asp Met Lys Thr Gln Asn
    50                  55                  60
Val Asn Gly Leu Ser Met Leu Pro Arg Gln Asp Gly Asn Gln Asn Gly
65                  70                  75                  80
Trp Ile Gly Arg His Glu Val Tyr Leu Ser Ser Asp Gly Thr Asn Trp
                85                  90                  95
Gly Ser Pro Val Ala Gly Ser Trp Phe Ala Asp Ser Thr Thr Lys
            100                 105                 110
Tyr Ser Asn Phe Glu Thr Arg Pro Ala Arg Tyr Val Arg Leu Val Ala
        115                 120                 125
Ile Thr Glu Ala Asn Gly Gln Pro Trp Thr Ser Ile Ala Glu Ile Asn
130                 135                 140
Val Phe Gln Ala Ser Ser Tyr Thr Ala Pro Gln Pro Gly Leu Gly Arg
145                 150                 155                 160
Trp Gly Pro Thr Ile Asp Leu Pro Ile Val Pro Ala Ala Ala Ile
                165                 170                 175
Glu Pro Thr Ser Gly Arg Val Leu Met Trp Ser Ser Tyr Arg Asn Asp
            180                 185                 190
Ala Phe Gly Gly Ser Pro Gly Gly Ile Thr Leu Thr Ser Ser Trp Asp
        195                 200                 205
Pro Ser Thr Gly Ile Val Ser Asp Arg Thr Val Thr Val Thr Lys His
    210                 215                 220
Asp Met Phe Cys Pro Gly Ile Ser Met Asp Gly Asn Gly Gln Ile Val
225                 230                 235                 240
Val Thr Gly Gly Asn Asp Ala Lys Lys Thr Ser Leu Tyr Asp Ser Ser
                245                 250                 255
Ser Asp Ser Trp Ile Pro Gly Pro Asp Met Gln Val Ala Arg Gly Tyr
            260                 265                 270
Gln Ser Ser Ala Thr Met Ser Asp Gly Arg Val Phe Thr Ile Gly Gly
        275                 280                 285
Ser Trp Ser Gly Gly Val Phe Glu Lys Asn Gly Glu Val Tyr Ser Pro
    290                 295                 300
```

```
Ser Ser Lys Thr Trp Thr Ser Leu Pro Asn Ala Lys Val Asn Pro Met
305                 310                 315                 320

Leu Thr Ala Asp Lys Gln Gly Leu Tyr Arg Ser Asp Asn His Ala Trp
            325                 330                 335

Leu Phe Gly Trp Lys Lys Gly Ser Val Phe Gln Ala Gly Pro Ser Thr
            340                 345                 350

Ala Met Asn Trp Tyr Tyr Thr Ser Gly Ser Gly Asp Val Lys Ser Ala
        355                 360                 365

Gly Lys Arg Gln Ser Asn Arg Gly Val Ala Pro Asp Ala Met Cys Gly
    370                 375                 380

Asn Ala Val Met Tyr Asp Ala Val Lys Gly Lys Ile Leu Thr Phe Gly
385                 390                 395                 400

Gly Ser Pro Asp Tyr Gln Asp Ser Asp Ala Thr Thr Asp Ala His Ile
            405                 410                 415

Ile Thr Leu Gly Glu Pro Gly Thr Ser Pro Asn Thr Val Phe Ala Ser
            420                 425                 430

Asn Gly Leu Tyr Phe Ala Arg Thr Phe His Thr Ser Val Val Leu Pro
        435                 440                 445

Asp Gly Ser Thr Phe Ile Thr Gly Gly Gln Arg Arg Gly Ile Pro Phe
    450                 455                 460

Glu Asp Ser Thr Pro Val Phe Thr Pro Glu Ile Tyr Val Pro Glu Gln
465                 470                 475                 480

Asp Thr Phe Tyr Lys Gln Asn Pro Asn Ser Ile Val Arg Ala Tyr His
            485                 490                 495

Ser Ile Ser Leu Leu Leu Pro Asp Gly Arg Val Phe Asn Gly Gly Gly
            500                 505                 510

Gly Leu Cys Gly Asp Cys Thr Thr Asn His Phe Asp Ala Gln Ile Phe
        515                 520                 525

Thr Pro Asn Tyr Leu Tyr Asn Ser Asn Gly Asn Leu Ala Thr Arg Pro
    530                 535                 540

Lys Ile Thr Arg Thr Ser Thr Gln Ser Val Lys Val Gly Gly Arg Ile
545                 550                 555                 560

Thr Ile Ser Thr Asp Ser Ser Ile Ser Lys Ala Ser Leu Ile Arg Tyr
            565                 570                 575

Gly Thr Ala Thr His Thr Val Asn Thr Asp Gln Arg Arg Ile Pro Leu
            580                 585                 590

Thr Leu Thr Asn Asn Gly Gly Asn Ser Tyr Ser Phe Gln Val Pro Ser
        595                 600                 605

Asp Ser Gly Val Ala Leu Pro Gly Tyr Trp Met Leu Phe Val Met Asn
    610                 615                 620

Ser Ala Gly Val Pro Ser Val Ala Ser Thr Ile Arg Val Thr Gln
625                 630                 635
```

<210> SEQ ID NO 22
<211> LENGTH: 10
<212> TYPE: DNA
<213> ORGANISM: Artificial Sequence
<220> FEATURE:
<223> OTHER INFORMATION: Vector sequence
<400> SEQUENCE: 22
aagctagctt                                                          10

<210> SEQ ID NO 23
<211> LENGTH: 10

-continued

```
<212> TYPE: DNA
<213> ORGANISM: Artificial Sequence
<220> FEATURE:
<223> OTHER INFORMATION: Vector sequence

<400> SEQUENCE: 23
ttcgatcgaa                                                              10

<210> SEQ ID NO 24
<211> LENGTH: 10
<212> TYPE: DNA
<213> ORGANISM: Artificial Sequence
<220> FEATURE:
<223> OTHER INFORMATION: Vector sequence

<400> SEQUENCE: 24
gaattaattc                                                              10

<210> SEQ ID NO 25
<211> LENGTH: 10
<212> TYPE: DNA
<213> ORGANISM: Artificial Sequence
<220> FEATURE:
<223> OTHER INFORMATION: Vector sequence

<400> SEQUENCE: 25
cttaattaag                                                              10

<210> SEQ ID NO 26
<211> LENGTH: 9
<212> TYPE: PRT
<213> ORGANISM: Dactylium dendroides

<400> SEQUENCE: 26

Met Ala Ser Ala Pro Ile Gly Ser Ala
 1               5

<210> SEQ ID NO 27
<211> LENGTH: 27
<212> TYPE: DNA
<213> ORGANISM: Dactylium dendroides

<400> SEQUENCE: 27
atggcctcag cacctatcgg aagcgcc                                           27

<210> SEQ ID NO 28
<211> LENGTH: 27
<212> TYPE: DNA
<213> ORGANISM: Artificial Sequence
<220> FEATURE:
<221> NAME/KEY: unsure
<222> LOCATION: (1)...(27)
<223> OTHER INFORMATION: "n" at positions 6, 9, 12, 15, and 21 is either
      a, t, g, or c. "n" at position 18 is either a, t, or c.
<220> FEATURE:
<223> OTHER INFORMATION: Randomly altered D. Dendoides wild-type
      sequence

<400> SEQUENCE: 28
atggcntcng cnccnatngg nagcgcc                                           27

<210> SEQ ID NO 29
<211> LENGTH: 14
<212> TYPE: DNA
<213> ORGANISM: Artificial Sequence
<220> FEATURE:
<223> OTHER INFORMATION: Vector sequence
```

```
<400> SEQUENCE: 29
aggaaaagct tatg                                                      14

<210> SEQ ID NO 30
<211> LENGTH: 15
<212> TYPE: DNA
<213> ORGANISM: Artificial Sequence
<220> FEATURE:
<223> OTHER INFORMATION: Vector sequence

<400> SEQUENCE: 30
aggaaaaagc ttatg                                                     15

<210> SEQ ID NO 31
<211> LENGTH: 16
<212> TYPE: DNA
<213> ORGANISM: Artificial Sequence
<220> FEATURE:
<223> OTHER INFORMATION: Vector sequence

<400> SEQUENCE: 31
aggaaacaag cttatg                                                    16

<210> SEQ ID NO 32
<211> LENGTH: 16
<212> TYPE: DNA
<213> ORGANISM: Artificial Sequence
<220> FEATURE:
<223> OTHER INFORMATION: Vector sequence

<400> SEQUENCE: 32
aggaacaaag cttatg                                                    16

<210> SEQ ID NO 33
<211> LENGTH: 14
<212> TYPE: DNA
<213> ORGANISM: Artificial Sequence
<220> FEATURE:
<223> OTHER INFORMATION: Vector sequence

<400> SEQUENCE: 33
aggaaaagct tatg                                                      14

<210> SEQ ID NO 34
<211> LENGTH: 15
<212> TYPE: DNA
<213> ORGANISM: Artificial Sequence
<220> FEATURE:
<223> OTHER INFORMATION: Vector sequence

<400> SEQUENCE: 34
aggaaaaagc ttatg                                                     15

<210> SEQ ID NO 35
<211> LENGTH: 16
<212> TYPE: DNA
<213> ORGANISM: Artificial Sequence
<220> FEATURE:
<223> OTHER INFORMATION: Vector sequence

<400> SEQUENCE: 35
aggaaacaag cttatg                                                    16

<210> SEQ ID NO 36
```

```
<211> LENGTH: 16
<212> TYPE: DNA
<213> ORGANISM: Artificial Sequence
<220> FEATURE:
<223> OTHER INFORMATION: Vector sequence

<400> SEQUENCE: 36
aggaacaaag cttatg                                                    16

<210> SEQ ID NO 37
<211> LENGTH: 1917
<212> TYPE: DNA
<213> ORGANISM: Artificial Sequence
<220> FEATURE:
<223> OTHER INFORMATION: Mutant 9.16.8D2 (A1609G) of D. Dendroides GaO

<400> SEQUENCE: 37
gcctcagcac ctatcggaag cgccatttct cgcaacaact gggccgtcac ttgcgacagt     60
gcacagtcgg gaaatgaatg caacaaggcc attgatggca acaaggatac cttttggcac    120
acattctatg cgccaacgg ggatccaaag cccctcaca catacacgat tgacatgaag      180
acaactcaga acgtcaacgg cttgtctatg ctgcctcgac aggatggtaa ccaaaacggc    240
tggatcggtc gccatgaggt ttatctaagc tcagatggca caaactgggg cagccctgtt    300
gcgtcaggta gttggttcgc cgactctact acaaaatact ccaactttga aactcgccct    360
gctcgctatg ttcgtcttgt cgctatcact gaagcgaatg ccagccttg gactagcatt     420 gcagagatca acgtcttcca agctagttct tacacagccc cccagcctgg tcttggacgc    480
tggggtccga ctattgactt accgattgtt cctgcggctg cagcaattga accgacatcg    540
ggacgagtcc ttatgtggtc ttcatatcgc aatgatgcat ttggaggatc ccctggtggt    600
atcactttga cgtcttcctg ggatccatcc actggtattg tttccgaccg cactgtgaca    660
gtcaccaagc atgatatgtt ctgccctggt atctccatgg atggtaacgg tcagatcgta    720
gtcacaggtg gcaacgatgc caagaagacc agtttgtatg attcatctag cgatagctgg    780
atcccgggac ctgacatgca agtggctcgt gggtatcagt catcagctac catgtcagac    840
ggtcgtgttt ttaccattgg aggctcctgg agcggtggcg tatttgagaa gaatggcgaa    900
gtctatagcc catcttcaaa gacatggacg tccctaccca atgccaaggt caacccaatg    960
ttgacggctg acaagcaagg attgtaccgt tcagacaacc acgcgtggct ctttggatgg   1020
aagaagggtt cggtgttcca gcgggacct agcacagcca tgaactggta ctataccagt    1080
ggaagtggtg atgtgaagtc agccggaaaa cgccagtcta accgtggtgt agcccctgat   1140
gccatgtgcg gaaacgctgt catgtacgac gccgttaaag gaaagatcct gacctttggc   1200
ggctccccag attatcaaga ctctgacgcc acaaccaacg cccacatcat caccctcggt   1260
gaacccggaa catctcccaa cactgtcttt gctagcaatg ggttgtactt tgcccgaacg   1320
tttcacacct ctgttgttct tccagacgga agcacgttta ttacaggagg ccaacgacgt   1380
ggaattccgt tcgaggattc aaccccggta tttacacctg agatctacgt ccctgaacaa   1440
gacactttct acaagcagaa ccccaactcc attgttcgcg tctaccatag catttcccctt   1500 ttgttacctg atggcagggt atttaacggt ggtggtggtc tttgtggcga ttgtaccacg   1560
aatcatttcg acgcgcaaat ctttacgcca aactatcttt acaatagcga cggcaatctc   1620
gcgacacgtc ccaagattac cagaacctct acacagagcg tcaaggtcgg tggcagaatt   1680
acaatctcga cggattcttc gattagcaag gcgtcgttga ttcgctatgg tacagcgaca   1740
cacacggtta atactgacca cgccgcatt cccctgactc tgacaaacaa tggaggaaat   1800
```

-continued

```
agctattctt tccaagttcc tagcgactct ggtgttgctt tgcctggcta ctggatgttg    1860
ttcgtgatga actcggccgg tgttcctagt gtggcttcga cgattcgcgt tactcag      1917
```

<210> SEQ ID NO 38
<211> LENGTH: 1917
<212> TYPE: DNA
<213> ORGANISM: Artificial Sequence
<220> FEATURE:
<223> OTHER INFORMATION: Mutant 9.16.6C11 (T1481C, T1543A) of D.
      Dendroides GaO

<400> SEQUENCE: 38

```
gcctcagcac ctatcggaag cgccatttct cgcaacaact gggccgtcac ttgcgacagt      60
gcacagtcgg gaaatgaatg caacaaggcc attgatggca acaaggatac cttttggcac     120
acattctatg cgccaacgg ggatccaaag cccctcaca catacacgat tgacatgaag       180
acaactcaga acgtcaacgg cttgtctatg ctgcctcgac aggatggtaa ccaaaacggc     240
tggatcggtc gccatgaggt ttatctaagc tcagatggca caaactgggg cagccctgtt     300
gcgtcaggta gttggttcgc cgactctact acaaaatact ccaactttga aactcgccct     360
gctcgctatg ttcgtcttgt cgctatcact gaagcgaatg ccagccttg gactagcatt     420
gcagagatca acgtcttcca agctagttct tacacagccc ccagcctgg tcttggacgc     480
tggggtccga ctattgactt accgattgtt cctgcggctg cagcaattga accgacatcg     540
ggacgagtcc ttatgtggtc ttcatatcgc aatgatgcat ttggaggatc ccctggtggt     600
atcactttga cgtcttcctg ggatccatcc actggtattg tttccgaccg cactgtgaca     660
gtcaccaagc atgatatgtt ctgccctggt atctccatgg atggtaacgg tcagatcgta     720
gtcacaggtg gcaacgatgc caagaagacc agtttgtatg attcatctag cgatagctgg     780
atcccgggac ctgacatgca gtggctcgt gggtatcagt catcagctac catgtcagac     840
ggtcgtgttt taccattgg aggctcctgg agcggtggcg tatttgagaa gaatggcgaa     900
gtctatagcc catcttcaaa gacatggacg tccctaccca atgccaaggt caacccaatg     960
ttgacggctg acaagcaagg attgtaccgt tcagacaacc acgcgtggct ctttggatgg    1020
aagaagggtt cggtgttcca agcgggacct agcacagcca tgaactgta ctataccagt    1080
ggaagtggtg atgtgaagtc agccggaaaa cgccagtcta ccgtggtgt agcccctgat    1140
gccatgtgcg gaaacgctgt catgtacgac gccgttaaag gaaagatcct gacctttggc    1200
ggctccccag attatcaaga ctctgacgcc acaaccaacg cccacatcat caccctcggt    1260
gaacccggaa catctcccaa cactgtcttt gctagcaatg ggttgtactt tgcccgaacg    1320
tttcacacct ctgttgttct tccagacgga agcacgttta ttacaggagg ccaacgacgt    1380
ggaattccgt tcgaggattc aaccccggta tttacacctg agatctacgt ccctgaacaa    1440
gacactttct acaagcagaa ccccaactcc attgttcgcg cctaccatag catttcccttt  1500
ttgttacctg atggcagggt atttaacggt ggtggtggtc ttagtggcga ttgtaccacg    1560
aatcatttcg acgcgcaaat ctttacgcca aactatcttt acaatagcaa cggcaatctc    1620
gcgacacgtc ccaagattac cagaacctct acacagagcg tcaaggtcgg tggcagaatt    1680
acaatctcga cggattcttc gattagcaag gcgtcgttga ttcgctatgg tacagcgaca    1740
cacacggtta atactgacca gcgccgcatt cccctgactc tgacaaacaa tggaggaaat    1800
agctattctt tccaagttcc tagcgactct ggtgttgctt tgcctggcta ctggatgttg    1860
ttcgtgatga actcggccgg tgttcctagt gtggcttcga cgattcgcgt tactcag      1917
```

<210> SEQ ID NO 39
<211> LENGTH: 1917
<212> TYPE: DNA
<213> ORGANISM: Artificial Sequence
<220> FEATURE:
<223> OTHER INFORMATION: Mutant 9.16.16D12 (T408C, T1481C) of D.
      Dendroides GaO

<400> SEQUENCE: 39

```
gcctcagcac ctatcggaag cgccatttct cgcaacaact gggccgtcac ttgcgacagt      60
gcacagtcgg gaaatgaatg caacaaggcc attgatggca acaaggatac cttttggcac     120
acattctatg gcgccaacgg ggatccaaag cccctcaca catacacgat tgacatgaag      180
acaactcaga acgtcaacgg cttgtctatg ctgcctcgac aggatggtaa ccaaaacggc     240
tggatcggtc gccatgaggt ttatctaagc tcagatggca caaactgggg cagccctgtt     300
gcgtcaggta gttggttcgc cgactctact acaaaatact ccaactttga aactcgccct     360
gctcgctatg ttcgtcttgt cgctatcact gaagcgaatg ccagccctg gactagcatt      420
gcagagatca acgtcttcca agctagttct tacacagccc ccagcctgg tcttggacgc      480
tggggtccga ctattgactt accgattgtt cctgcggctg cagcaattga accgacatcg     540
ggacgagtcc ttatgtggtc ttcatatcgc aatgatgcat tggaggatc ccctggtggt      600
atcactttga cgtcttcctg ggatccatcc actggtattg tttccgaccg cactgtgaca     660
gtcaccaagc atgatatgtt ctgccctggt atctccatgg atggtaacgg tcagatcgta     720
gtcacaggtg gcaacgatgc caagaagacc agtttgtatg attcatctag cgatagctgg     780
atcccgggac ctgacatgca agtggctcgt gggtatcagt catcagctac catgtcagac     840
ggtcgtgttt ttaccattgg aggctcctgg agcggtggcg tatttgagaa gaatggcgaa     900
gtctatagcc catcttcaaa gacatggacg tccctaccca atgccaaggt caacccaatg     960
ttgacggctg acaagcaagg attgtaccgt tcagacaacc acgcgtggct ctttggatgg    1020
aagaagggtt cggtgttcca gcgggacct agcacagcca tgaactggta ctataccagt     1080
ggaagtggtg atgtgaagtc agccggaaaa cgccagtcta accgtggtgt agcccctgat    1140
gccatgtgcg gaaacgctgt catgtacgac gccgttaaag gaaagatcct gacctttggc    1200
ggctccccag attatcaaga ctctgacgcc acaaccaacg cccacatcat caccctcggt    1260
gaacccggaa catctcccaa cactgtcttt gctagcaatg ggttgtactt tgcccgaacg    1320
tttcacacct ctgttgttct tccagacgga agcacgttta ttacaggagg ccaacgacgt    1380
ggaattccgt tcgaggattc aaccccggta tttacccctg agatctacgt ccctgaacaa    1440
gacactttct acaagcagaa ccccaactcc attgttcgcg cctaccatag catttccctt    1500
ttgttacctg atgcagggt atttaacggt ggtggtggtc tttgtggcga ttgtaccacg    1560
aatcatttcg acgcgcaaat ctttacgcca aactatcttt acaatagcaa cggcaatctc    1620
gcgacacgtc ccaagattac cagaacctct acacagagcg tcaaggtcgg tggcagaatt    1680
acaatctcga cggattcttc gattagcaag gcgtcgttga ttcgctatgg tacagcgaca    1740
cacacggtta atactgacca gcgccgcatt cccctgactc tgacaaacaa tggaggaaat    1800
agctattctt tccaagttcc tagcgactct ggtgttgctt tgcctggcta ctggatgttg    1860
ttcgtgatga actcggccgg tgttcctagt gtggcttcga cgattcgcgt tactcag      1917
```

<210> SEQ ID NO 40
<211> LENGTH: 1917

<212> TYPE: DNA
<213> ORGANISM: Artificial Sequence
<220> FEATURE:
<223> OTHER INFORMATION: Mutant 11.03.6D3 (T28C, T408C, T1481C) of D. Dendroides GaO

<400> SEQUENCE: 40

```
gcctcagcac ctatcggaag cgccattcct cgcaacaact gggccgtcac ttgcgacagt      60
gcacagtcgg gaaatgaatg caacaaggcc attgatggca acaaggatac cttttggcac     120
acattctatg cgccaacgg ggatccaaag ccccctcaca catacacgat tgacatgaag      180
acaactcaga acgtcaacgg cttgtctatg ctgcctcgac aggatggtaa ccaaaacggc     240
tggatcggtc gccatgaggt ttatctaagc tcagatggca caaactgggg cagccctgtt     300
gcgtcaggta gttggttcgc cgactctact acaaaatact ccaactttga aactcgccct     360
gctcgctatg ttcgtcttgt cgctatcact gaagcgaatg ccagccctg gactagcatt      420
gcagagatca acgtcttcca agctagttct tacacagccc cccagcctgg tcttggacgc     480
tggggtccga ctattgactt accgattgtt cctgcggctg cagcaattga accgacatcg     540
ggacgagtcc ttatgtggtc ttcatatcgc aatgatgcat ttggaggatc ccctggtggt     600
atcactttga cgtcttcctg ggatccatcc actggtattg tttccgaccg cactgtgaca     660
gtcaccaagc atgatatgtt ctgccctggt atctccatgg atggtaacgg tcagatcgta     720
gtcacaggtg gcaacgatgc caagaagacc agtttgtatg attcatctag cgatagctgg     780
atcccgggac ctgacatgca agtggctcgt gggtatcagt catcagctac catgtcagac     840
ggtcgtgttt ttaccattgg aggctcctgg agcggtggcg tatttgagaa gaatggcgaa     900
gtctatagcc catcttcaaa gacatggacg tccctaccca atgccaaggt caacccaatg     960
ttgacggctg acaagcaagg attgtaccgt tcagacaacc acgcgtggct ctttggatgg    1020
aagaagggtt cggtgttcca gcgggacct agcacagcca tgaactggta ctataccagt     1080
ggaagtggtg atgtgaagtc agccggaaaa cgccagtcta ccgtggtgt agcccctgat     1140
gccatgtgcg gaaacgctgt catgtacgac gccgttaaag gaaagatcct gacctttggc    1200
ggctccccag attatcaaga ctctgacgcc acaaccaacg cccacatcat caccctcggt    1260
gaacccggaa catctcccaa cactgtcttt gctagcaatg ggttgtactt tgcccgaacg    1320
tttcacacct ctgttgttct tccagacgga agcacgttta ttacaggagg ccaacgacgt    1380
ggaattccgt tcgaggattc aaccccggta tttacacctg agatctacgt ccctgaacaa    1440
gacactttct acaagcagaa ccccaactcc attgttcgcg cctaccatag catttccctt    1500
ttgttacctg atgcagggt atttaacggt ggtggtggtc tttgtggcga ttgtaccacg     1560
aatcatttcg acgcgcaaat ctttacgcca aactatcttt acaatagcaa cggcaatctc    1620
gcgacacgtc ccaagattac cagaaccctct acacagagcg tcaaggtcgg tggcagaatt    1680
acaatctcga cggattcttc gattagcaag gcgtcgttga ttcgctatgg tacagcgaca    1740
cacacggtta atactgacca gcgccgcatt cccctgactc tgacaaacaa tggaggaaat    1800
agctattctt tccaagttcc tagcgactct ggtgttgctt tgcctggcta ctggatgttg    1860
ttcgtgatga actcggccgg tgttcctagt gtggcttcga cgattcgcgt tactcag       1917
```

<210> SEQ ID NO 41
<211> LENGTH: 1917
<212> TYPE: DNA
<213> ORGANISM: Artificial Sequence
<220> FEATURE:
<223> OTHER INFORMATION: Mutant 11.03.10C3 (A9C, T408C, G584A, T1481C)

of D. Dendroides GaO

<400> SEQUENCE: 41

```
gcctcagccc ctatcggaag cgccatttct cgcaacaact gggccgtcac ttgcgacagt      60
gcacagtcgg gaaatgaatg caacaaggcc attgatggca acaaggatac cttttggcac     120
acattctatg gcgccaacgg ggatccaaag ccccctcaca catacacgat tgacatgaag     180
acaactcaga acgtcaacgg cttgtctatg ctgcctcgac aggatggtaa ccaaaacggc     240
tggatcggtc gccatgaggt ttatctaagc tcagatggca caaactgggg cagccctgtt     300
gcgtcaggta gttggttcgc cgactctact acaaaatact ccaactttga aactcgccct     360
gctcgctatg ttcgtcttgt cgctatcact gaagcgaatg ccagccctg gactagcatt      420
gcagagatca acgtcttcca agctagttct tacacagccc cccagcctgg tcttggacgc     480
tggggtccga ctattgactt accgattgtt cctgcggctg cagcaattga accgacatcg     540
ggacgagtcc ttatgtggtc ttcatatcgc aatgatgcat tgaaggatc ccctggtggt      600
atcactttga cgtcttcctg ggatccatcc actggtattg tttccgaccg cactgtgaca     660
gtcaccaagc atgatatgtt ctgccctggt atctccatgg atggtaacgg tcagatcgta     720
gtcacaggtg gcaacgatgc caagaagacc agtttgtatg attcatctag cgatagctgg     780
atcccgggac ctgacatgca agtggctcgt gggtatcagt catcagctac catgtcagac     840
ggtcgtgttt ttaccattgg aggctcctgg agcggtggcg tatttgagaa gaatggcgaa     900
gtctatagcc catcttcaaa gacatggacg tccctaccca tgccaaggt caacccaatg      960
ttgacggctg acaagcaagg attgtaccgt tcagacaacc acgcgtggct ctttggatgg    1020
aagaagggtt cggtgttcca agcgggacct agcacagcca tgaactggta ctataccagt    1080
ggaagtggtg atgtgaagtc agccggaaaa cgccagtcta accgtggtgt agcccctgat    1140
gccatgtgcg gaaacgctgt catgtacgac gccgttaaag gaaagatcct gacctttggc    1200
ggctccccag attatcaaga ctctgacgcc acaaccaacg cccacatcat caccctcggt    1260
gaacccggaa catctcccaa cactgtcttt gctagcaatg ggttgtactt tgcccgaacg    1320
tttcacacct ctgttgttct tccagacgga agcacgttta ttacaggagg ccaacgacgt    1380
ggaattccgt tcgaggattc aaccccggta tttacctg agatctacgt ccctgaacaa      1440
gacactttct acaagcagaa ccccaactcc attgttcgcg cctaccatag catttccctt    1500
ttgttacctg atgcagggt atttaacggt ggtggtggtc tttgtggcga ttgtaccacg     1560
aatcatttcg acgcgcaaat ctttacgcca aactatcttt acaatagcaa cggcaatctc    1620
gcgacacgtc ccaagattac cagaacctct acacagagcg tcaaggtcgg tggcagaatt    1680
acaatctcga cggattcttc gattagcaag gcgtcgttga ttcgctatgg tacagcgaca    1740
cacacggtta atactgacca gcgccgcatt cccctgactc tgacaaacaa tggaggaaat    1800
agctattctt tccaagttcc tagcgactct ggtgttgctt tgcctggcta ctggatgttg    1860
ttcgtgatga actcggccgg tgttcctagt gtggcttcga cgattcgcgt tactcag       1917
```

<210> SEQ ID NO 42
<211> LENGTH: 1917
<212> TYPE: DNA
<213> ORGANISM: Artificial Sequence
<220> FEATURE:
<223> OTHER INFORMATION: Mutant 11.03.10D6 (T408C, T654C, A936G, T1481C, A1603G) of D. Dendroides GaO

<400> SEQUENCE: 42

```
gcctcagcac ctatcggaag cgccatttct cgcaacaact gggccgtcac ttgcgacagt    60
gcacagtcgg gaaatgaatg caacaaggcc attgatggca acaaggatac cttttggcac   120
acattctatg gcgccaacgg ggatccaaag cccctcaca catacacgat tgacatgaag    180
acaactcaga acgtcaacgg cttgtctatg ctgcctcgac aggatggtaa ccaaaacggc   240
tggatcggtc gccatgaggt ttatctaagc tcagatggca caaactgggg cagccctgtt   300
gcgtcaggta gttggttcgc cgactctact acaaaatact ccaactttga aactcgccct   360
gctcgctatg ttcgtcttgt cgctatcact gaagcgaatg ccagccctg gactagcatt    420 gcagagatca acgtcttcca agctagttct tacacagccc ccagcctgg tcttggacgc    480 tggggtccga ctattgactt accgattgtt cctgcggctg cagcaattga accgacatcg   540
ggacgagtcc ttatgtggtc ttcatatcgc aatgatgcat tggaggatc ccctggtggt    600 atcactttga cgtcttcctg ggatccatcc actggtattg tttccgaccg caccgtgaca   660
gtcaccaagc atgatatgtt ctgccctggt atctccatgg atggtaacgg tcagatcgta   720
gtcacaggtg gcaacgatgc caagaagacc agtttgtatg attcatctag cgatagctgg   780
atcccgggac ctgacatgca agtggctcgt gggtatcagt catcagctac catgtcagac   840
ggtcgtgttt ttaccattgg aggctcctgg agcggtggcg tatttgagaa gaatggcgaa   900
gtctatagcc catcttcaaa gacatggacg tccctgccca atgccaaggt caacccaatg   960
ttgacggctg acaagcaagg attgtaccgt tcagacaacc acgcgtggct ctttggatgg  1020
aagaagggtt cggtgttcca agcgggacct agcacagcca tgaactggta ctataccagt  1080
ggaagtggtg atgtgaagtc agccggaaaa cgccagtcta accgtggtgt agcccctgat  1140
gccatgtgcg gaaacgctgt catgtacgac gccgttaaag gaaagatcct gacctttggc  1200
ggctccccag attatcaaga ctctgacgcc acaaccaacg cccacatcat caccctcggt  1260
gaacccggaa catctcccaa cactgtcttt gctagcaatg ggttgtactt tgcccgaacg  1320
tttcacacct ctgttgttct tccagacgga agcacgttta ttacaggagg ccaacgacgt  1380
ggaattccgt tcgaggattc aaccccggta tttacacctg agatctacgt ccctgaacaa  1440
gacactttct acaagcagaa ccccaactcc attgttcgcg cctaccatag catttcccct  1500
ttgttacctg atggcagggt atttaacggt ggtggtggtc tttgtggcga ttgtaccacg  1560
aatcatttcg acgcgcaaat ctttacgcca actatctttt acgatagcaa cggcaatctc  1620
gcgacacgtc ccaagattac cagaacctct cacagagcg tcaaggtcgg tgcagaatt   1680 acaatctcga cggattcttc gattagcaag gcgtcgttga ttcgctatgg tacagcgaca  1740
cacacggtta atactgacca gcgccgcatt ccctgactc tgacaaacaa tggaggaaat  1800
agctattctt ccaagttcc tagcgactct ggtgttgctt tgcctggcta ctggatgttg   1860
ttcgtgatga actcggccgg tgttcctagt gtggcttcga cgattcgcgt tactcag     1917
```

<210> SEQ ID NO 43
<211> LENGTH: 1917
<212> TYPE: DNA
<213> ORGANISM: Artificial Sequence
<220> FEATURE:
<223> OTHER INFORMATION: Mutant 11.03.13E12 (A208G, T408C, T1481C) of D. Dendroides GaO

<400> SEQUENCE: 43

```
gcctcagcac ctatcggaag cgccatttct cgcaacaact gggccgtcac ttgcgacagt    60
gcacagtcgg gaaatgaatg caacaaggcc attgatggca acaaggatac cttttggcac   120
```

-continued

```
acattctatg gcgccaacgg ggatccaaag cccccctcaca catacacgat tgacatgaag    180
acaactcaga acgtcaacgg cttgtctgtg ctgcctcgac aggatggtaa ccaaaacggc    240
tggatcggtc gccatgaggt ttatctaagc tcagatggca caaactgggg cagccctgtt    300
gcgtcaggta gttggttcgc cgactctact acaaaatact ccaactttga aactcgccct    360
gctcgctatg ttcgtcttgt cgctatcact gaagcgaatg ccagccctg actagcatt     420
gcagagatca acgtcttcca agctagttct tacacagccc cccagcctgg tcttggacgc    480
tggggtccga ctattgactt accgattgtt cctgcggctg cagcaattga accgacatcg    540
ggacgagtcc ttatgtggtc ttcatatcgc aatgatgcat ttggaggatc ccctggtggt    600
atcactttga cgtcttcctg ggatccatcc actggtattg tttccgaccg cactgtgaca    660
gtcaccaagc atgatatgtt ctgccctggt atctccatgg atggtaacgg tcagatcgta    720
gtcacaggtg gcaacgatgc caagaagacc agtttgtatg attcatctag cgatagctgg    780
atcccgggac ctgacatgca agtggctcgt gggtatcagt catcagctac catgtcagac    840
ggtcgtgttt taccattgg aggctcctgg agcggtggcg tatttgagaa gaatggcgaa     900
gtctatagcc catcttcaaa gacatggacg tccctaccca atgccaaggt caacccaatg    960
ttgacggctg acaagcaagg attgtaccgt tcagacaacc acgcgtggct ctttggatgg   1020
aagaagggtt cggtgttcca agcgggacct agcacagcca tgaactggta ctataccagt   1080
ggaagtggtg atgtgaagtc agccggaaaa cgccagtcta accgtggtgt agcccctgat   1140
gccatgtgcg gaaacgctgt catgtacgac gccgttaaag gaaagatcct gacctttggc   1200
ggctccccag attatcaaga ctctgacgcc acaaccaacg cccacatcat caccctcggt   1260
gaacccggaa catctcccaa cactgtctttt gctagcaatg ggttgtactt tgcccgaacg   1320
tttcacacct ctgttgttct tccagacgga agcacgttta ttacaggagg ccaacgacgt   1380
ggaattccgt tcgaggattc aaccccggta tttacacctg agatctacgt ccctgaacaa   1440
gacactttct acaagcagaa ccccaactcc attgttcgcg cctaccatag catttcccttt  1500
ttgttacctg atggcagggt atttaacggt ggtggtggtc tttgtggcga ttgtaccacg   1560
aatcatttcg acgcgcaaat ctttacgcca aactatcttt acaatagcaa cggcaatctc   1620
gcgacacgtc ccaagattac cagaacctct acacagagcg tcaaggtcgg tggcagaatt   1680
acaatctcga cggattcttc gattagcaag gcgtcgttga ttcgctatgg tacagcgaca   1740
cacacggtta atactgacca gcgccgcatt cccctgactc tgacaaacaa tggaggaaat   1800
agctattctt tccaagttcc tagcgactct ggtgttgctt tgcctggcta ctggatgttg   1860
ttcgtgatga actcggccgg tgttcctagt gtggcttcga cgattcgcgt tactcag      1917
```

<210> SEQ ID NO 44
<211> LENGTH: 1917
<212> TYPE: DNA
<213> ORGANISM: Artificial Sequence
<220> FEATURE:
<223> OTHER INFORMATION: Mutant 1.06.20E7 (T28C, A208G, T408C, G584A, T1481C, A1603G) of D. Dendroides GaO

<400> SEQUENCE: 44

```
gcctcagcac ctatcggaag cgccattcct cgcaacaact gggccgtcac ttgcgacagt     60
gcacagtcgg gaaatgaatg caacaaggcc attgatggca acaaggatac cttttggcac    120
acattctatg gcgccaacgg ggatccaaag cccccctcaca catacacgat tgacatgaag    180
acaactcaga acgtcaacgg cttgtctgtg ctgcctcgac aggatggtaa ccaaaacggc    240
```

```
tggatcggtc gccatgaggt ttatctaagc tcagatggca caaactgggg cagccctgtt      300
gcgtcaggta gttggttcgc cgactctact acaaaatact ccaactttga aactcgccct      360
gctcgctatg ttcgtcttgt cgctatcact gaagcgaatg ccagccctg gactagcatt       420 gcagagatca acgtcttcca agctagttct tacacagccc cccagcctgg tcttggacgc      480
tggggtccga ctattgactt accgattgtt cctgcggctg cagcaattga accgacatcg      540
ggacgagtcc ttatgtggtc ttcatatcgc aatgatgcat tgaaggatc ccctggtggt       600 atcactttga cgtcttcctg ggatccatcc actggtattg tttccgaccg cactgtgaca      660
gtcaccaagc atgatatgtt ctgccctggt atctccatgg atggtaacgg tcagatcgta      720
gtcacaggtg gcaacgatgc caagaagacc agtttgtatg attcatctag cgatagctgg      780
atcccgggac ctgacatgca agtggctcgt gggtatcagt catcagctac catgtcagac      840
ggtcgtgttt ttaccattgg aggctcctgg agcggtggcg tatttgagaa gaatggcgaa      900
gtctatagcc catcttcaaa gacatggacg tccctaccca atgccaaggt caacccaatg      960
ttgacggctg acaagcaagg attgtaccgt tcagacaacc acgcgtggct ctttggatgg     1020
aagaagggtt cggtgttcca agcgggacct agcacagcca tgaactggta ctataccagt     1080
ggaagtggtg atgtgaagtc agccggaaaa cgccagtcta accgtggtgt agccctgat     1140 gccatgtgcg gaaacgctgt catgtacgac gccgttaaag aaagatcct gacctttggc      1200 ggctccccag attatcaaga ctctgacgcc acaaccaacg cccacatcat caccctcggt     1260
gaacccggaa catctcccaa cactgtcttt gctagcaatg ggttgtactt tgcccgaacg     1320
tttcacacct ctgttgttct tccagacgga agcacgttta ttacaggagg ccaacgacgt     1380
ggaattccgt tcgaggattc aaccccggta tttacacctg agatctacgt ccctgaacaa     1440
gacactttct acaagcagaa ccccaactcc attgttcgcg cctaccatag catttccctt     1500
ttgttacctg atggcagggt atttaacggt ggtggtggtc tttgtggcga ttgtaccacg     1560
aatcatttcg acgcgcaaat ctttacgcca aactatcttt acgatagcaa cggcaatctc     1620
gcgacacgtc ccaagattac cagaacctct cacagagcg tcaaggtcgg tgcagaatt      1680 acaatctcga cggattcttc gattagcaag gcgtcgttga ttcgctatgg tacagcgaca     1740
cacacggtta atactgacca gcgccgcatt cccctgactc tgacaaacaa tggaggaaat     1800
agctattctt ccaagttcc tagcgactct ggtgttgctt tgcctggcta ctggatgttg      1860
ttcgtgatga actcggccgg tgttcctagt gtggcttcga cgattcgcgt tactcag       1917
```

<210> SEQ ID NO 45
<211> LENGTH: 1917
<212> TYPE: DNA
<213> ORGANISM: Artificial Sequence
<220> FEATURE:
<223> OTHER INFORMATION: Mutant 1.D4 (A1237G) of D. Dendroides GaO

<400> SEQUENCE: 45

```
gcctcagcac ctatcggaag cgccatttct cgcaacaact gggccgtcac ttgcgacagt       60
gcacagtcgg gaaatgaatg caacaaggcc attgatggca caaggatac cttttggcac       120 acattctatg gcgccaacgg ggatccaaag cccccctcaca catacacgat tgacatgaag      180
acaactcaga acgtcaacgg cttgtctatg ctgcctcgac aggatggtaa ccaaaacggc      240
tggatcggtc gccatgaggt ttatctaagc tcagatggca caaactgggg cagccctgtt      300
gcgtcaggta gttggttcgc cgactctact acaaaatact ccaactttga aactcgccct      360
gctcgctatg ttcgtcttgt cgctatcact gaagcgaatg ccagccttg gactagcatt       420
```

```
gcagagatca acgtcttcca agctagttct tacacagccc cccagcctgg tcttggacgc    480
tggggtccga ctattgactt accgattgtt cctgcggctg cagcaattga accgacatcg    540
ggacgagtcc ttatgtggtc ttcatatcgc aatgatgcat ttggaggatc ccctggtggt    600
atcactttga cgtcttcctg ggatccatcc actggtattg tttccgaccg cactgtgaca    660
gtcaccaagc atgatatgtt ctgccctggt atctccatgg atggtaacgg tcagatcgta    720
gtcacaggtg gcaacgatgc caagaagacc agtttgtatg attcatctag cgatagctgg    780
atcccgggac ctgacatgca agtggctcgt gggtatcagt catcagctac catgtcagac    840
ggtcgtgttt taccattgg aggctcctgg agcggtggcg tatttgagaa gaatggcgaa    900
gtctatagcc catcttcaaa gacatggacg tccctaccca atgccaaggt caacccaatg    960
ttgacggctg acaagcaagg attgtaccgt tcagacaacc acgcgtggct ctttggatgg   1020
aagaagggtt cggtgttcca agcgggacct agcacagcca tgaactggta ctataccagt   1080
ggaagtggtg atgtgaagtc agccggaaaa cgccagtcta accgtggtgt agcccctgat   1140
gccatgtgcg gaaacgctgt catgtacgac gccgttaaag gaaagatcct gacctttggc   1200
ggctccccag attatcaaga ctctgacgcc acaaccgacg cccacatcat caccctcggt   1260
gaacccggaa catctcccaa cactgtcttt gctagcaatg ggttgtactt tgcccgaacg   1320
tttcacacct ctgttgttct tccagacgga agcacgttta ttacaggagg ccaacgacgt   1380
ggaattccgt tcgaggattc aaccccggta tttacacctg agatctacgt ccctgaacaa   1440
gacactttct acaagcagaa ccccaactcc attgttcgcg tctaccatag catttcccct   1500
ttgttacctg atgcagggt atttaacggt ggtggtggtc tttgtggcga ttgtaccacg   1560
aatcatttcg acgcgcaaat cttttacgcca aactatcttt acaatagcaa cggcaatctc   1620
gcgacacgtc ccaagattac cagaacctct acacagagcg tcaaggtcgg tggcagaatt   1680
acaatctcga cggattcttc gattagcaag gcgtcgttga ttcgctatgg tacagcgaca   1740
cacacggtta atactgacca gcgccgcatt ccctgactc tgacaaacaa tggaggaaat   1800
agctattctt tccaagttcc tagcgactct ggtgttgctt tgcctggcta ctggatgttg   1860
ttcgtgatga actcggccgg tgttcctagt gtggcttcga cgattcgcgt tactcag     1917
```

<210> SEQ ID NO 46
<211> LENGTH: 1917
<212> TYPE: DNA
<213> ORGANISM: Artificial Sequence
<220> FEATURE:
<223> OTHER INFORMATION: Mutant 2.G4 (A1237G, T1650A) of D. Dendroides GaO

<400> SEQUENCE: 46

```
gcctcagcac ctatcggaag cgccatttct cgcaacaact gggccgtcac ttgcgacagt     60
gcacagtcgg gaaatgaatg caacaaggcc attgatggca caaggatac cttttggcac    120 acattctatg cgccaacgg ggatccaaag cccctcaca catacacgat tgacatgaag    180
acaactcaga acgtcaacgg cttgtctatg ctgcctcgac aggatggtaa ccaaaacggc    240
tggatcggtc gccatgaggt ttatctaagc tcagatggca caaactgggg cagccctgtt    300
gcgtcaggta gttggttcgc cgactctact acaaaatact ccaactttga aactcgccct    360
gctcgctatg ttcgtcttgt cgctatcact gaagcgaatg ccagccttg gactagcatt    420 gcagagatca acgtcttcca agctagttct tacacagccc cccagcctgg tcttggacgc    480
tggggtccga ctattgactt accgattgtt cctgcggctg cagcaattga accgacatcg    540
```

-continued

```
ggacgagtcc ttatgtggtc ttcatatcgc aatgatgcat ttggaggatc cctggtggt    600
atcactttga cgtcttcctg ggatccatcc actggtattg tttccgaccg cactgtgaca   660
gtcaccaagc atgatatgtt ctgccctggt atctccatgg atggtaacgg tcagatcgta   720
gtcacaggtg gcaacgatgc caagaagacc agtttgtatg attcatctag cgatagctgg   780
atcccgggac ctgacatgca agtggctcgt gggtatcagt catcagctac catgtcagac   840
ggtcgtgttt taccattgg aggctcctgg agcggtggcg tatttgagaa gaatggcgaa    900
gtctatagcc catcttcaaa gacatggacg tccctaccca atgccaaggt caacccaatg   960
ttgacggctg acaagcaagg attgtaccgt tcagacaacc acgcgtggct ctttggatgg  1020
aagaagggtt cggtgttcca agcgggacct agcacagcca tgaactggta ctataccagt  1080
ggaagtggtg atgtgaagtc agccggaaaa cgccagtcta accgtggtgt agcccctgat  1140
gccatgtgcg gaaacgctgt catgtacgac gccgttaaag gaaagatcct gacctttggc  1200
ggctccccag attatcaaga ctctgacgcc acaaccgacg cccacatcat caccctcggt  1260
gaacccggaa catctcccaa cactgtcttt gctagcaatg ggttgtactt tgcccgaacg  1320
tttcacacct ctgttgttct tccagacgga agcacgttta ttacaggagg ccaacgacgt  1380
ggaattccgt tcgaggattc aaccccggta tttacacctg agatctacgt ccctgaacaa  1440
gacactttct acaagcagaa ccccaactcc attgttcgcg tctaccatag catttccctt  1500
ttgttacctg atgcagggt atttaacggt ggtggtggtc tttgtggcga ttgtaccacg   1560
aatcatttcg acgcgcaaat ctttacgcca aactatcttt acaatagcaa cggcaatctc  1620
gcgacacgtc caagattac cagaacctca cacagagcg tcaaggtcgg tggcagaatt    1680
acaatctcga cggattcttc gattagcaag gcgtcgttga ttcgctatgg tacagcgaca  1740
cacacggtta atactgacca gcgccgcatt cccctgactc tgacaaacaa tggaggaaat  1800
agctattctt tccaagttcc tagcgactct ggtgttgctt tgcctggcta ctggatgttg  1860
ttcgtgatga actcggccgg tgttcctagt gtggcttcga cgattcgcgt tactcag     1917
```

<210> SEQ ID NO 47
<211> LENGTH: 1917
<212> TYPE: DNA
<213> ORGANISM: Artificial Sequence
<220> FEATURE:
<223> OTHER INFORMATION: Mutant 3.H7 (A1237G, T1650A, T1481C) of D. Dendroides GaO

<400> SEQUENCE: 47

```
gcctcagcac ctatcggaag cgccatttct cgcaacaact gggccgtcac ttgcgacagt    60
gcacagtcgg gaaatgaatg caacaaggcc attgatggca acaaggatac cttttggcac   120
acattctatg cgccaacgg ggatccaaag ccccctcaca catacacgat tgacatgaag    180
acaactcaga acgtcaacgg cttgtctatg ctgcctcgac aggatggtaa ccaaaacggc   240
tggatcggtc gccatgaggt ttatctaagc tcagatggca caaactgggg cagccctgtt   300
gcgtcaggta gttggttcgc cgactctact acaaaatact ccaactttga aactcgccct   360
gctcgctatg ttcgtcttgt cgctatcact gaagcgaatg ccagccttg gactagcatt    420
gcagagatca acgtcttcca agctagttct tacacagccc ccagcctgg tcttggacgc    480
tggggtccga ctattgactt accgattgtt cctgcggctg cagcaattga accgacatcg   540
ggacgagtcc ttatgtggtc ttcatatcgc aatgatgcat ttggaggatc cctggtggt    600
atcactttga cgtcttcctg ggatccatcc actggtattg tttccgaccg cactgtgaca   660
```

```
gtcaccaagc atgatatgtt ctgccctggt atctccatgg atggtaacgg tcagatcgta    720
gtcacaggtg gcaacgatgc caagaagacc agtttgtatg attcatctag cgatagctgg    780 atcccggac ctgacatgca agtggctcgt gggtatcagt catcagctac catgtcagac     840
ggtcgtgttt ttaccattgg aggctcctgg agcggtggcg tatttgagaa gaatggcgaa    900
gtctatagcc catcttcaaa gacatggacg tccctaccca atgccaaggt caacccaatg    960
ttgacggctg acaagcaagg attgtaccgt tcagacaacc acgcgtggct ctttggatgg   1020
aagaagggtt cggtgttcca agcgggacct agcacagcca tgaactggta ctataccagt   1080
ggaagtggtg atgtgaagtc agccggaaaa cgccagtcta accgtggtgt agcccctgat   1140
gccatgtgcg gaaacgctgt catgtacgac gccgttaaag gaaagatcct gacctttggc   1200
ggctccccag attatcaaga ctctgacgcc acaaccgacg cccacatcat caccctcggt   1260
gaacccggaa catctcccaa cactgtcttt gctagcaatg ggttgtactt tgcccgaacg   1320
tttcacacct ctgttgttct tccagacgga agcacgttta ttacaggagg ccaacgacgt   1380
ggaattccgt tcgaggattc aaccccggta tttacacctg agatctacgt ccctgaacaa   1440
gacactttct acaagcagaa ccccaactcc attgttcgcg cctaccatag catttcccttt   1500 ttgttacctg atggcagggt atttaacggt ggtggtggtc tttgtggcga ttgtaccacg   1560
aatcatttcg acgcgcaaat ctttacgcca aactatcttt acaatagcaa cggcaatctc   1620
gcgacacgtc ccaagattac cagaacctca acacagagcg tcaaggtcgg tggcagaatt   1680
acaatctcga cggattcttc gattagcaag gcgtcgttga ttcgctatgg tacagcgaca   1740
cacacggtta atactgacca gcgccgcatt cccctgactc tgacaaacaa tggaggaaat   1800
agctattctt tccaagttcc tagcgactct ggtgttgctt tgcctggcta ctggatgttg   1860
ttcgtgatga actcggccgg tgttcctagt gtggcttcga cgattcgcgt tactcag      1917
```

<210> SEQ ID NO 48
<211> LENGTH: 1917
<212> TYPE: DNA
<213> ORGANISM: Artificial Sequence
<220> FEATURE:
<223> OTHER INFORMATION: Mutant 4.F12 (A1237G, T1650A, T1481C, T1830A)
      of D. Dendroides GaO

<400> SEQUENCE: 48

```
gcctcagcac ctatcggaag cgccatttct cgcaacaact gggccgtcac ttgcgacagt     60
gcacagtcgg gaaatgaatg caacaaggcc attgatggca acaaggatac cttttggcac    120
acattctatg cgccaacgg ggatccaaag cccctcaca catacacgat tgacatgaag      180
acaactcaga acgtcaacgg cttgtctatg ctgcctcgac aggatggtaa ccaaaacggc    240
tggatcggtc gccatgaggt ttatctaagc tcagatggca caaactgggg cagccctgtt    300
gcgtcaggta gttggttcgc cgactctact acaaaatact ccaactttga aactcgccct    360
gctcgctatg ttcgtcttgt cgctatcact gaagcgaatg ccagccttg gactagcatt    420 gcagagatca acgtcttcca agctagttct tacacagccc ccagcctgg tcttggacgc    480 tggggtccga ctattgactt accgattgtt cctgcggctg cagcaattga accgacatcg    540
ggacgagtcc ttatgtggtc ttcatatcgc aatgatgcat tggaggatc ccctggtggt    600 atcactttga cgtcttcctg ggatccatcc actggtattg tttccgaccg cactgtgaca    660
gtcaccaagc atgatatgtt ctgccctggt atctccatgg atggtaacgg tcagatcgta    720
gtcacaggtg gcaacgatgc caagaagacc agtttgtatg attcatctag cgatagctgg    780
```

```
atcccgggac ctgacatgca agtggctcgt gggtatcagt catcagctac catgtcagac    840
ggtcgtgttt ttaccattgg aggctcctgg agcggtggcg tatttgagaa gaatggcgaa    900
gtctatagcc catcttcaaa gacatggacg tccctaccca atgccaaggt caacccaatg    960
ttgacggctg acaagcaagg attgtaccgt tcagacaacc acgcgtggct ctttggatgg   1020
aagaagggtt cggtgttcca agcgggacct agcacagcca tgaactggta ctataccagt   1080
ggaagtggtg atgtgaagtc agccggaaaa cgccagtcta accgtggtgt agccctgat   1140 gccatgtgcg gaaacgctgt catgtacgac gccgttaaag gaaagatcct gacctttggc   1200
ggctccccag attatcaaga ctctgacgcc acaaccgacg cccacatcat caccctcggt   1260
gaacccggaa catctcccaa cactgtcttt gctagcaatg ggttgtactt tgcccgaacg   1320
tttcacacct ctgttgttct tccagacgga agcacgttta ttacaggagg ccaacgacgt   1380
ggaattccgt tcgaggattc aaccccggta tttacacctg agatctacgt ccctgaacaa   1440
gacactttct acaagcagaa ccccaactcc attgttcgcg cctaccatag catttccctt   1500
ttgttacctg atggcagggt atttaacggt ggtggtggtc tttgtggcga ttgtaccacg   1560
aatcatttcg acgcgcaaat ctttacgcca aactatcttt acaatagcaa cggcaatctc   1620
gcgacacgtc ccaagattac cagaacctca acacagagcg tcaaggtcgg tggcagaatt   1680
acaatctcga cggattcttc gattagcaag gcgtcgttga ttcgctatgg tacagcgaca   1740
cacacggtta atactgacca gcgccgcatt cccctgactc tgacaaacaa tggaggaaat   1800
agctattctt tccaagttcc tagcgactca ggtgttgctt tgcctggcta ctggatgttg   1860
ttcgtgatga actcggccgg tgttcctagt gtggcttcga cgattcgcgt tactcag     1917
```